(12) United States Patent
Ren et al.

(10) Patent No.: US 10,700,287 B2
(45) Date of Patent: Jun. 30, 2020

(54) ORGANIC ELECTROLUMINESCENT COMPOUND AND ORGANIC PHOTOELECTRIC APPARATUS

(71) Applicants: Shanghai Tianma AM-OLED Co., Ltd., Shanghai (CN); Tianma Micro-electronics Co., Ltd., Shenzhen (CN)

(72) Inventors: Hongyang Ren, Shanghai (CN); Xiangcheng Wang, Shanghai (CN); Wei He, Shanghai (CN)

(73) Assignees: Shanghai Tianma AM-OLED Co., Ltd., Shanghai (CN); Tianma Micro-electronics Co., Ltd., Shenzhen (CN)

( * ) Notice: Subject to any disclaimer, the term of this patent is extended or adjusted under 35 U.S.C. 154(b) by 208 days.

(21) Appl. No.: 15/134,673

(22) Filed: Apr. 21, 2016

(65) Prior Publication Data

US 2017/0186962 A1    Jun. 29, 2017

(30) Foreign Application Priority Data

Dec. 25, 2015    (CN) .......................... 2015 1 0995978

(51) Int. Cl.
 *H01L 51/00* (2006.01)
 *C09K 11/06* (2006.01)
 (Continued)

(52) U.S. Cl.
 CPC ........ *H01L 51/0067* (2013.01); *C07D 401/14* (2013.01); *C07D 413/14* (2013.01);
 (Continued)

(58) Field of Classification Search
 CPC ............. H01L 51/0067; H01L 51/0071; H01L 51/0072; H01L 51/0094; H01L 51/5012
 See application file for complete search history.

(56) References Cited

U.S. PATENT DOCUMENTS

2014/0070146 A1\* 3/2014 Parham ............... H01L 51/0067
                                                          252/500
2017/0279055 A1\* 9/2017 Jang ........................ C09K 11/06

FOREIGN PATENT DOCUMENTS

CN          103503188 A       1/2014
CN          104011894 A       8/2014
                    (Continued)

*Primary Examiner* — Bethany L Martin
(74) *Attorney, Agent, or Firm* — Anova Law Group PLLC

(57) ABSTRACT

The present disclosure provides a nitrogen-containing heterocyclic compound having a general formula (I) and an organic photoelectric apparatus thereof. The general formula (I) is

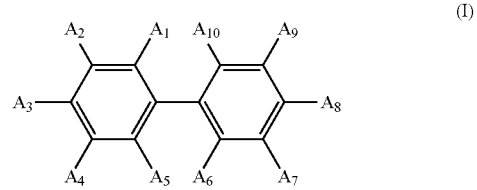

wherein $A_1$, $A_2$, $A_3$, $A_4$, $A_5$, $A_6$, $A_7$, $A_8$, $A_9$, and $A_{10}$ are independently selected from a hydrogen atom, at least (Continued)

one compound having the general formula (II) and at least one compound having a general formula (III),

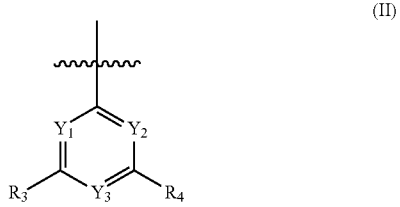

(II)

wherein $Y_1$, $Y_2$, and $Y_3$ are independently selected from C and N; and $R_3$ and $R_4$ are independently selected from $C_{6-30}$ aromatic group and $C_{2-30}$ heterocyclic aromatic group,

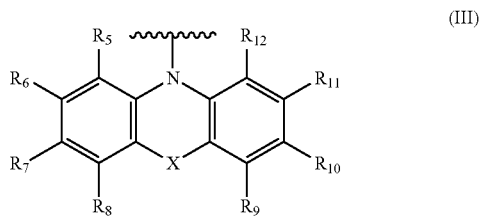

(III)

wherein X is selected from oxyl group, sulfenyl group, substituted or non-substituted imino group, substituted or non-substituted methylene group, and substituted or non-substituted silicylene group, and $R_5$, $R_6$, $R_7$, $R_8$, $R_9$, $R_{10}$, $R_{11}$, and $R_{12}$ are independently selected from hydrogen, deuterium, $C_{1-30}$ alkyl group, $C_{6-30}$ aromatic group, and $C_{2-30}$ heterocyclic aromatic group.

17 Claims, 3 Drawing Sheets

(51) Int. Cl.
| | | |
|---|---|---|
| *C07D 417/14* | (2006.01) | |
| *C07D 401/14* | (2006.01) | |
| *C07D 413/14* | (2006.01) | |
| *C07F 7/08* | (2006.01) | |
| *C09K 11/02* | (2006.01) | |
| *H01L 51/50* | (2006.01) | |
| *H01L 51/56* | (2006.01) | |

(52) U.S. Cl.
CPC .......... *C07D 417/14* (2013.01); *C07F 7/0816* (2013.01); *C09K 11/025* (2013.01); *C09K 11/06* (2013.01); *H01L 51/0054* (2013.01); *H01L 51/0071* (2013.01); *H01L 51/0072* (2013.01); *H01L 51/0094* (2013.01); *C09K 2211/1007* (2013.01); *C09K 2211/1059* (2013.01); *C09K 2211/1074* (2013.01); *C09K 2211/1077* (2013.01); *C09K 2211/1081* (2013.01); *C09K 2211/1085* (2013.01); *H01L 51/0002* (2013.01); *H01L 51/5012* (2013.01); *H01L 51/56* (2013.01)

(56) References Cited

FOREIGN PATENT DOCUMENTS

| | | | | |
|---|---|---|---|---|
| CN | 104136430 | A | 11/2014 | |
| CN | 104716268 | A | 6/2015 | |
| EP | 3222695 | * | 9/2017 | ............ H01L 51/50 |
| JP | 2011176250 | A | 9/2011 | |
| JP | 2011210749 | A | 10/2011 | |
| TW | 201443028 | A | 11/2014 | |
| WO | 2015175678 | A1 | 11/2015 | |
| WO | 2016080622 | A1 | 5/2016 | |
| WO | WO2016080622 | * | 5/2016 | ............ H01L 51/50 |

* cited by examiner

ORGANIC ELECTROLUMINESCENT COMPOUND AND ORGANIC PHOTOELECTRIC APPARATUS

CROSS-REFERENCES TO RELATED APPLICATIONS

This application claims the priority of Chinese patent application No. 201510995978.0, filed on Dec. 25, 2015, the entirety of which is incorporated herein by reference.

FIELD OF THE INVENTION

The present invention generally relates to the field of organic electroluminescent material and, more particularly, relates to organic electroluminescent materials and their applications in organic photoelectric apparatus.

BACKGROUND

Recently, organic light-emitting diode (OLED) has become a mostly focused new generation of display products because of its self-emitting characteristics, high-efficiency, wide color region, and wide viewing-angles, etc. The organic material used to form the OLED plays an important role in developing OLED.

When the organic material in a light-emitting layer of an OLED is electrically activated, the singlet excitons ($S_1$) and the triplet excitons ($T_1$) are generated. According to the self-spin statistics, the ratio of the singlet excitons ($S_1$) to the triplet excitons ($T_1$) is 1:3. According to the light-emitting principles, the materials of the light-emitting layer of the OLED include fluorescent materials and phosphorescent materials.

The fluorescent materials are only able to use 25% of singlet excitons (S1), which can be back to the ground state S0 by a radiative transition. The phosphorescent materials are able to use not only the 25% of singlet excitons ($S_1$), but also 75% of the triplet excitons (T1). Thus, theoretically, the quantum efficiency of phosphorescent materials is 100%; and they are superior to the fluorescence materials when they are used in the OLED. However, the phosphorescent materials are usually rare metal complexes, the material cost is relatively high. Further, the blue phosphorescent materials have always been having issues on the efficiency and the lifespan when they are applied in the OLED.

In 2011, professor Adachi at Kyushu University, Japan, reported the thermally activated delayed fluorescence (TADF) material. Such a material presented a relatively good light-emitting performance. The band gap value of the $S_1$ state and the $T_1$ state of the TADF material is relatively small; and the lifespan of the $T_1$ excitons of the TADF material is relatively long. Under a certain temperature condition, the $T_1$ excitons may have a reverse intersystem crossing (RISC) to achieve the $T_1 \rightarrow S_1$ process; and achieve a radiative decay from the $S_1$ state to the ground state $S_0$. Thus, when the TADF material is used as the light-emitting layer in the OLED, the light-emitting efficiency of the OLED may be comparable to that of the OLED using the phosphorescent materials as the light-emitting layer. Further, the TADF material does not need rare-metal elements. Thus, the material cost is relatively low.

However, the existing types of TADF materials are limited; and there is a need to develop novel TADF materials with enhanced performance. The disclosed methods and material structures are directed to solve one or more problems set forth above and other problems in the art.

BRIEF SUMMARY OF THE DISCLOSURE

One aspect of the present disclosure includes a nitrogen-containing heterocyclic compound having a general formula (I):

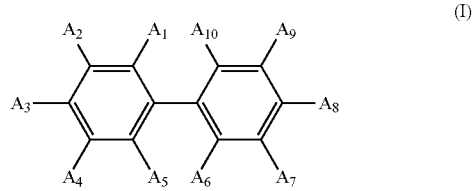

where $A_1$, $A_2$, $A_3$, $A_4$, $A_5$, $A_6$, $A_7$, $A_8$, $A_9$, and $A_{10}$ are independently selected from a hydrogen atom, a compound having a general formula (II) and a compound having a general formula (III), and $A_1$, $A_2$, $A_3$, $A_4$, $A_5$, $A_6$, $A_7$, $A_8$, $A_9$, and $A_{10}$ include at least one compound having the general formula (II) and at least one compound having the general formula (III), the general formula (II) being:

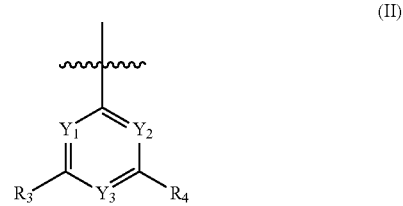

where $Y_1$, $Y_2$, and $Y_3$ are independently selected from C and N; and $R_3$ and $R_4$ are independently selected from $C_{6-30}$ aromatic group and $C_{2-30}$ heterocyclic aromatic group, and the general formula (III) being:

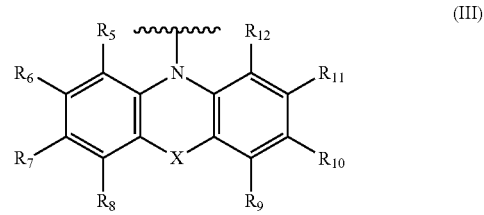

where X is selected from any one of oxyl group (—O—), sulfhydryl group (—S—) group, substituted or non-substituted imino group, substituted or non-substituted methylene group, and substituted or non-substituted silicylene group; and $R_5$, $R_6$, $R_7$, $R_8$, $R_9$, $R_{10}$, $R_{11}$, and $R_{12}$ are independently selected from hydrogen, deuterium, $C_{1-30}$ alkyl group, $C_{6-30}$ aromatic group, and $C_{2-30}$ heterocyclic aromatic group.

Another aspect of the present disclosure includes an organic photoelectric apparatus. The organic photoelectric apparatus includes an anode substrate, at least one organic layer formed over the anode substrate, and a cathode formed over the organic layer. The organic layer includes at least one nitrogen-containing heterocyclic compound having a general formula (I):

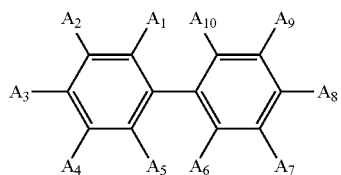

(I)

where $A_1$, $A_2$, $A_3$, $A_4$, $A_5$, $A_6$, $A_7$, $A_8$, $A_9$, and $A_{10}$ are independently selected from a hydrogen atom, a compound having a general formula (II) and a compound having a general formula (III), and $A_1$, $A_2$, $A_3$, $A_4$, $A_5$, $A_6$, $A_7$, $A_8$, $A_9$, and $A_{10}$ include at least one compound having the general formula (II) and at least one compound having the general formula (III), the general formula (II) being:

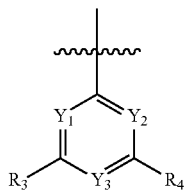

(II)

where $Y_1$, $Y_2$, and $Y_3$ are independently selected from C and N; and $R_3$ and $R_4$ are independently selected from $C_{6-30}$ aromatic group and $C_{2-30}$ heterocyclic aromatic group, and the general formula (III) being:

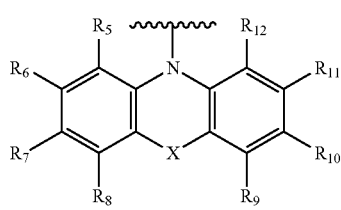

(III)

where X is selected from any one of oxyl group (—O—), sulfhydryl group (—S—) group, substituted or non-substituted imino group, substituted or non-substituted methylene group, and substituted or non-substituted silicylene group; and $R_5$, $R_6$, $R_7$, $R_8$, $R_9$, $R_{10}$, $R_{11}$, and $R_{12}$ are independently selected from hydrogen, deuterium, $C_{1-30}$ alkyl group, $C_{6-30}$ aromatic group, and $C_{2-30}$ heterocyclic aromatic group.

Another aspect of the present disclosure includes a process for fabricating an organic photoelectric apparatus. The method includes providing an anode substrate; forming at least one organic layer over the anode substrate; and forming a cathode layer over the organic layer, the at least one organic layer includes at least one nitrogen-containing heterocyclic compound having a general formula (I):

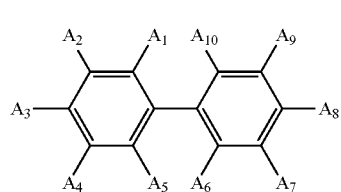

(I)

where $A_1$, $A_2$, $A_3$, $A_4$, $A_5$, $A_6$, $A_7$, $A_8$, $A_9$, and $A_{10}$ are independently selected from a hydrogen atom, a compound having a general formula (II) and a compound having a general formula (III), and $A_1$, $A_2$, $A_3$, $A_4$, $A_5$, $A_6$, $A_7$, $A_8$, $A_9$, and $A_{10}$ include at least one compound having the general formula (II) and at least one compound having the general formula (III), the general formula (II) being:

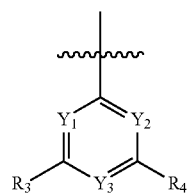

(II)

where $Y_1$, $Y_2$, and $Y_3$ are independently selected from C and N; and $R_3$ and $R_4$ are independently selected from $C_{6-30}$ aromatic group and $C_{2-30}$ heterocyclic aromatic group, and the general formula (III) being:

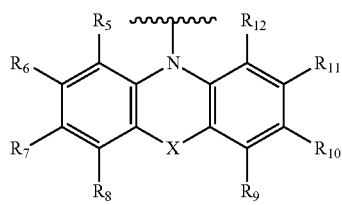

(III)

where X is selected from any one of oxyl group (—O—), sulfhydryl group (—S—) group, substituted or non-substituted imino group, substituted or non-substituted methylene group, and substituted or non-substituted silicylene group; and $R_5$, $R_6$, $R_7$, $R_8$, $R_9$, $R_{10}$, $R_{11}$, and $R_{12}$ are independently selected from hydrogen, deuterium, $C_{1-30}$ alkyl group, $C_{6-30}$ aromatic group, and $C_{2-30}$ heterocyclic aromatic group.

Other aspects of the present disclosure can be understood by those skilled in the art in light of the description, the claims, and the drawings of the present disclosure.

DETAILED DESCRIPTION

Figure 1:
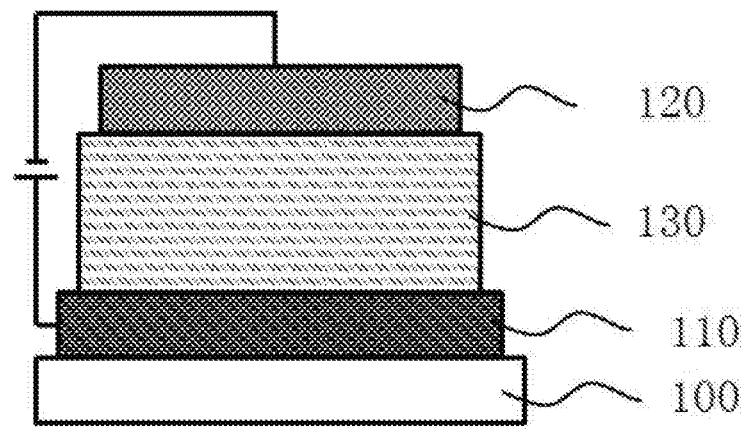
FIG. 1 illustrates an exemplary OLED consistent with the disclosed embodiments.

Reference will now be made in detail to exemplary embodiments of the invention, which are illustrated in the accompanying drawings. Wherever possible, the same reference numbers will be used throughout the drawings to refer to the same or like parts.

According to the disclosed embodiments, a compound having a general formula (I) is provided. The general formula (I) may be:

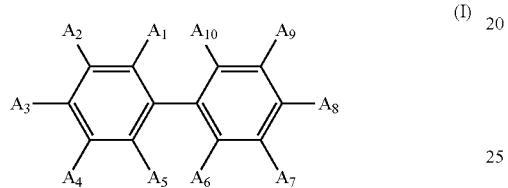
(I)

where $A_1$, $A_2$, $A_3$, $A_4$, $A_5$, $A_6$, $A_7$, $A_8$, $A_9$, and $A_{10}$ may be independently selected from a hydrogen atom, a compound having a general formula (II) and a compound having a general formula (III), etc. Further, $A_1$, $A_2$, $A_3$, $A_4$, $A_5$, $A_6$, $A_7$, $A_8$, $A_9$, and $A_{10}$ may include at least one compound of the general formula (II) and at least one compound of the general formula (III). According to the general formula (II) and the general formula (III), the present disclosed compound may be referred to as a nitrogen-containing heterocyclic compound.

The general formula (II) may be:

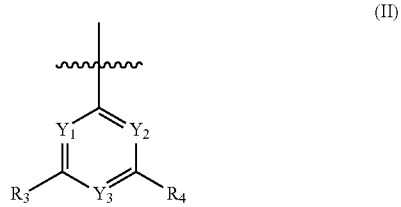
(II)

where $Y_1$, $Y_2$, and $Y_3$ may be independently selected from C and N, etc. $R_3$ and $R_4$ may be independently selected from $C_{6-30}$ aromatic group, and $C_{2-30}$ heterocyclic aromatic group, etc.

The general formula (III) may be:

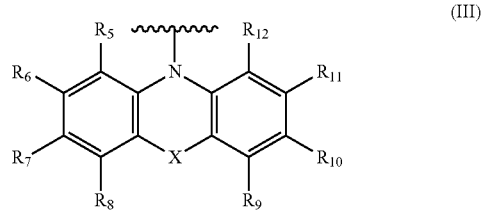
(III)

where X may be selected from oxyl group (—O—), sulfhydryl group (—S—), substituted or non-substituted imino group, substituted or non-substituted methylene group, and substituted or non-substituted silicylene group, etc. $R_5$, $R_6$, $R_7$, $R_8$, $R_9$, $R_{10}$, $R_{11}$, and $R_{12}$ may be independently selected from any one of hydrogen, deuterium, $C_{1-30}$ alkyl group, $C_{6-30}$ aromatic group, and $C_{2-30}$ heterocyclic aromatic group, etc.

In one embodiment, the $C_1$-$C_{30}$ alkyl group includes the alkyl group having 1-20 carbon atoms. In certain other embodiments, the $C_1$-$C_{30}$ alkyl group includes the alkyl group having 1-10 carbon atoms. In still certain other embodiments, the $C_1$-$C_{30}$ alkyl group includes the alkyl group having 1-6 carbon atoms.

In one embodiment, the oxyl group may be

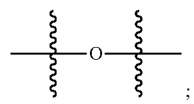 [SMILES: *O*]

the sulfhydryl group may be

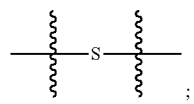 [SMILES: *S*]

the substituted or non-substituted imine group may be

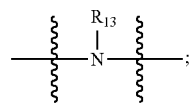

the substituted or non-substituted methylene group may be

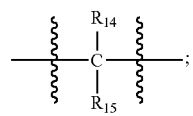

and the substituted or non-substituted silicylene group may be

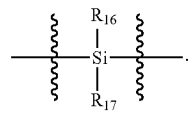

The $R_{13}$, $R_{14}$, $R_{15}$, $R_{16}$, and $R_{17}$ may be independently selected from hydrogen, deuterium, $C_{1-30}$ alkyl group, $C_{6-30}$ aromatic group, and $C_{2-30}$ heterocyclic aromatic group, etc.

In one embodiment, the energy level difference ($\Delta E_{st}$) between the lowest singlet state $S_1$ ($E_{s1}$) and the lower triplet state $T_1$ ($E_{T1}$) may be $\Delta E_{st}=E_{s1}-E_{T1} \leq 0.30$ eV, such as 0.29 eV, 0.28 eV, 0.27 eV, 0.26 eV, 0.25 eV, 0.24 eV, 0.23 eV, 0.22 eV, 0.21 eV, 0.20 eV, 0.19 eV, 0.18 eV, 0.17 eV, 0.16 eV, 0.15 eV, 0.14 eV, 0.13 eV, 0.12 eV, 0.11 eV, 0.10 eV, 0.09 eV, 0.08 eV, 0.07 eV, 0.06 eV, 0.05 eV, 0.04 eV, 0.03 eV, 0.02 eV or 0.01 eV, etc. When $\Delta E_{st} \leq 0.30$ eV, the fluorescent delay effect of the disclosed compound may not be obvious.

In one embodiment, the $\Delta E_{st}$ of the disclosed compound having the general formula (I) is smaller than approximately 0.25 eV. That is, $\Delta E_{st} \leq 0.25$ eV.

In certain other embodiments, the $\Delta E_{st}$ of the disclosed compound having the general formula (I) is smaller than approximately 0.15 eV. That is, $\Delta E_{st} \leq 0.15$ eV.

In still certain other embodiments, the $\Delta E_{st}$ of the disclosed compound having the general formula (I) is smaller than approximately 0.10 eV. That is, $\Delta E_{st} \leq 0.10$ eV.

In still certain other embodiments, the $\Delta E_{st}$ of the disclosed compound having the general formula (I) is smaller than approximately 0.05 eV. That is, $\Delta E_{st} \leq 0.05$ eV.

In still certain other embodiments, the $\Delta E_{st}$ of the disclosed compound having the general formula (I) is smaller than approximately 0.02 eV. That is, $\Delta E_{st} \leq 0.02$ eV.

In still certain other embodiments, the $\Delta E_{st}$ of the disclosed compound having the general formula (I) is smaller than approximately 0.01 eV. That is, $\Delta E_{st} \leq 0.01$ eV.

Such ranges of $\Delta E_{st}$ of the disclosed compound having the general formula (I) may have obvious fluorescent effect during the static tests.

In one embodiment, the compound having the general formula (II) may be one selected from

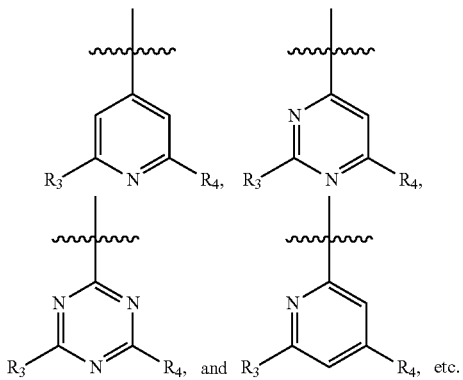

In one embodiment, $R_3$ and $R_4$ may be independently one or more selected from substituted or nonsubstituted phenyl group, substituted or non-substituted pyridyl group, substituted or non-substituted pyrimidyl group, and substituted or non-substituted triazinyl group, etc.

In one embodiment, the compound having the general formula (II) may be one or more of:

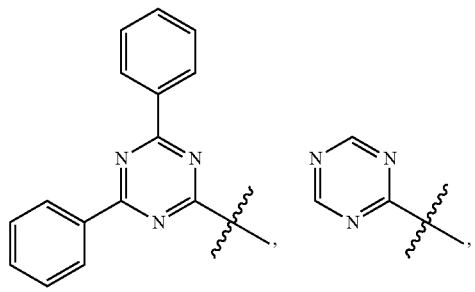

-continued

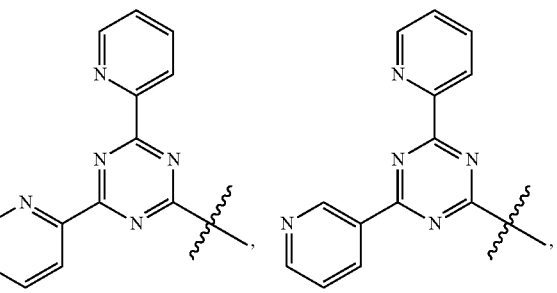

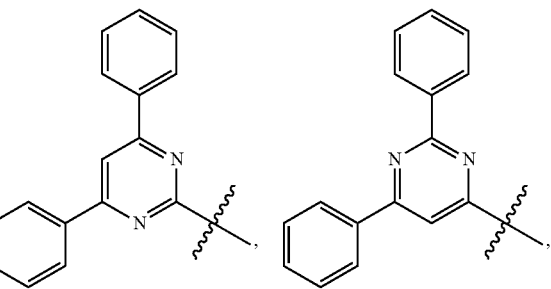

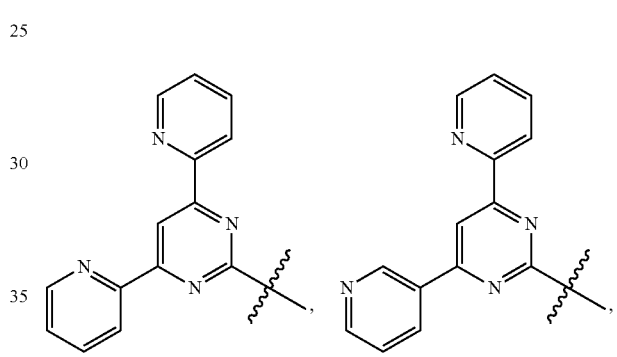

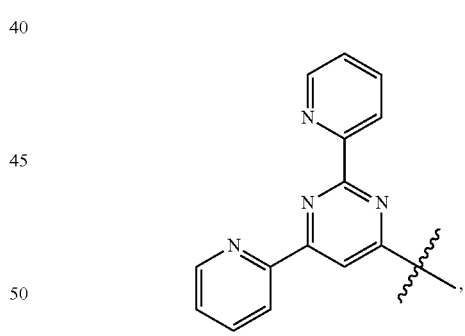

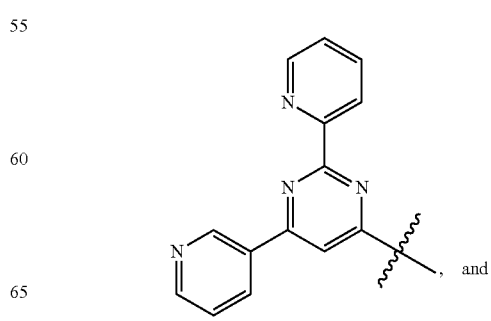

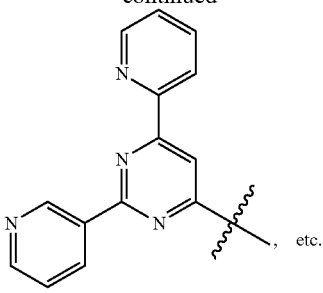, etc.

In one embodiment, the X in the compound having the general formula (III) may be one selected from —O—, —S—, —NH—, —N(CH₃)—,

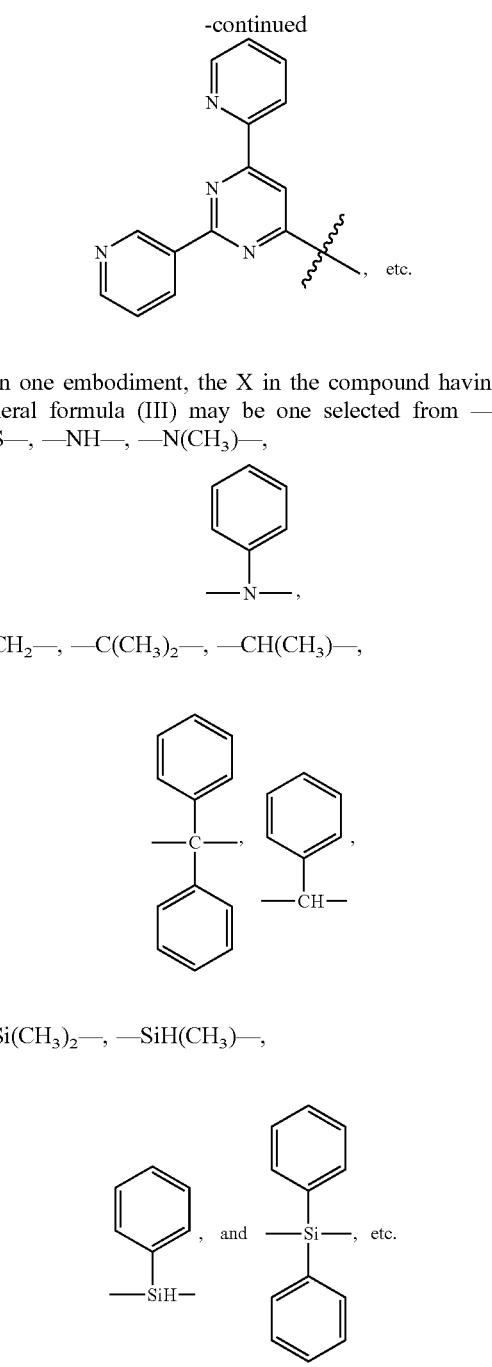

—CH₂—, —C(CH₃)₂—, —CH(CH₃)—,

—Si(CH₃)₂—, —SiH(CH₃)—,

In certain other embodiments, $R_5$, $R_6$, $R_7$, $R_8$, $R_9$, $R_{10}$, $R_{11}$ and $R_{12}$ may all be hydrogen.

In one embodiment, the compound having the general formula (III) may be one or more of

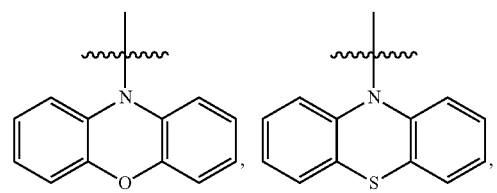

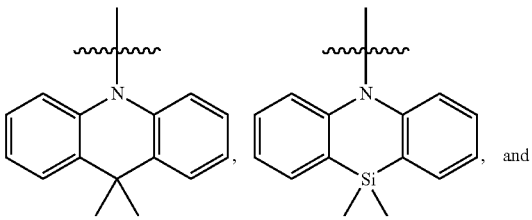, and

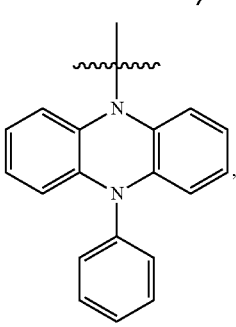, etc.

In one embodiment, the present disclosed nitrogen-containing heterocyclic compound may be one selected from the following compounds 1-204.

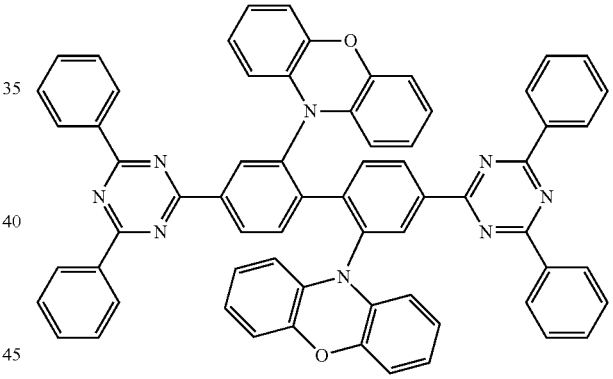

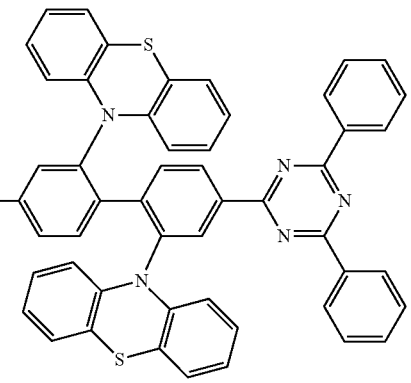

3
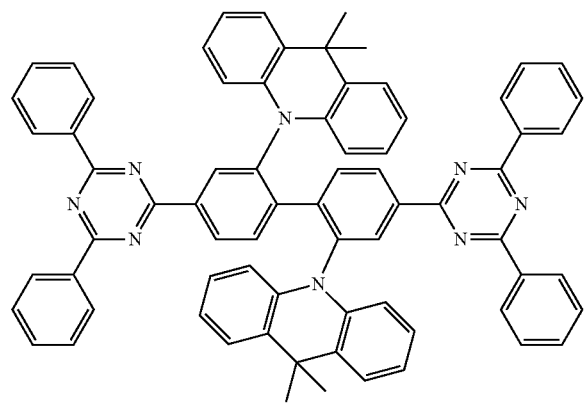
4
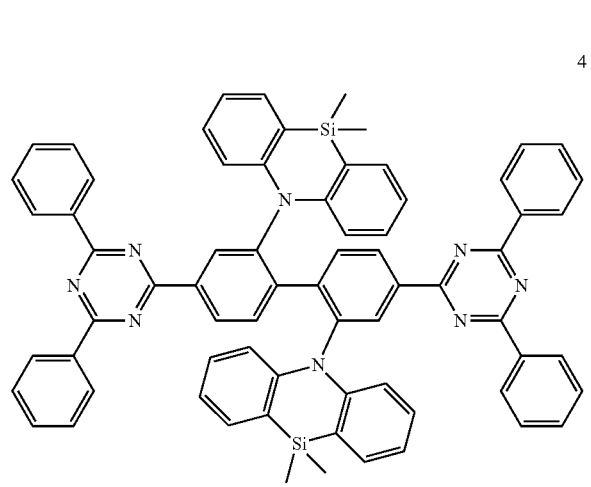
5
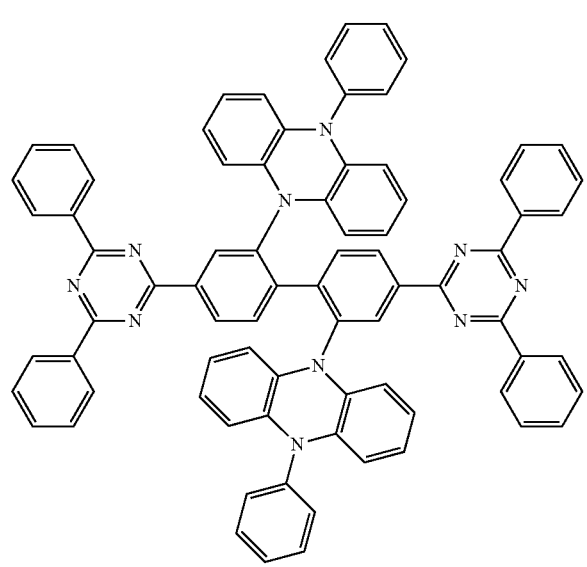
6
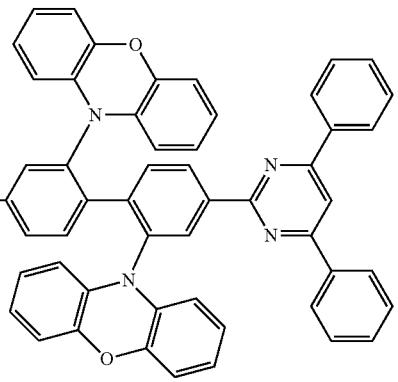
7
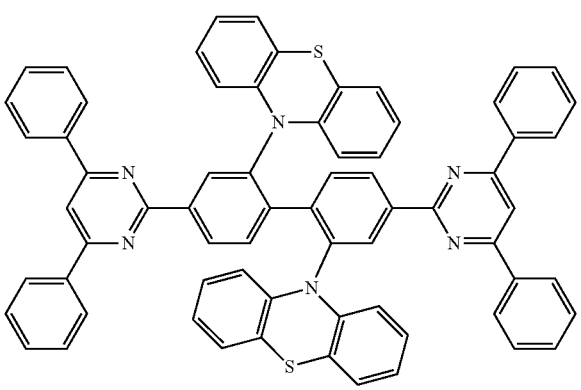
8
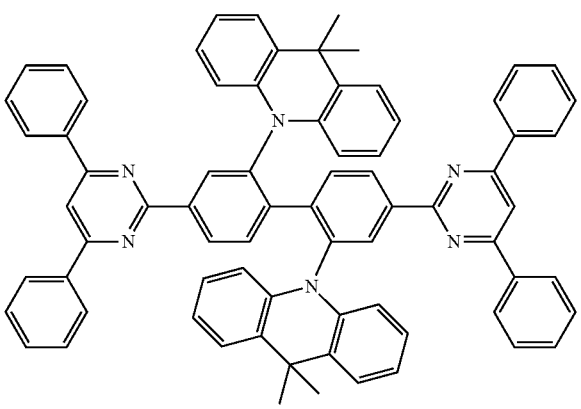
9
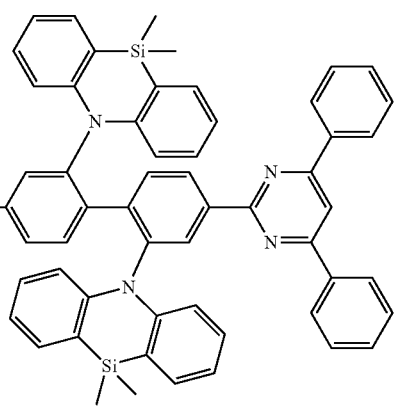

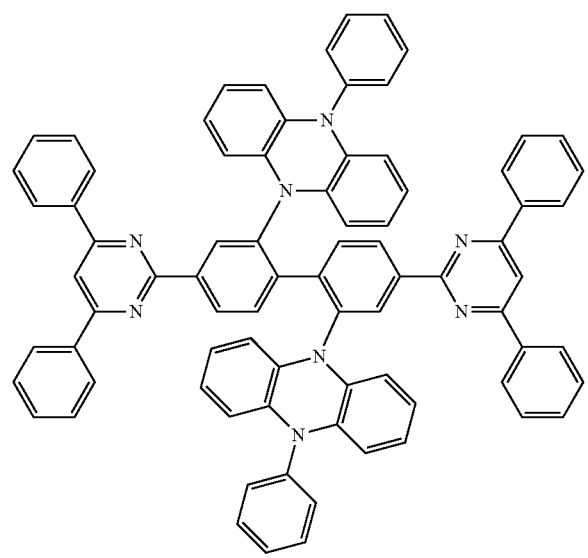
10
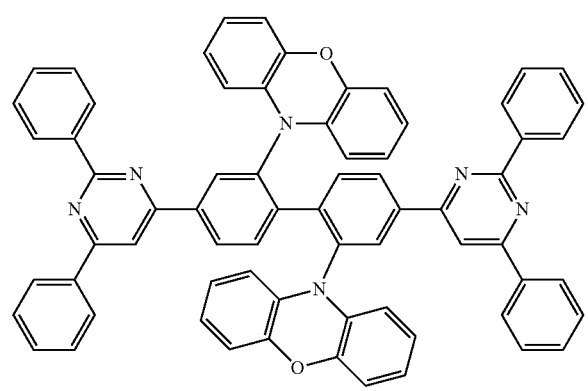
11
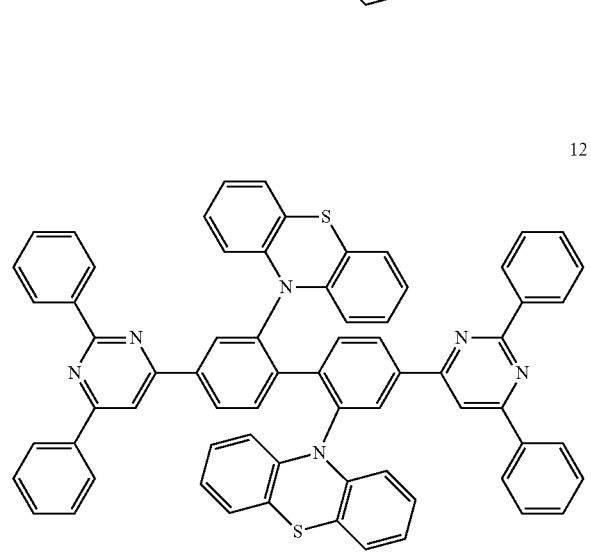
12
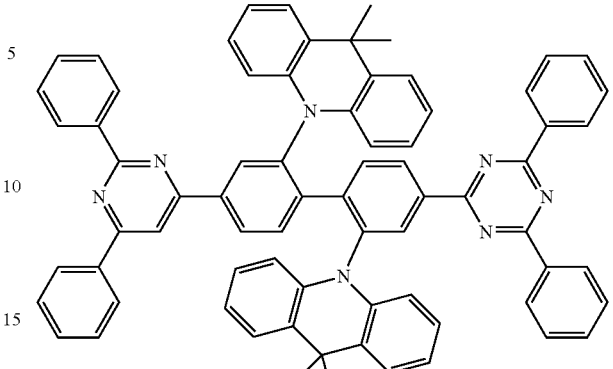
13
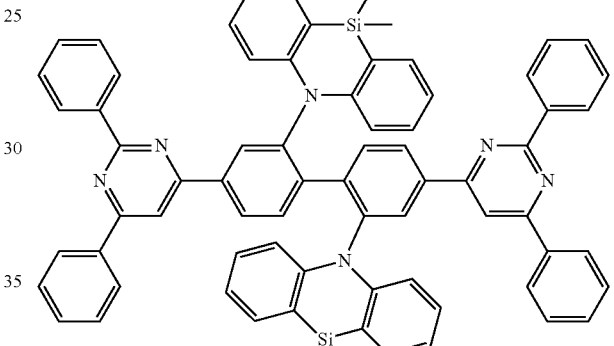
14
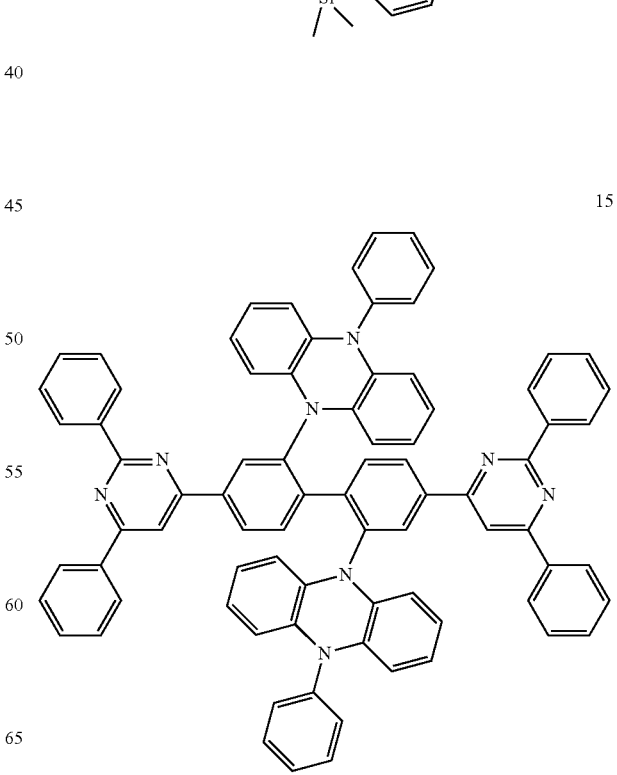
15

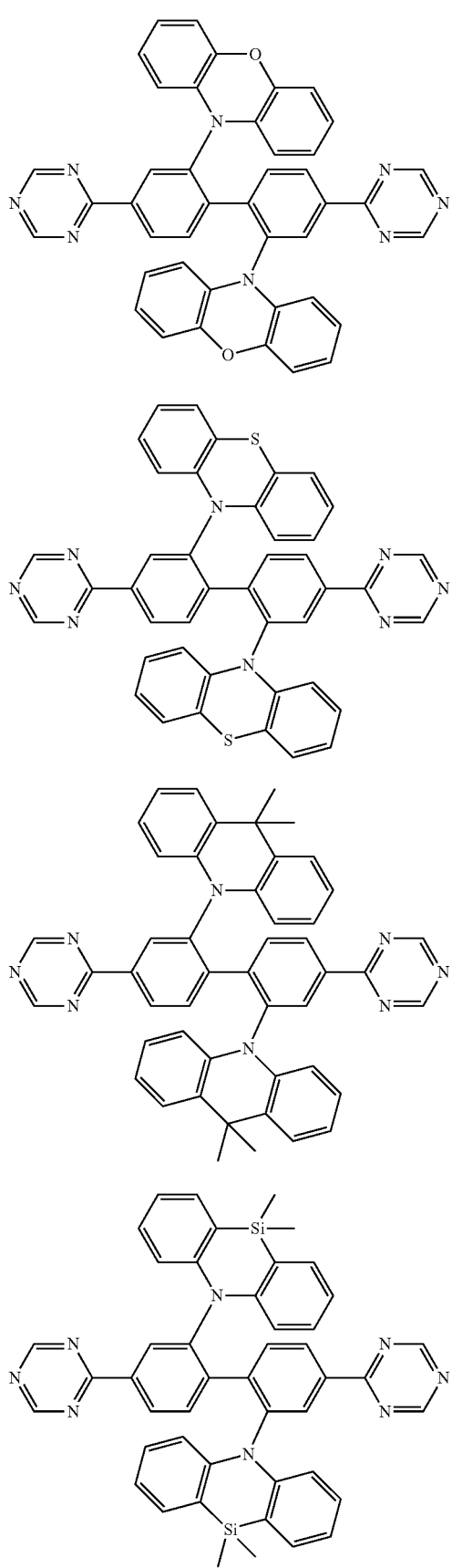
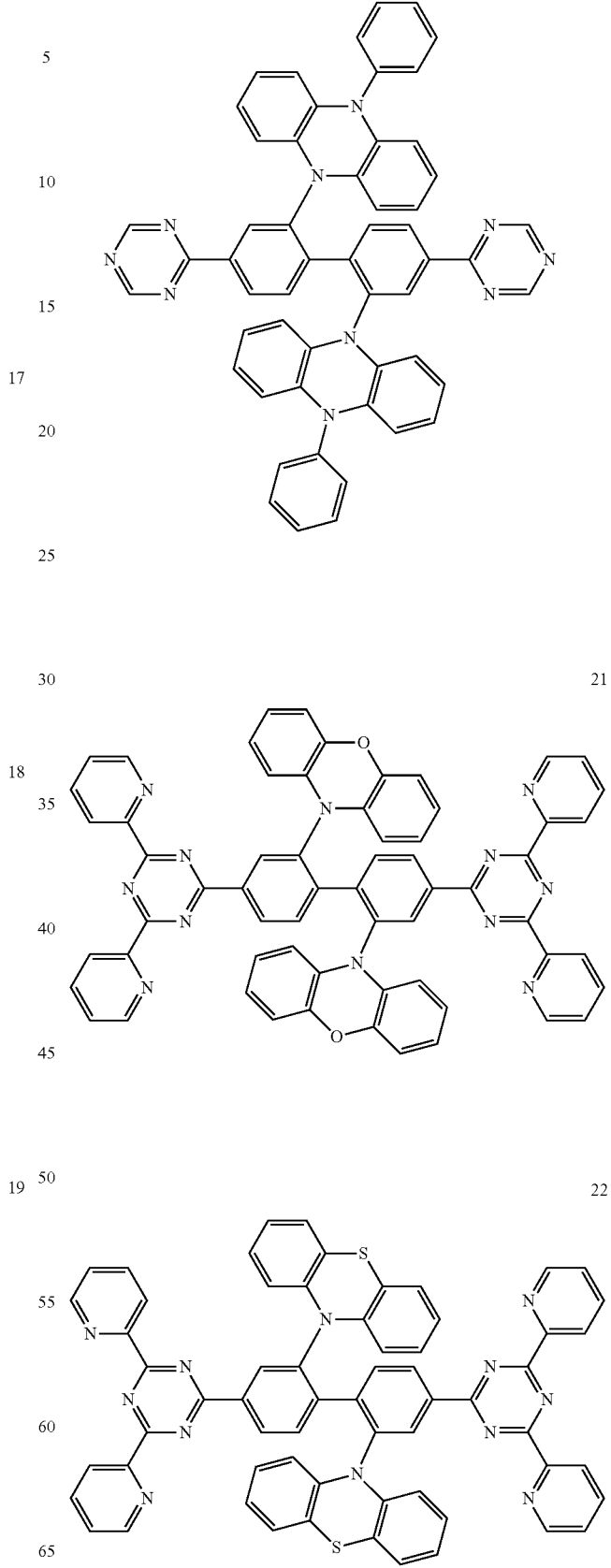

23
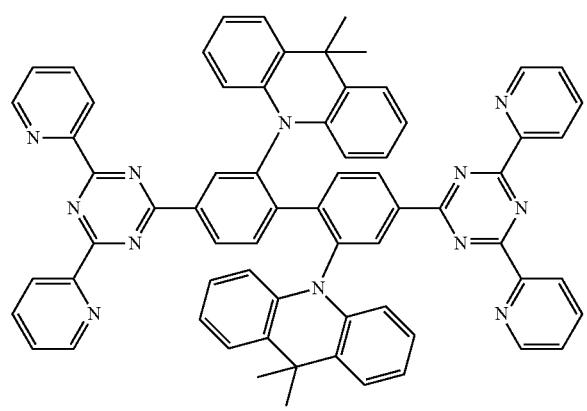
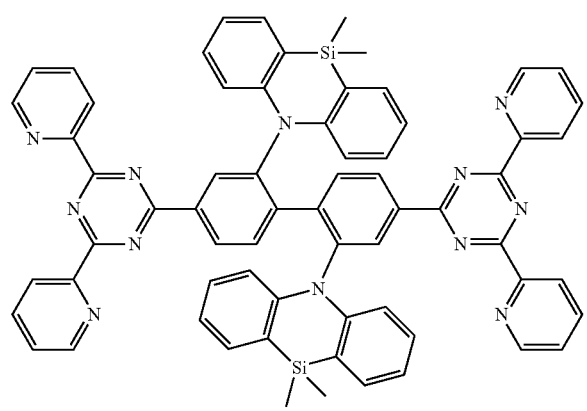
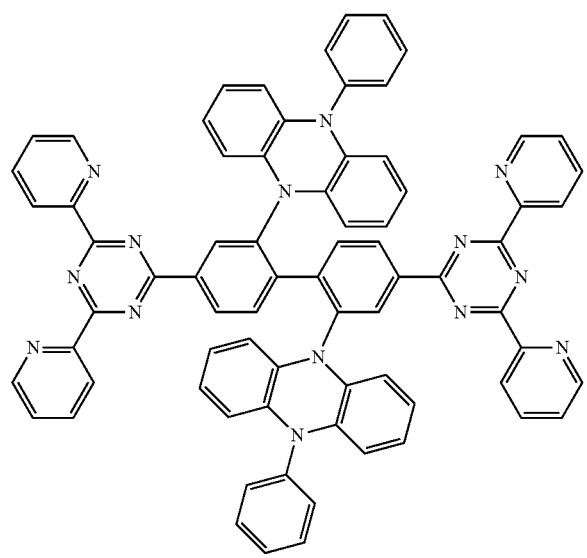
26
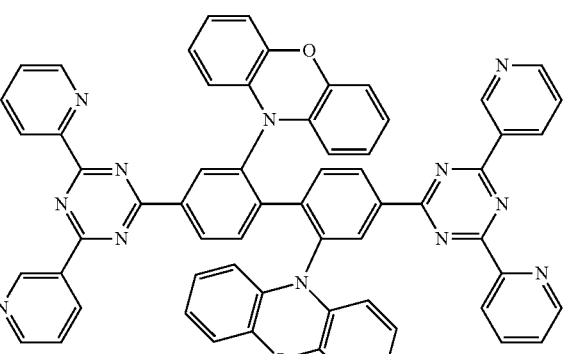
27
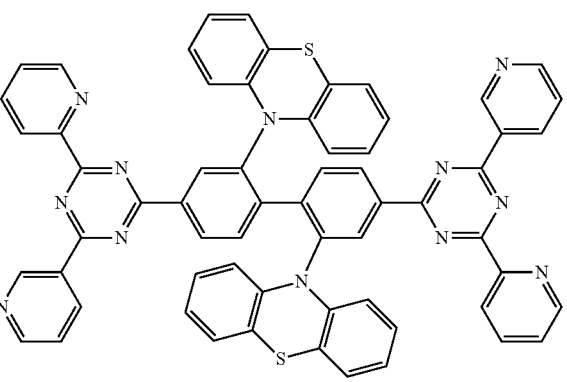
28
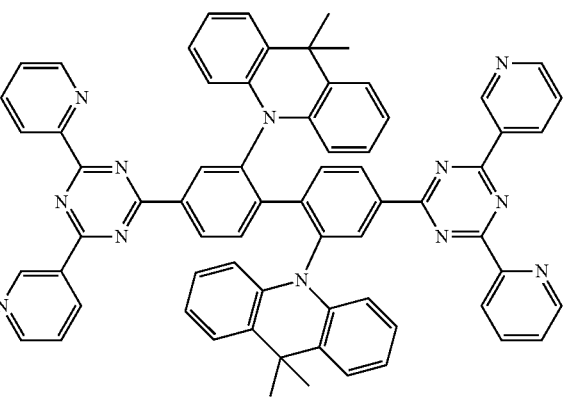
29
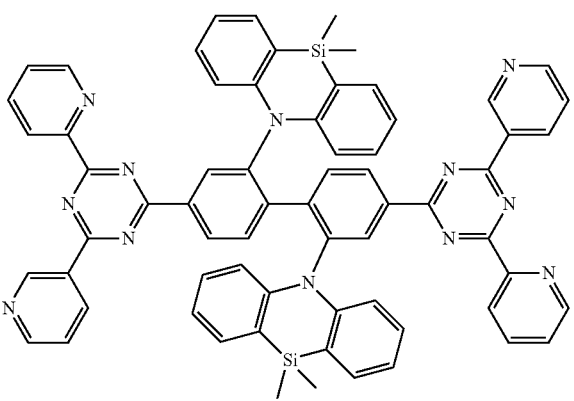

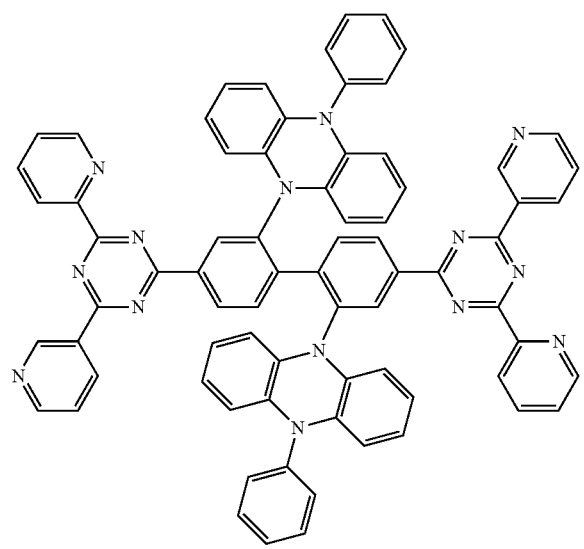
30
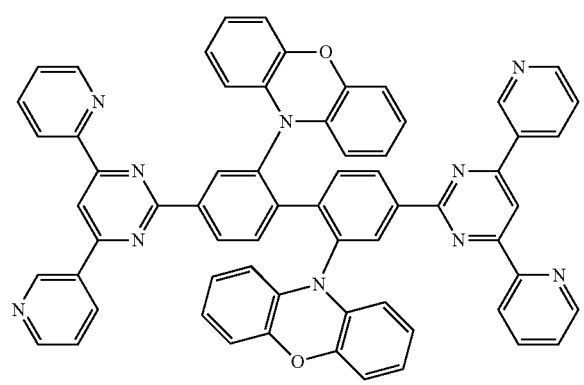
31
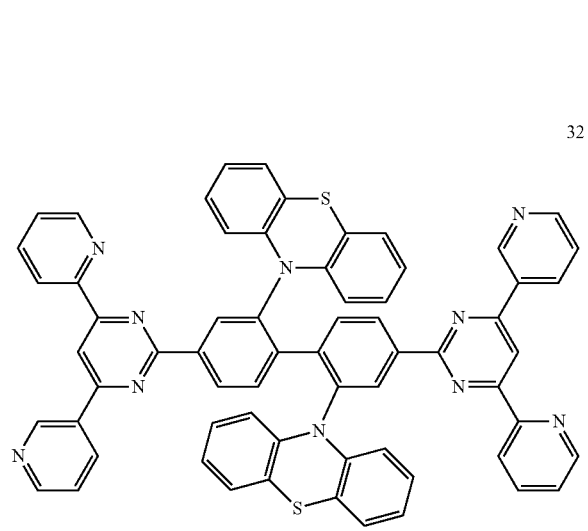
32
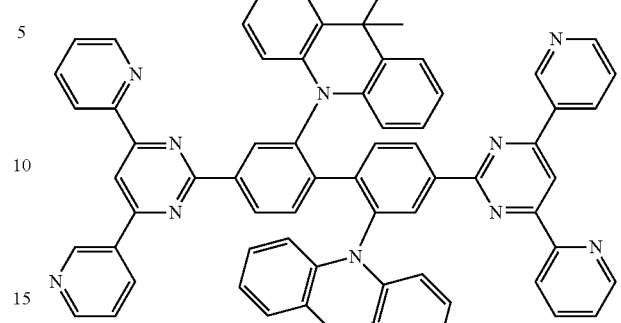
33
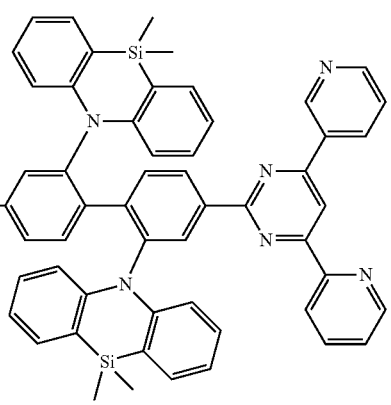
34
35

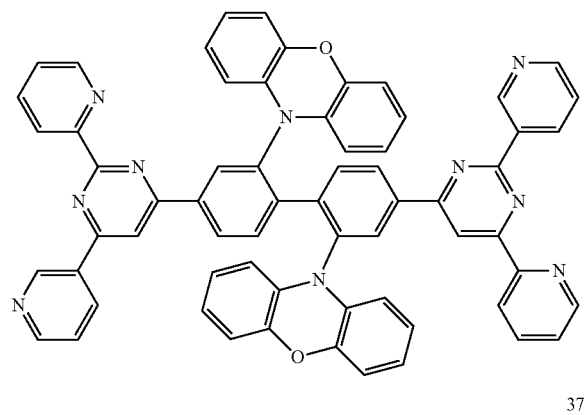
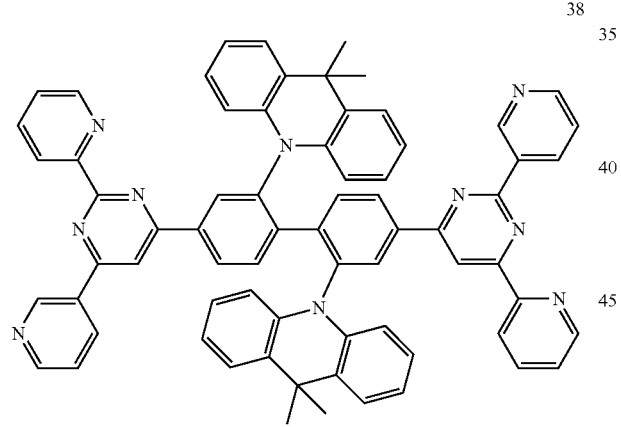
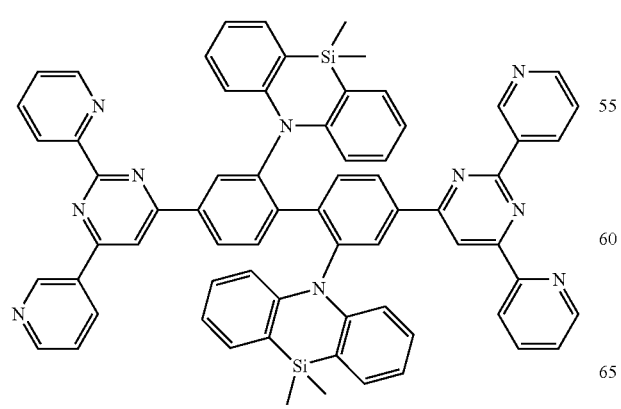
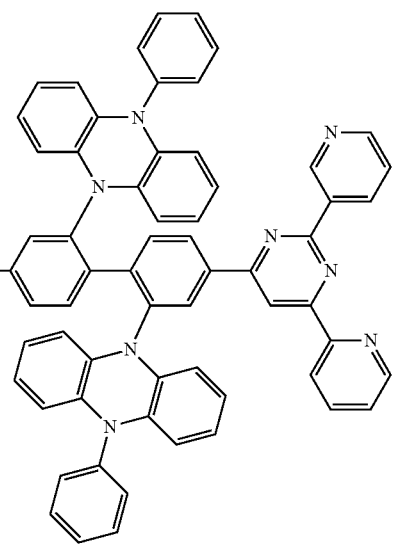
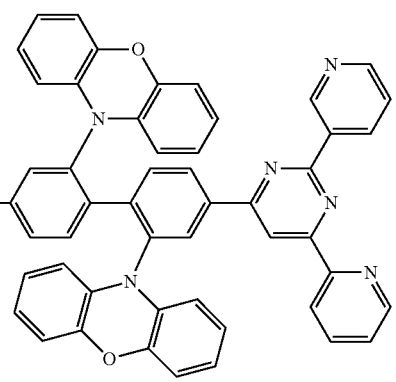
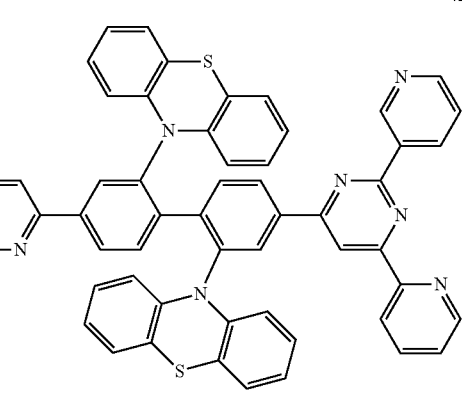

-continued

49
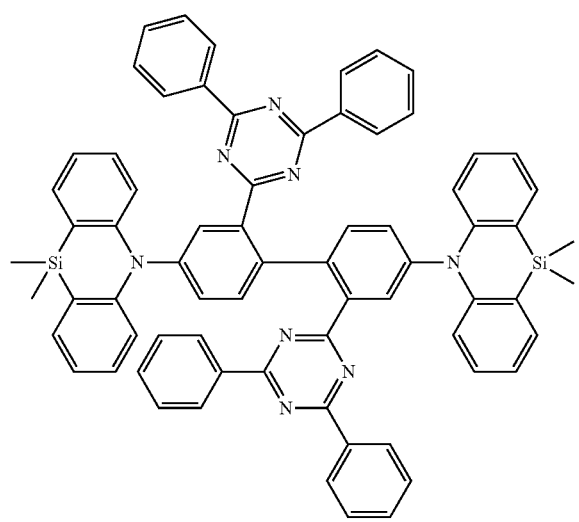
50
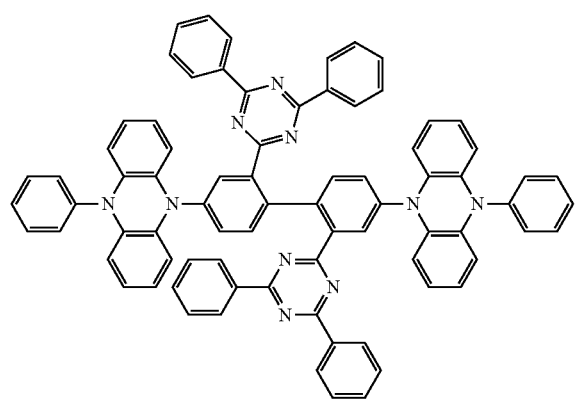
51
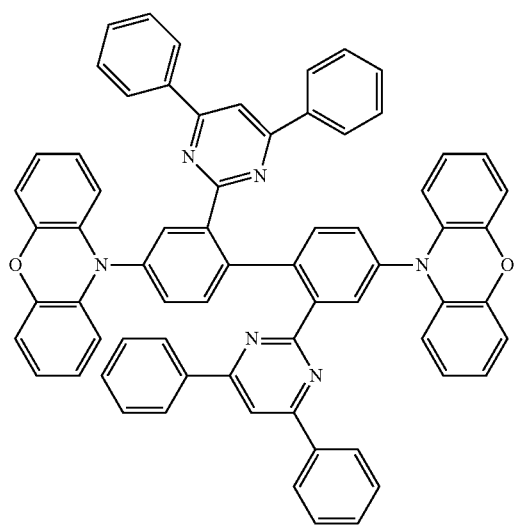
52
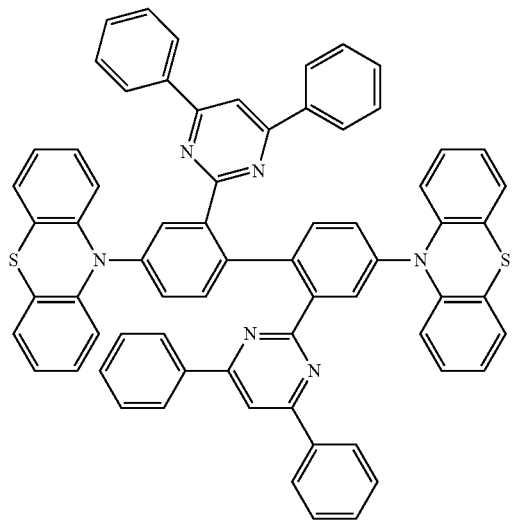
53
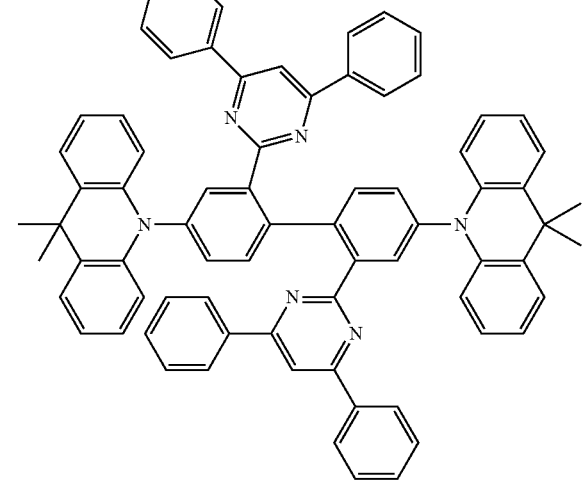
54
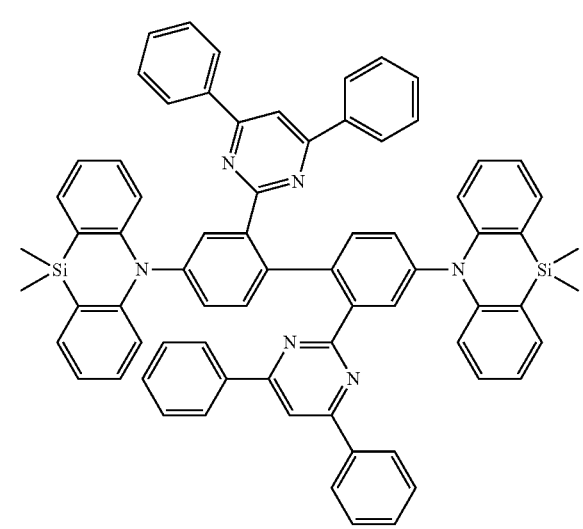

55
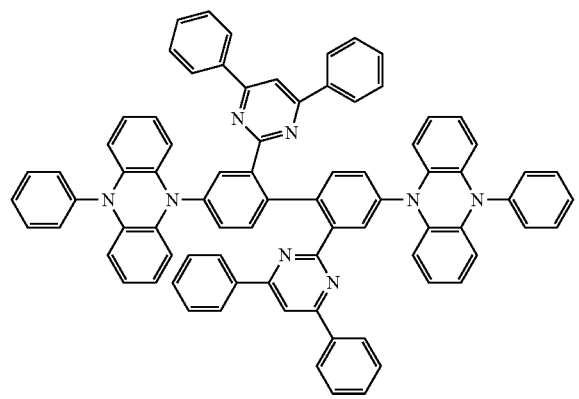
56
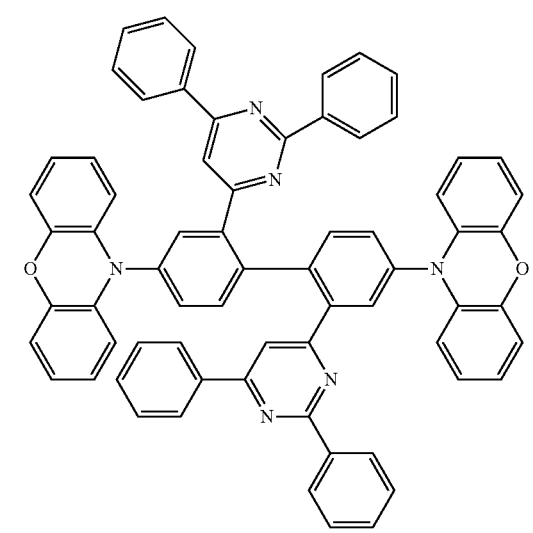
57
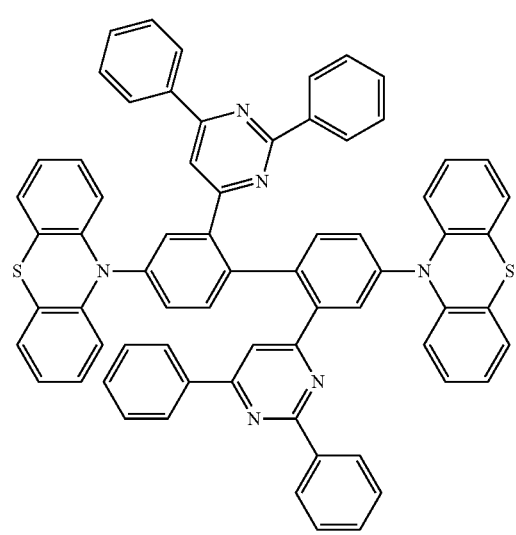
58
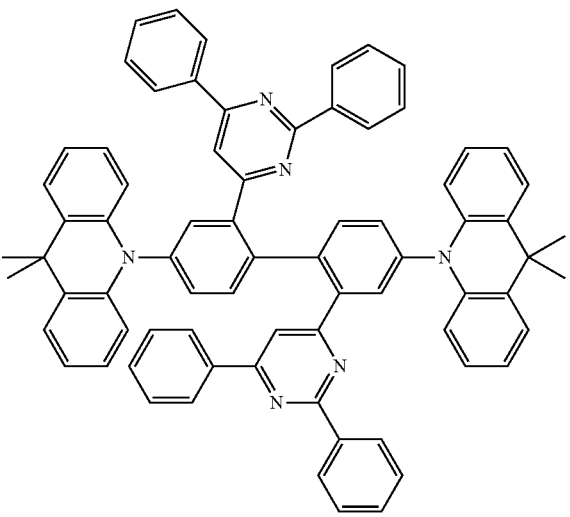
59
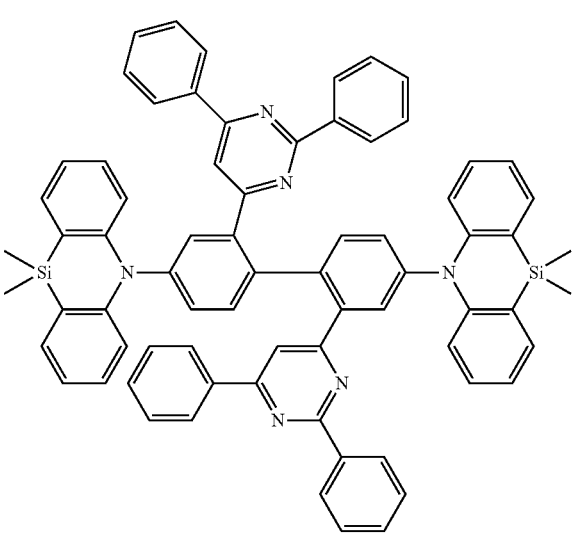
60
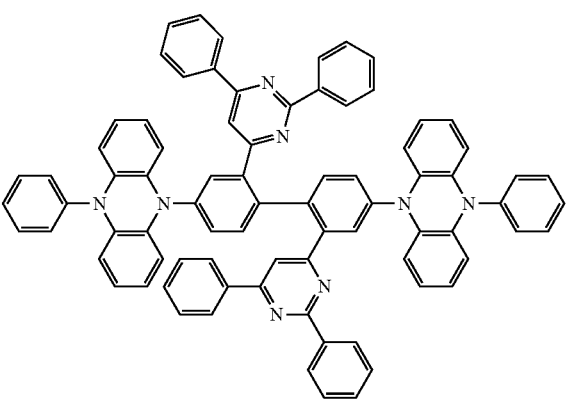

US 10,700,287 B2
29
-continued
61
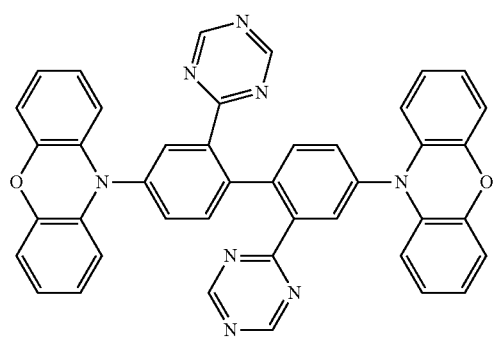
62
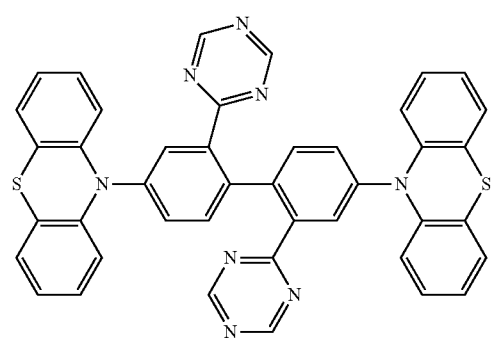
63
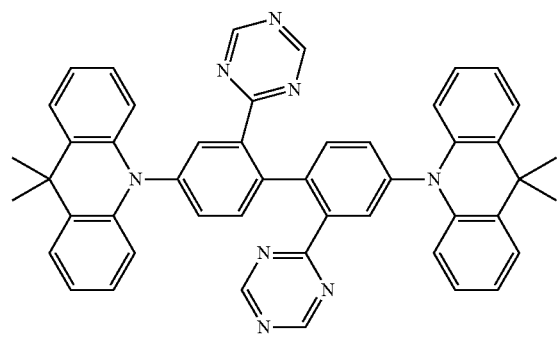
64
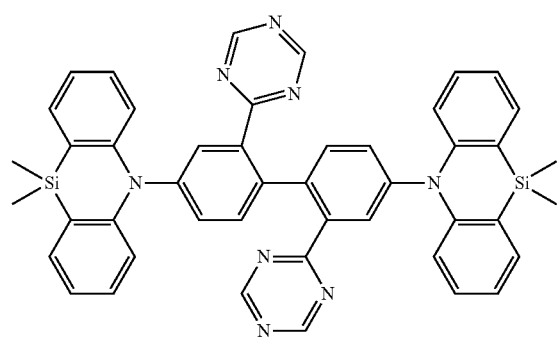
30
-continued
65
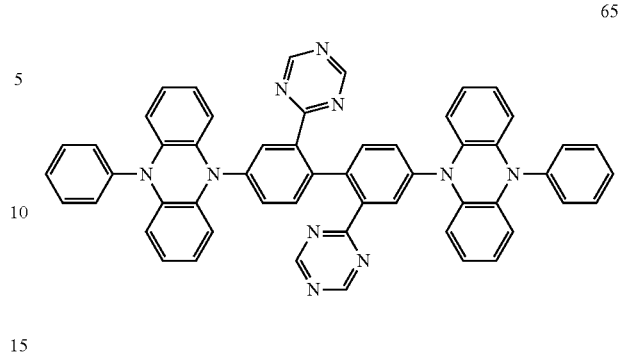
66
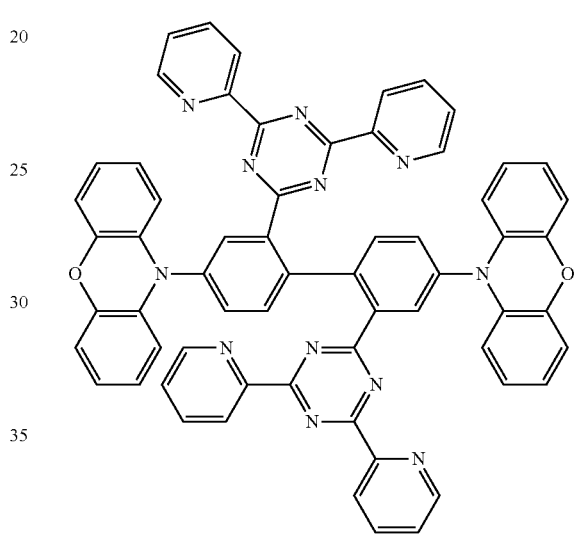
67
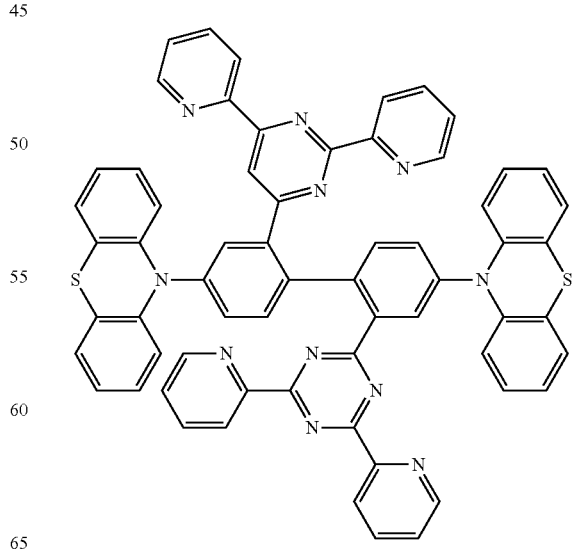

-continued
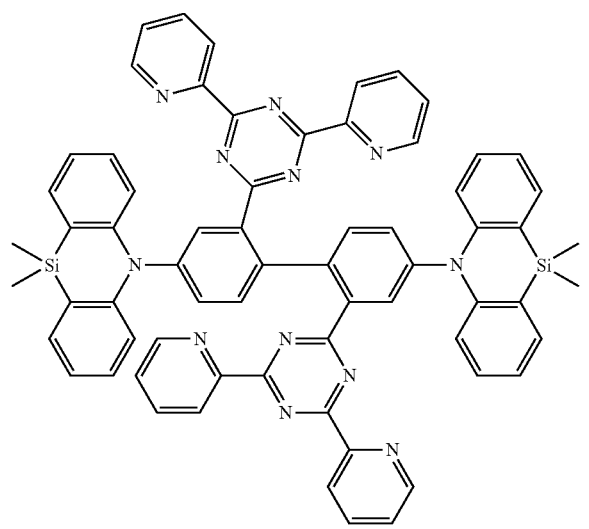
68
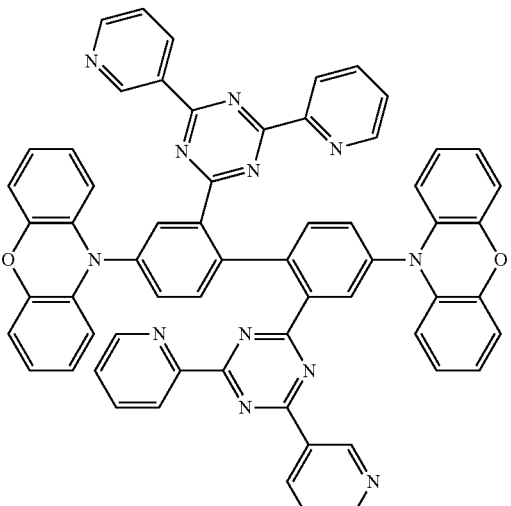
71
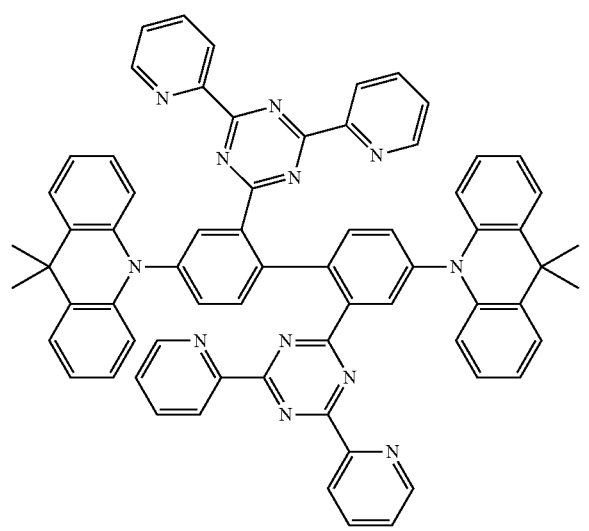
69
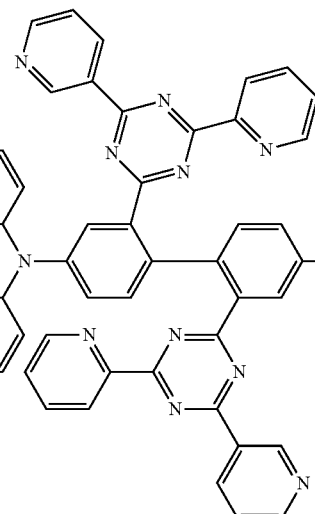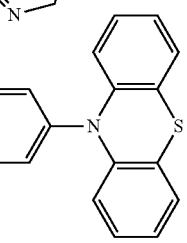
72
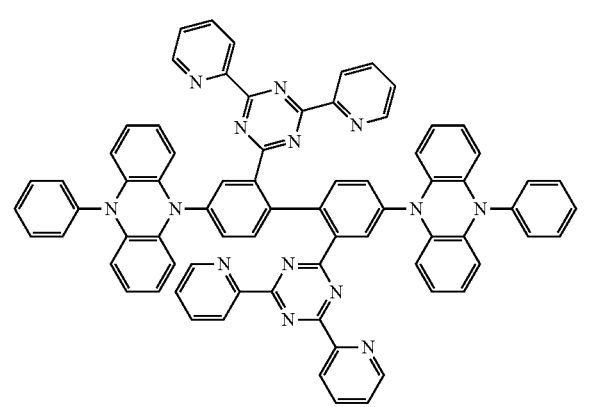
70
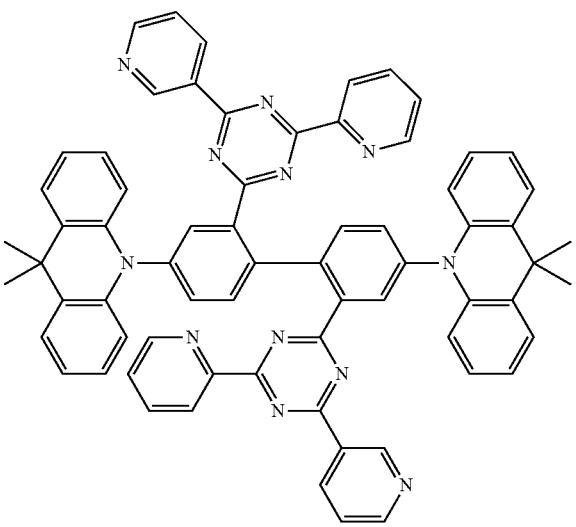
73

74
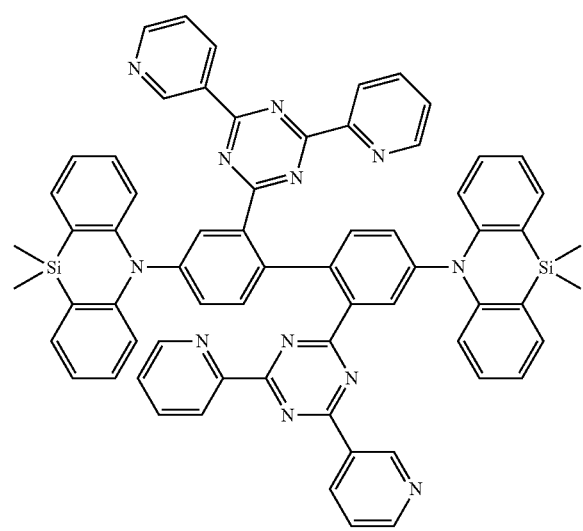
75
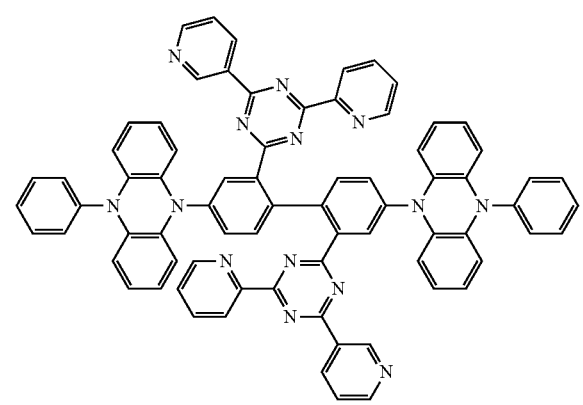
76
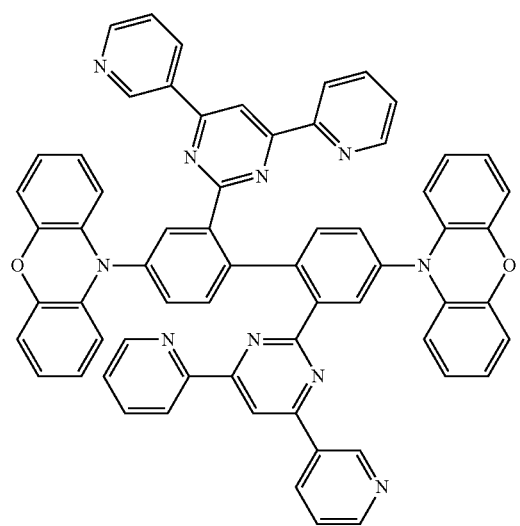
77
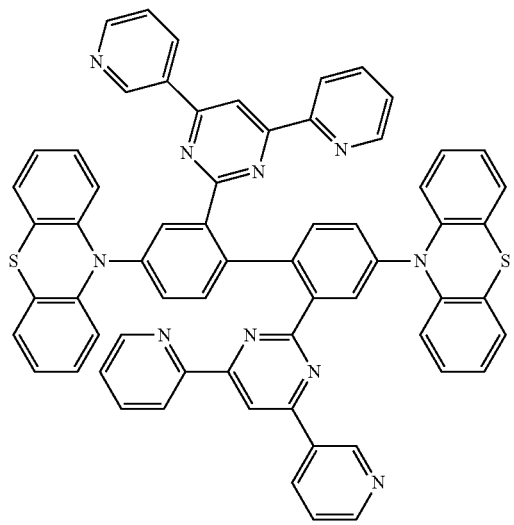
78
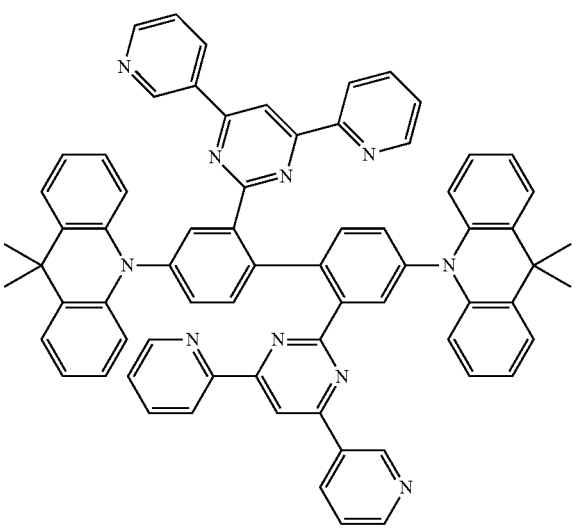
79
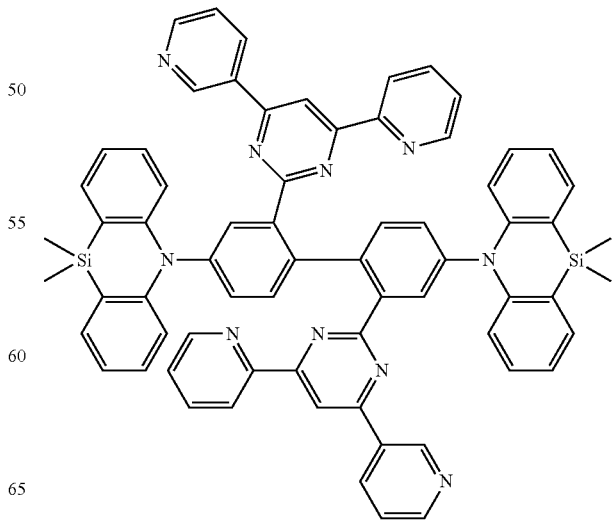

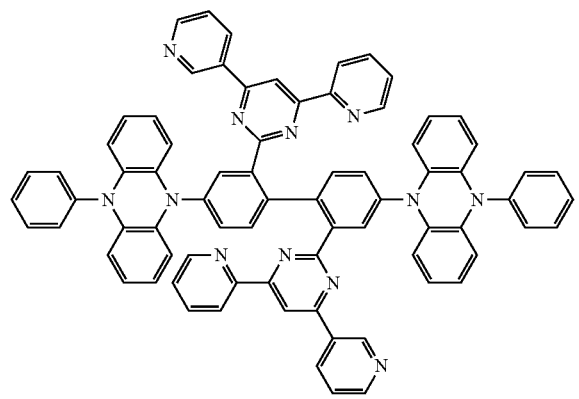
80
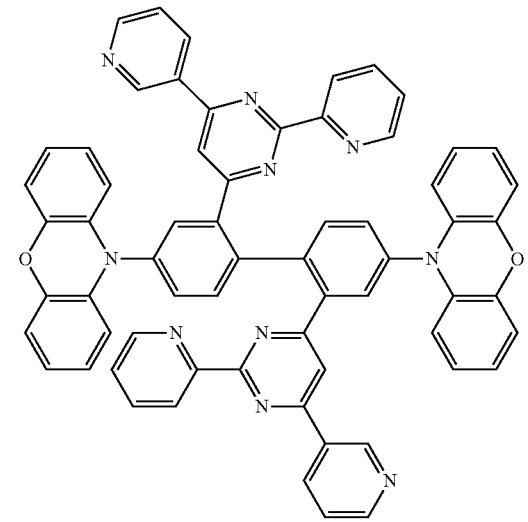
81
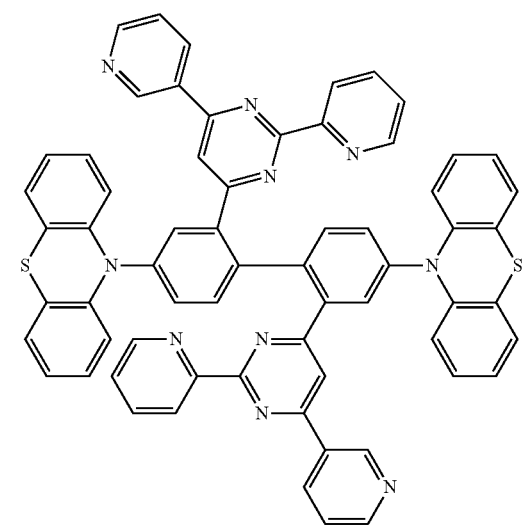
82
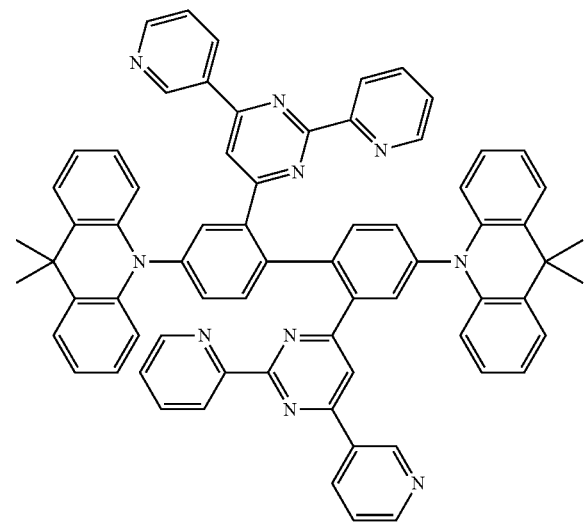
83
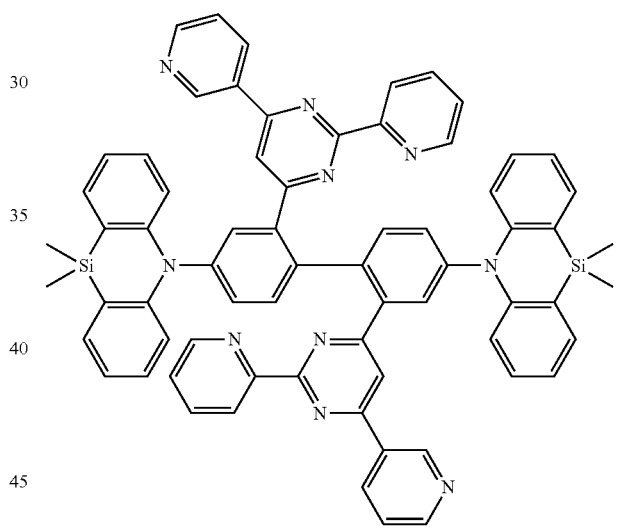
84
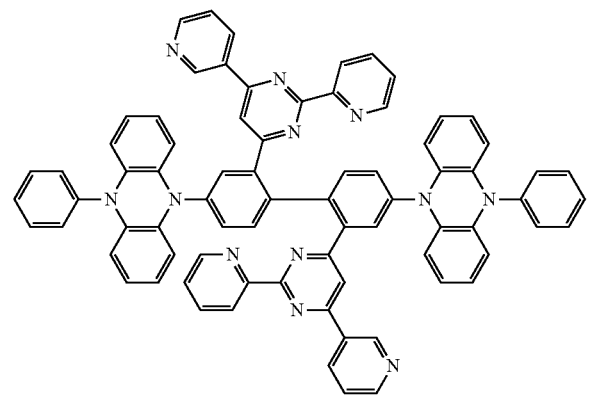
85

-continued
86
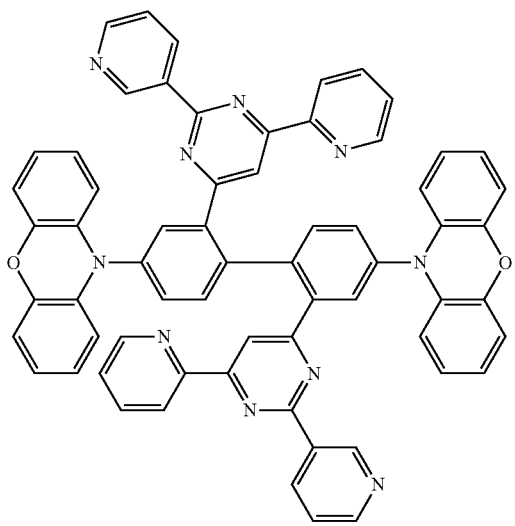
87
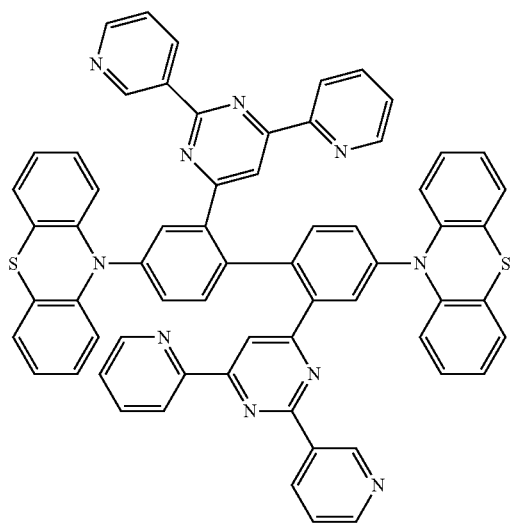
88
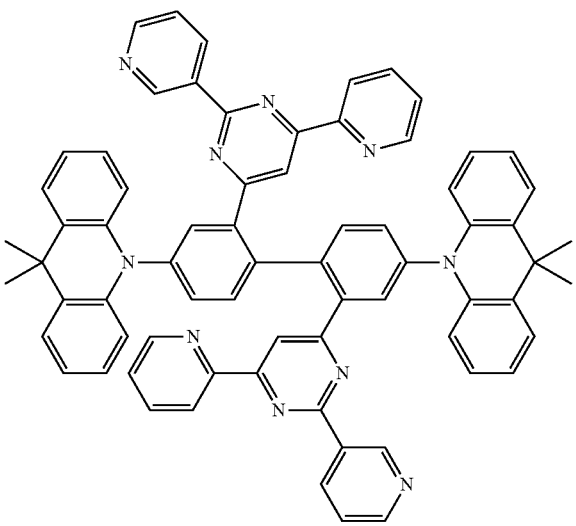
-continued
89
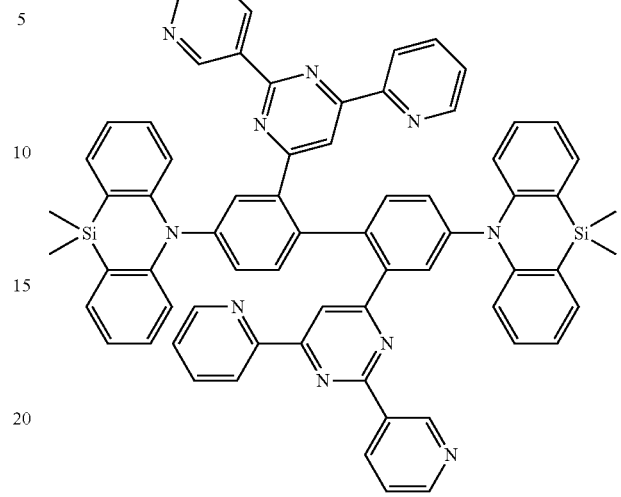
90
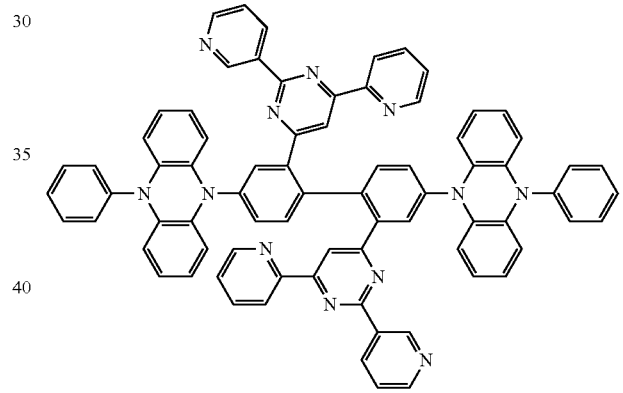
91
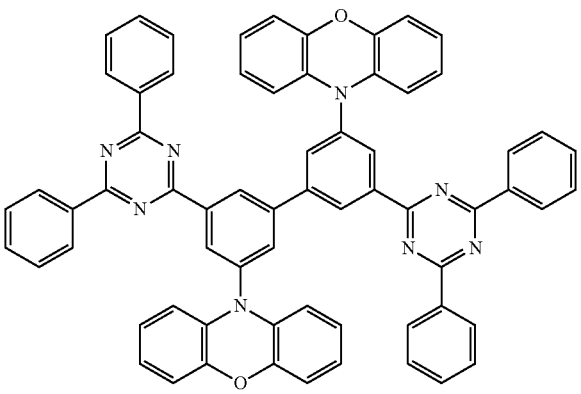

92
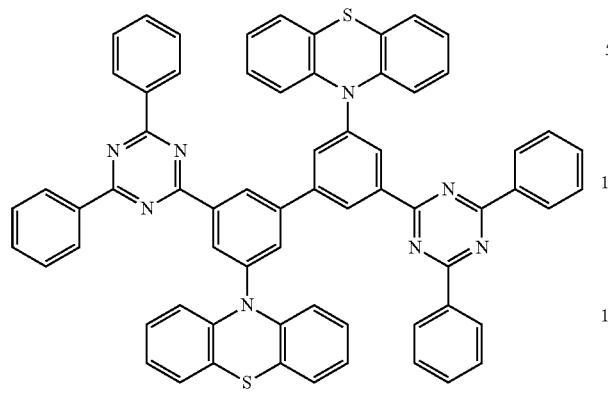
93
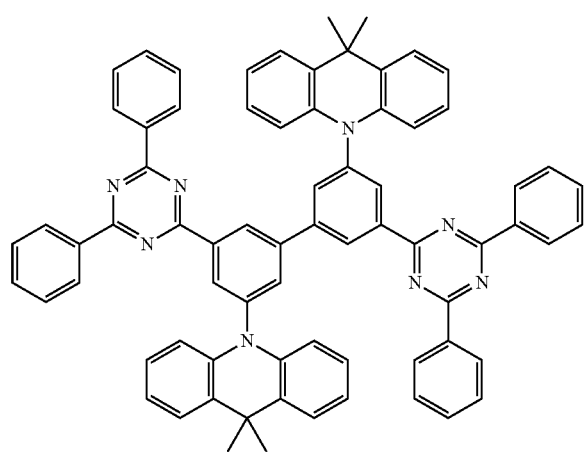
94
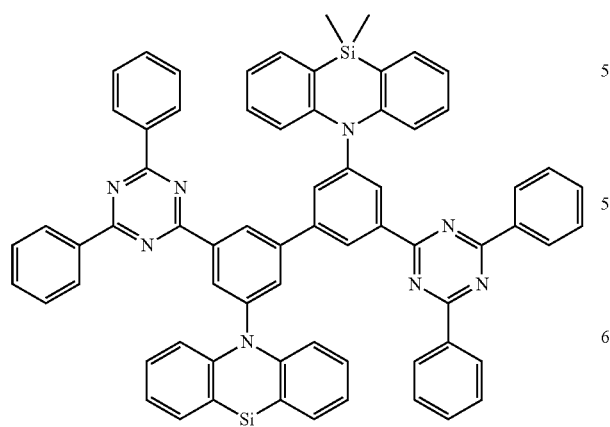
95
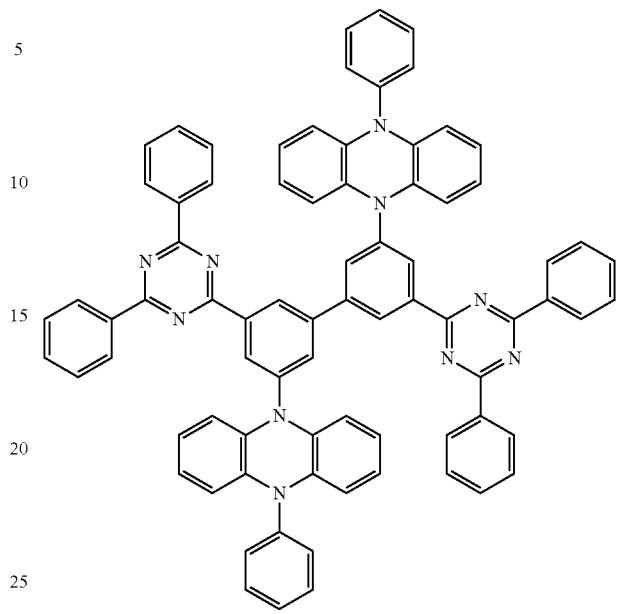
96
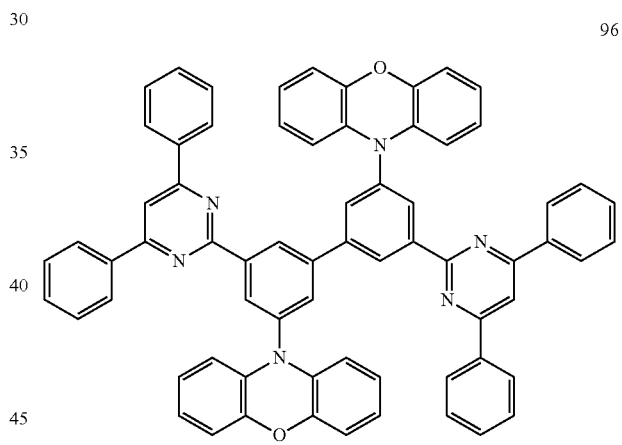
97
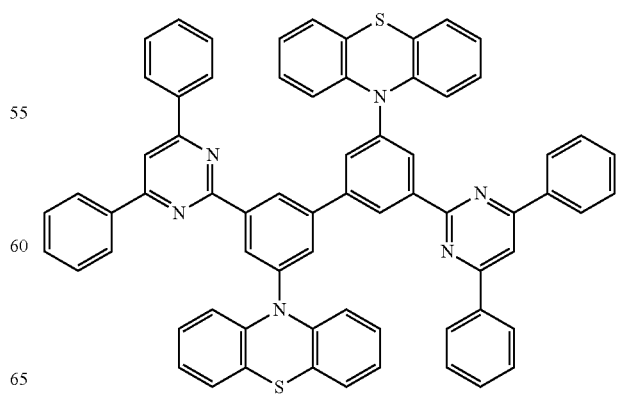

98
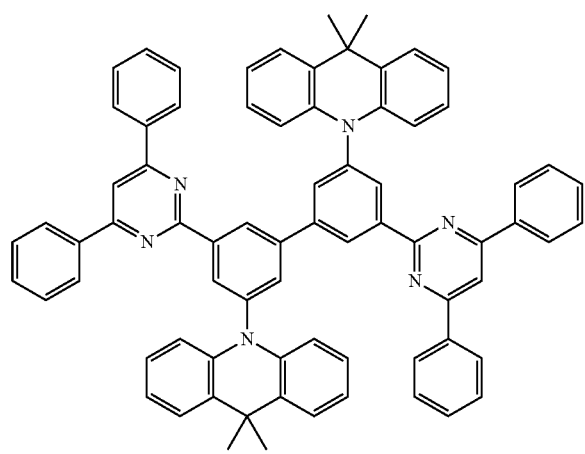
99
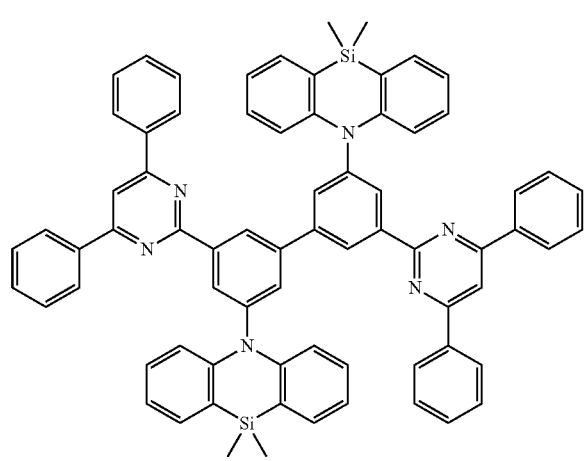
100
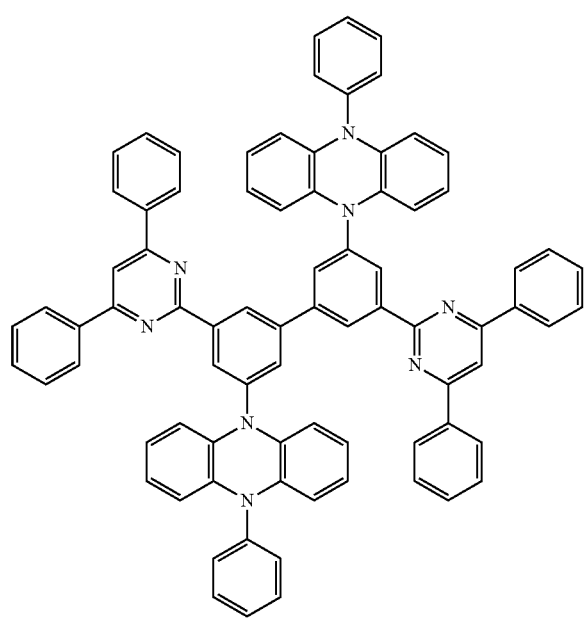
101
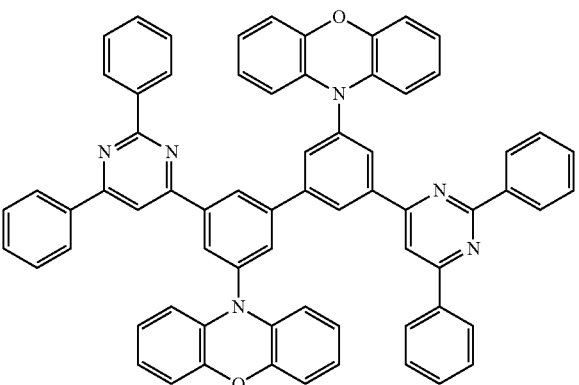
102
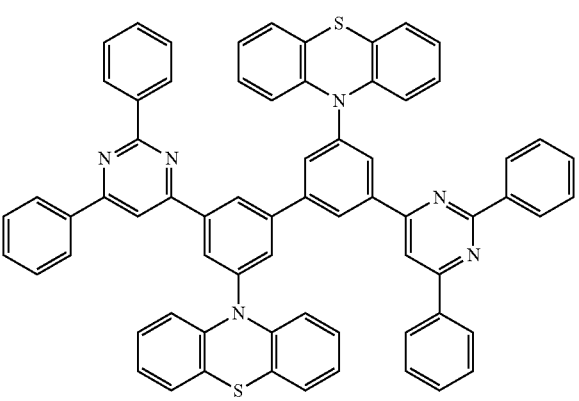
103
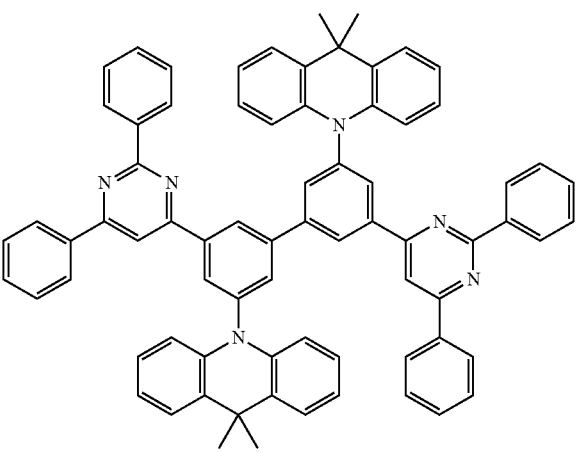

104
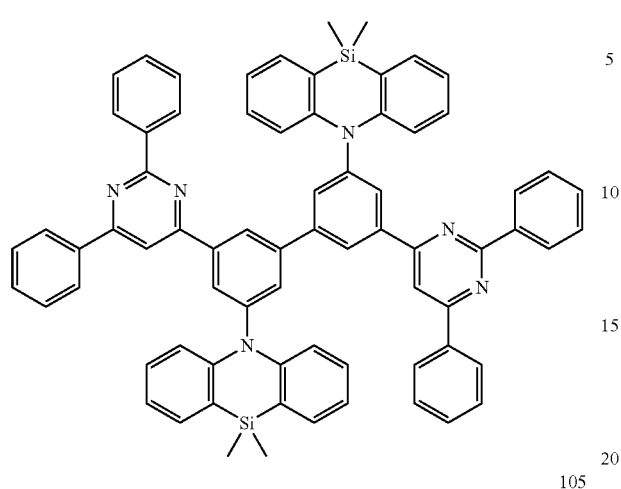
105
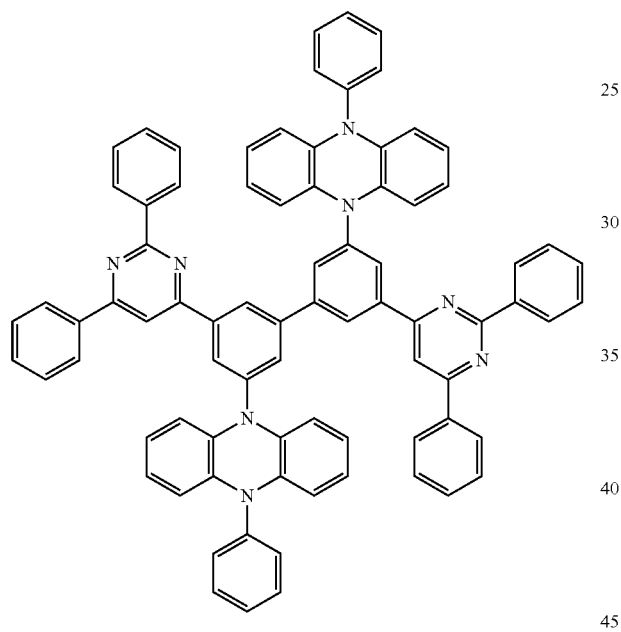
106
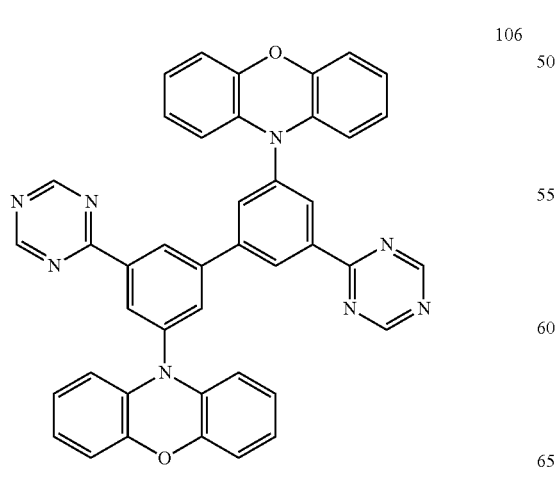
107
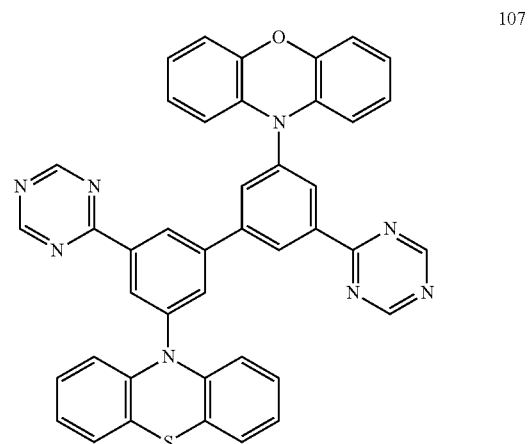
108
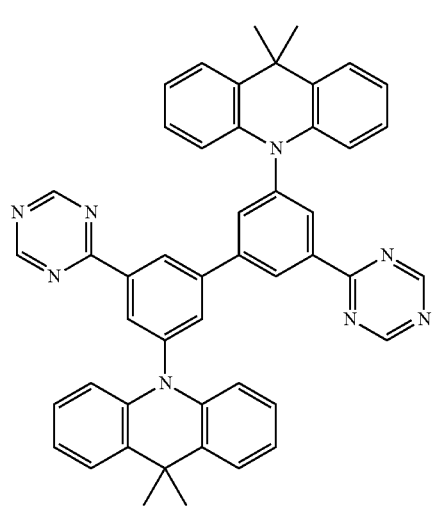
109
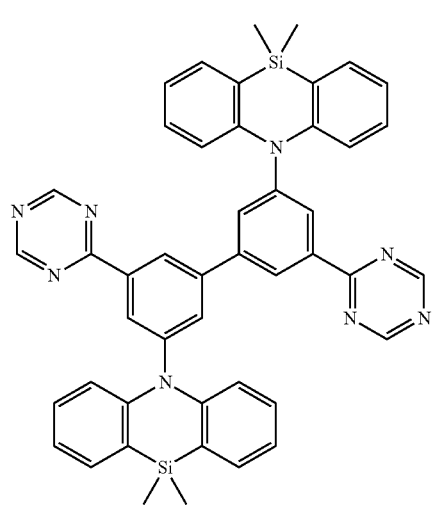

110
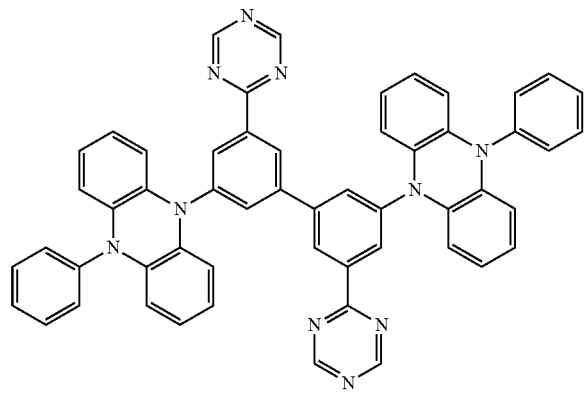
111
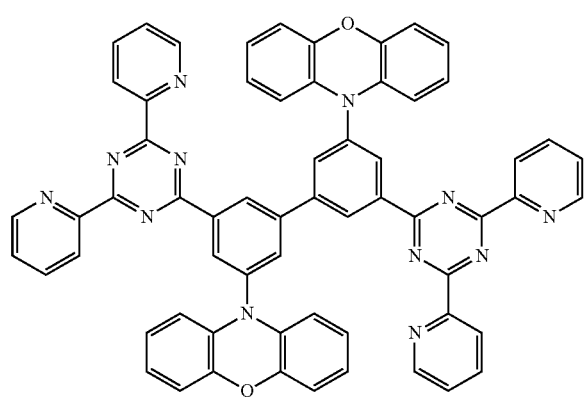
112
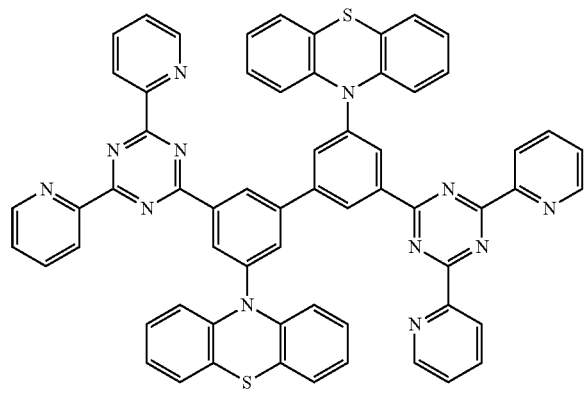
113
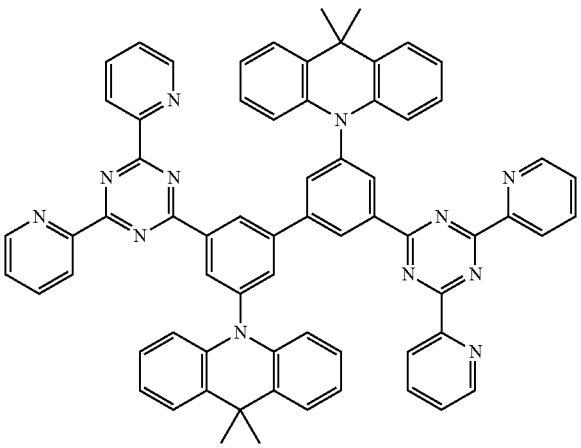
114
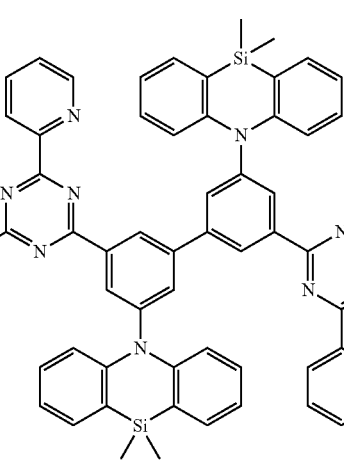
115
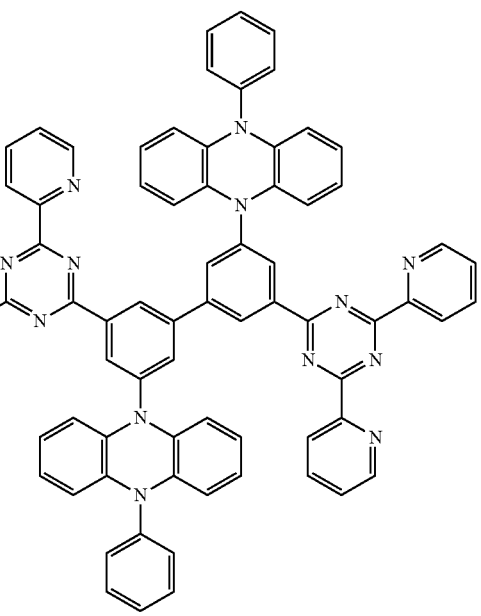

116
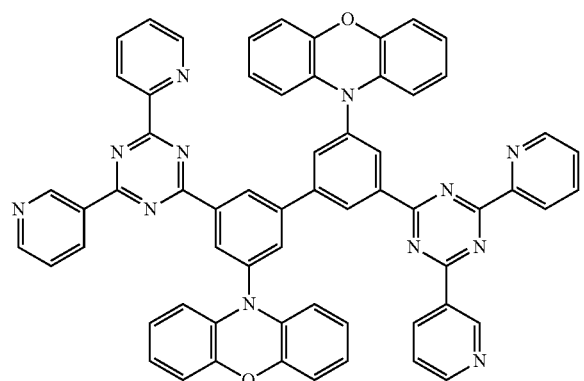
117
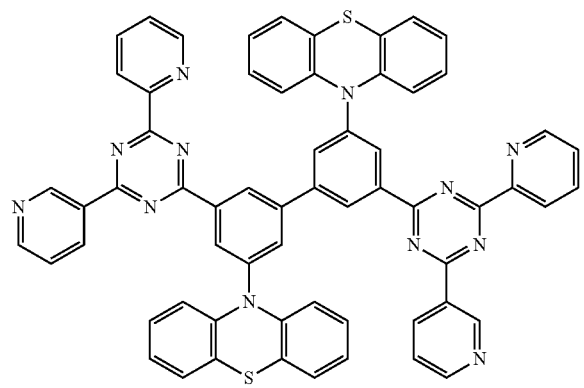
118
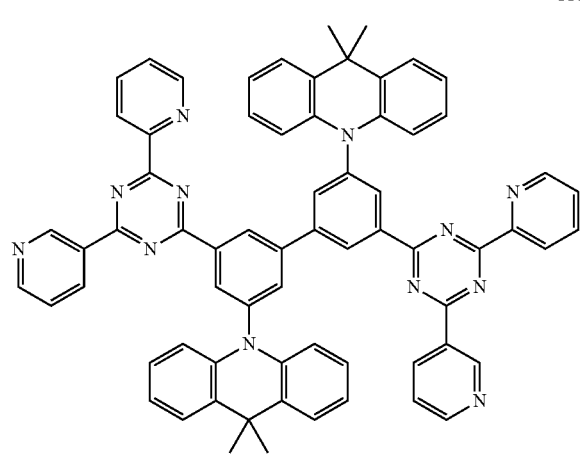
119
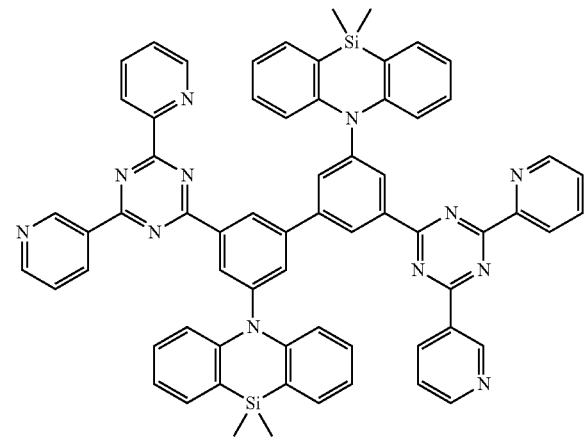
120
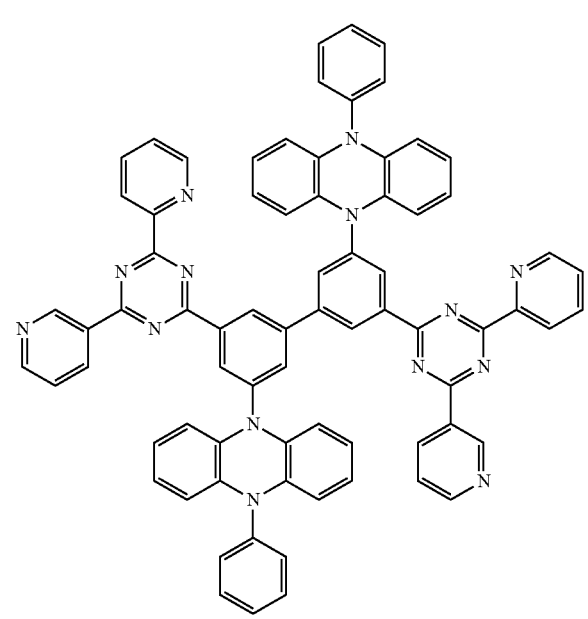
121
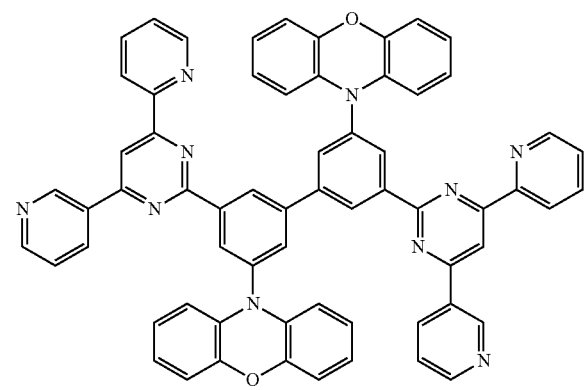

122
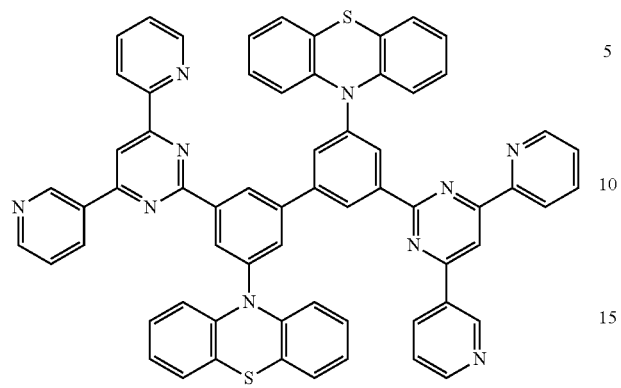
123
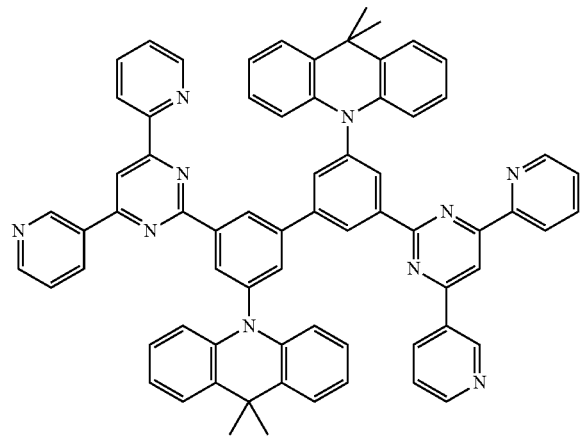
124
125
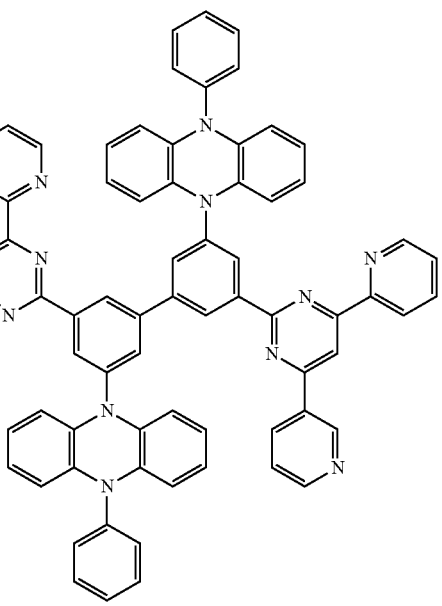
126
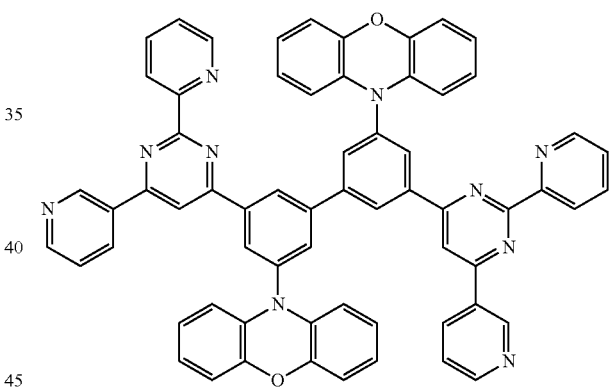
127
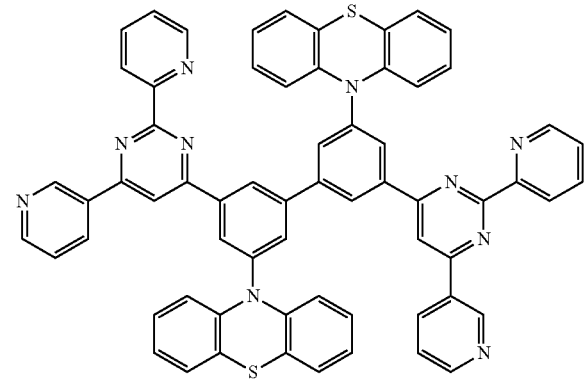

128
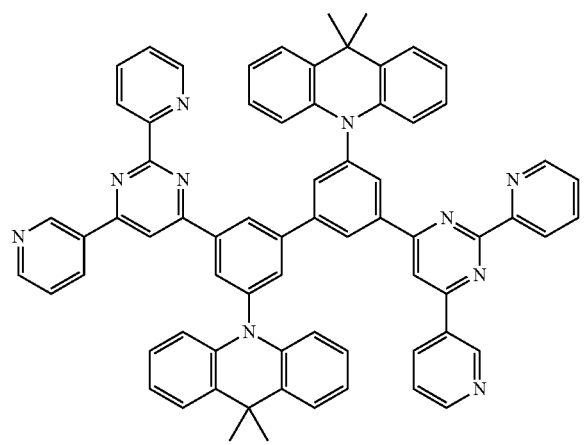
129
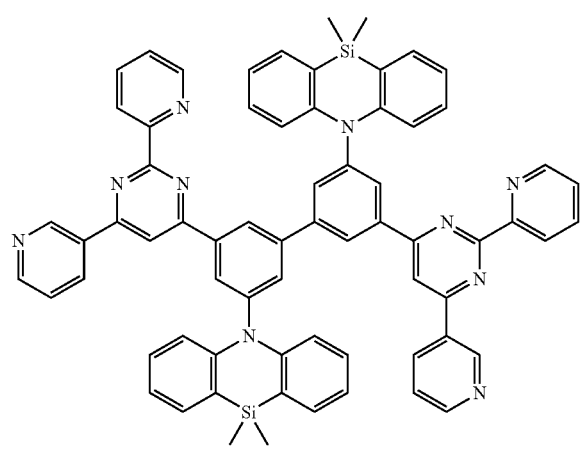
130
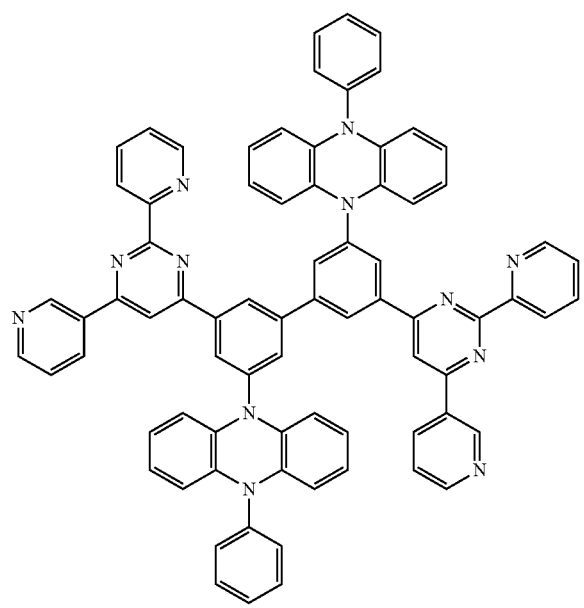
131
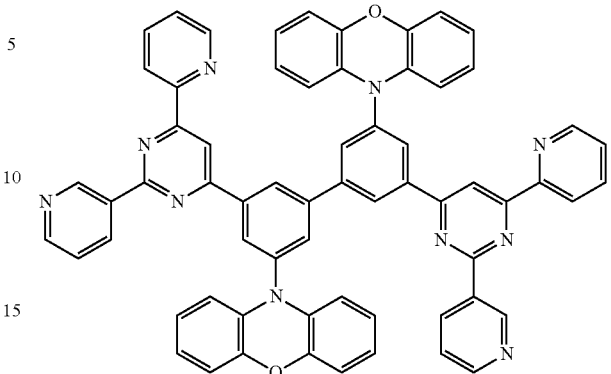
132
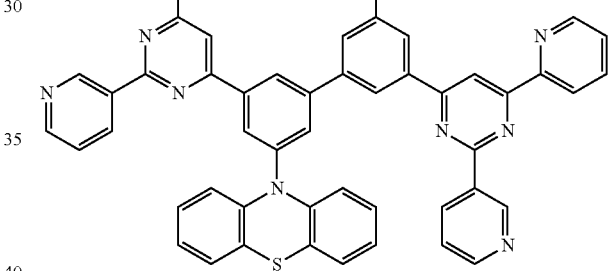
133
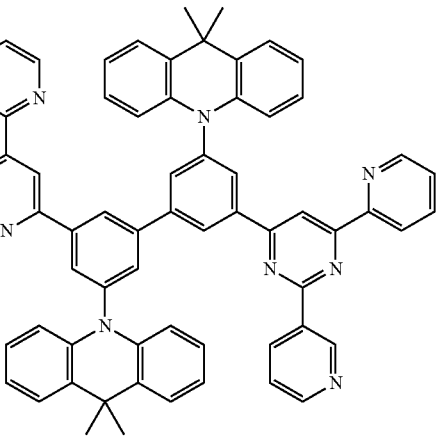

134
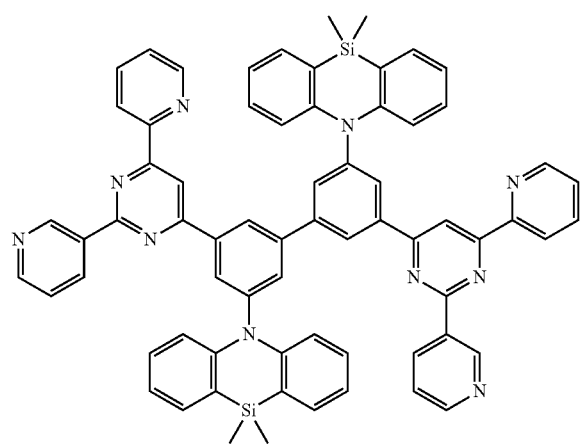
135
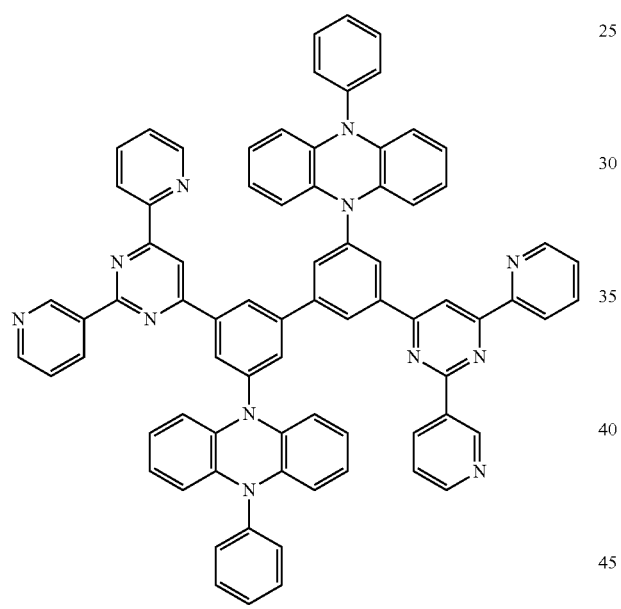
136
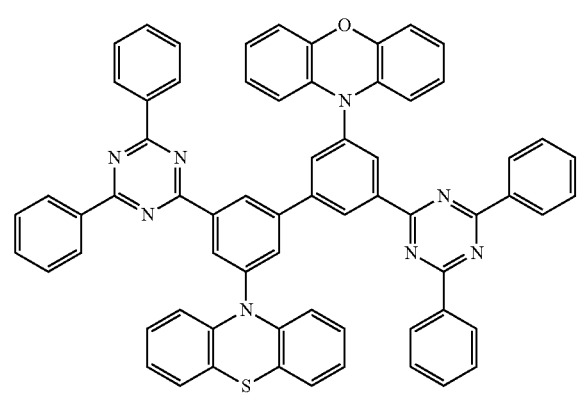
137
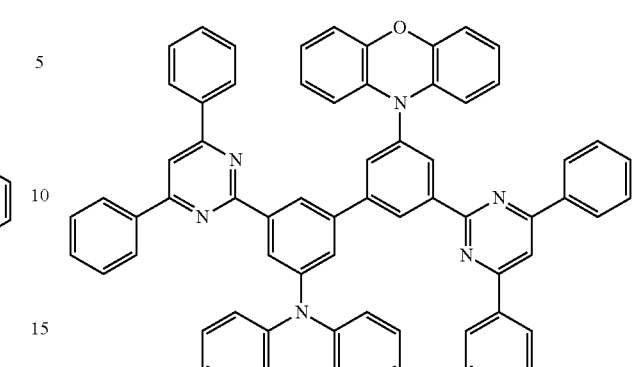
138
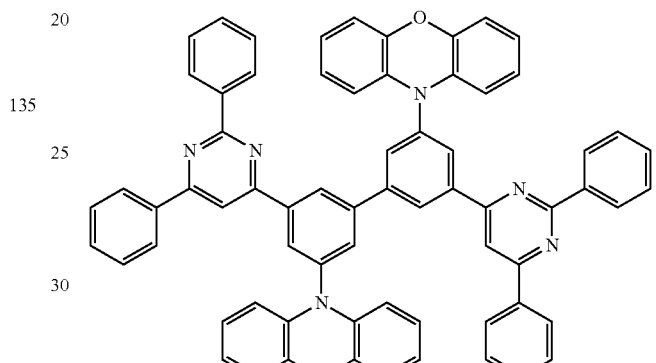
139
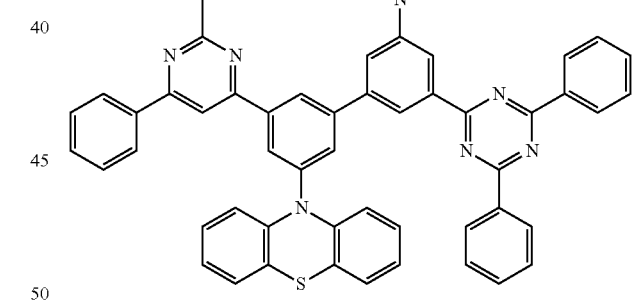
140
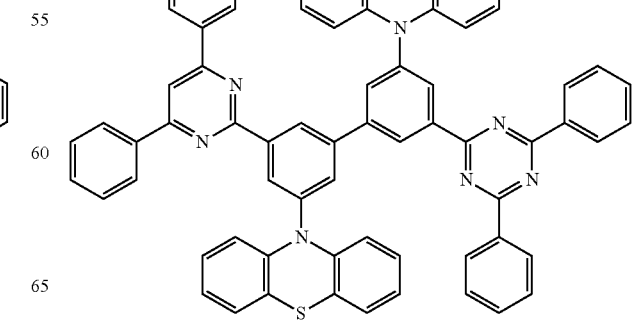

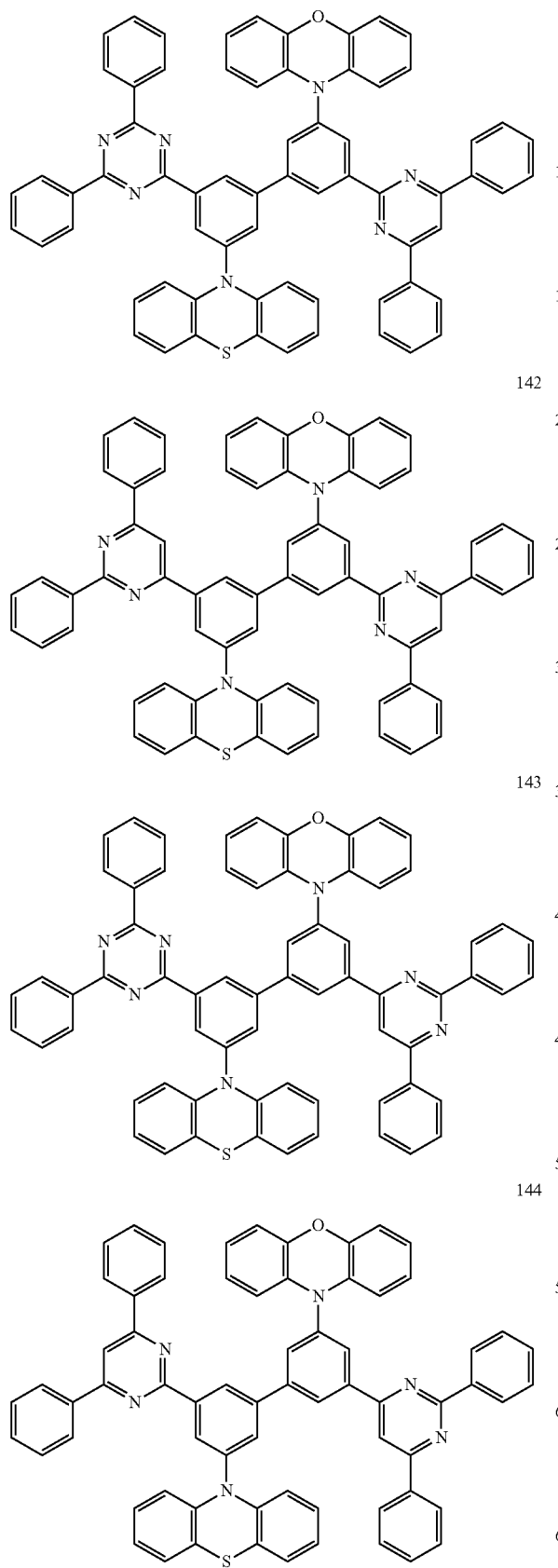
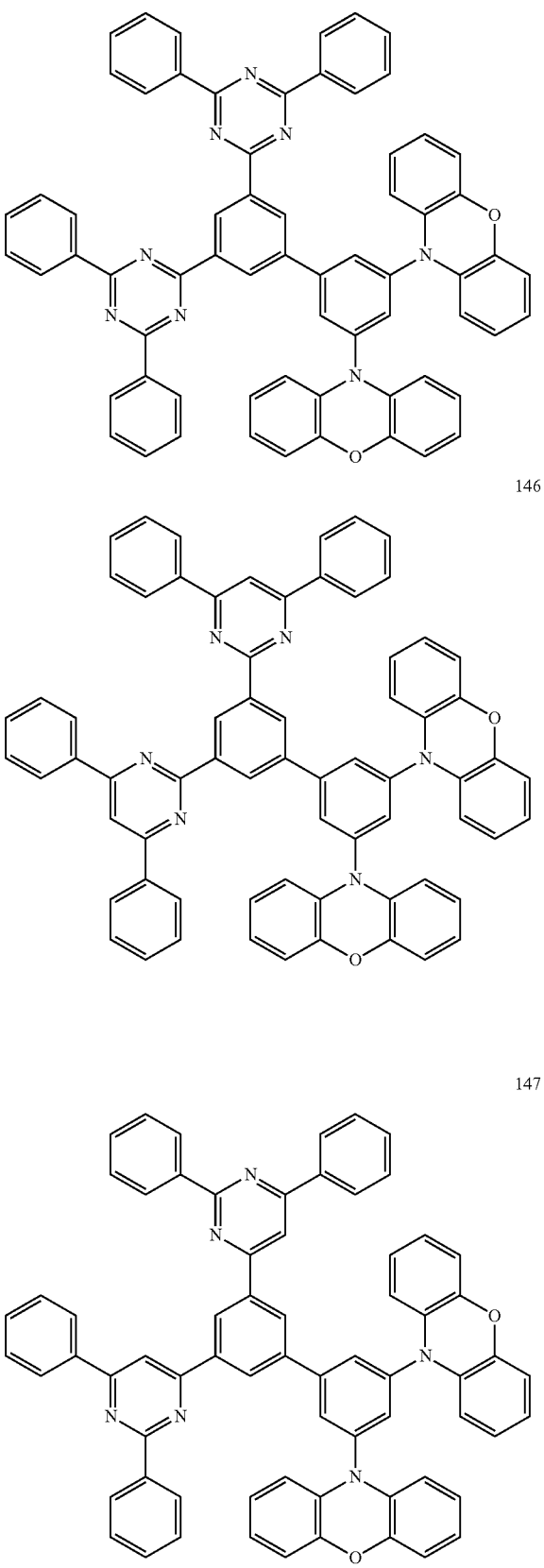

148
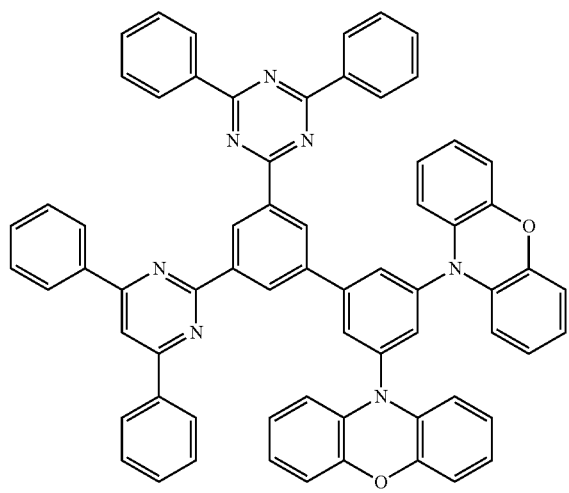
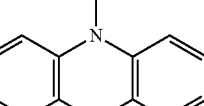
151
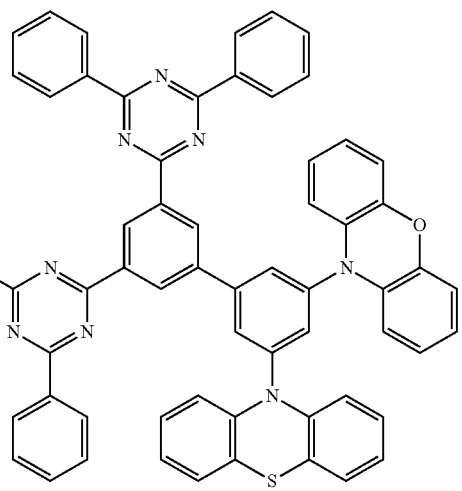
149
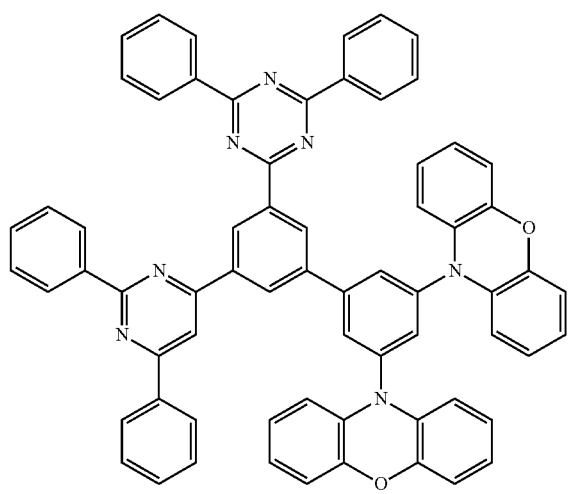
152
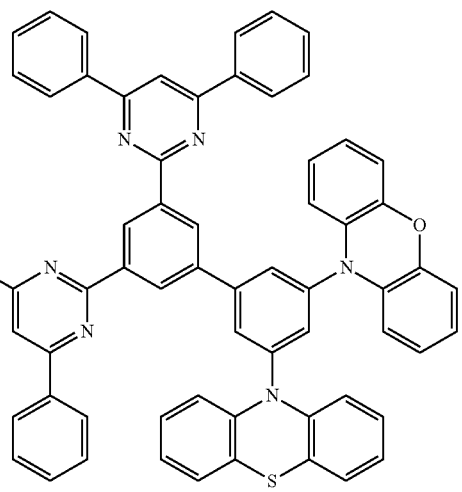
150
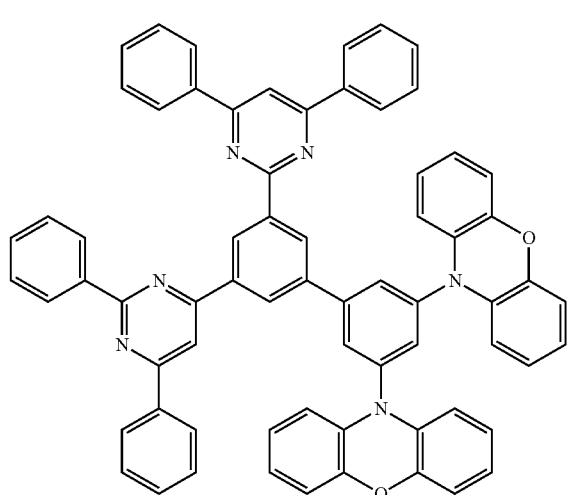
153
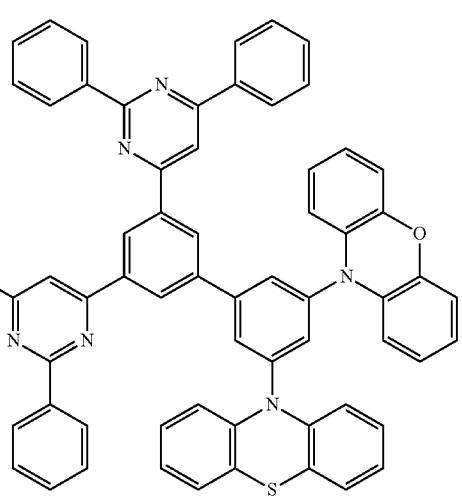

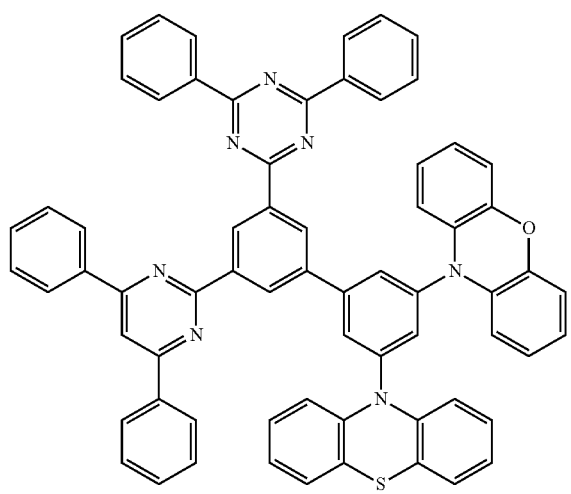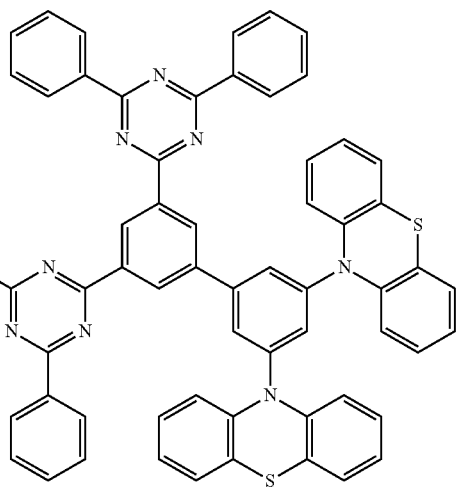

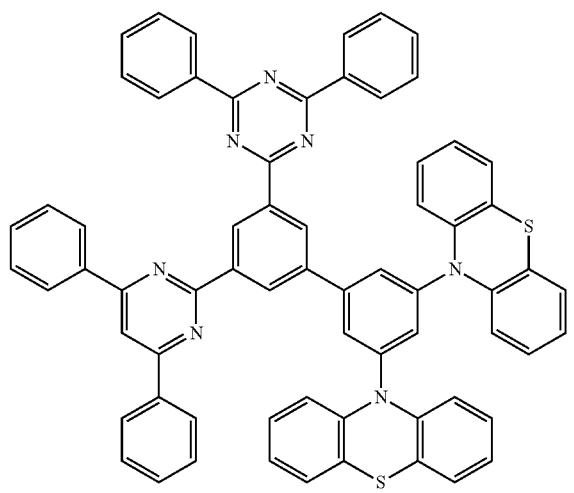
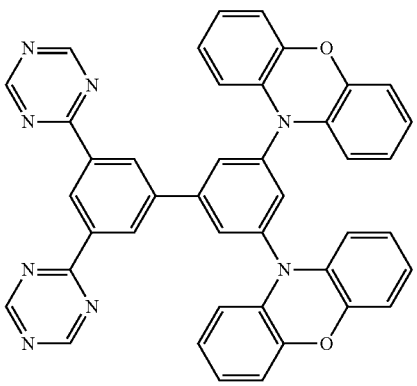
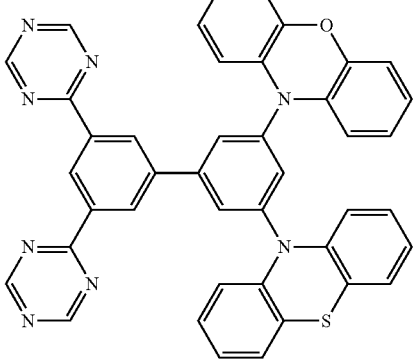
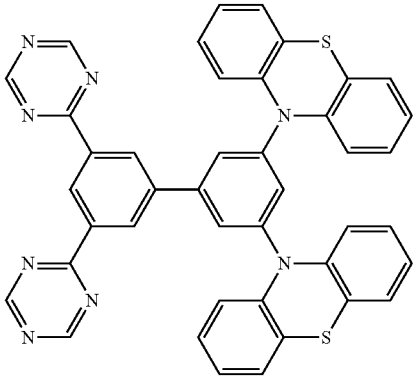
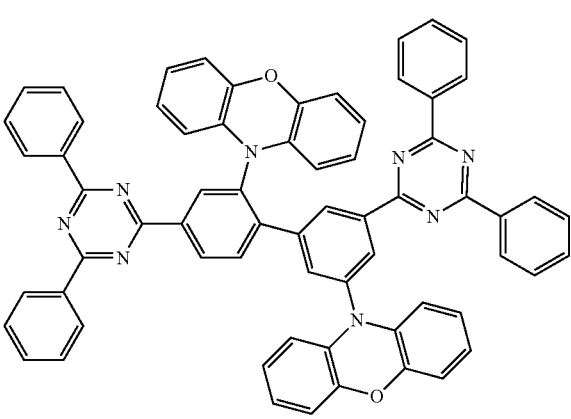

167
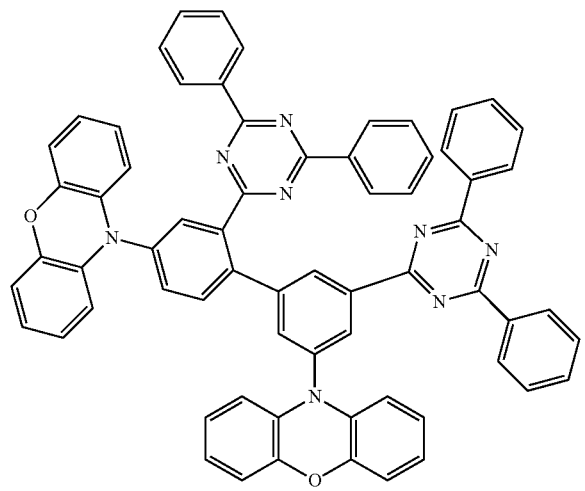
168
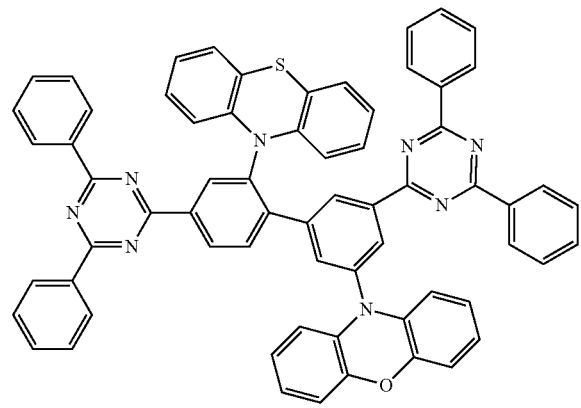
169
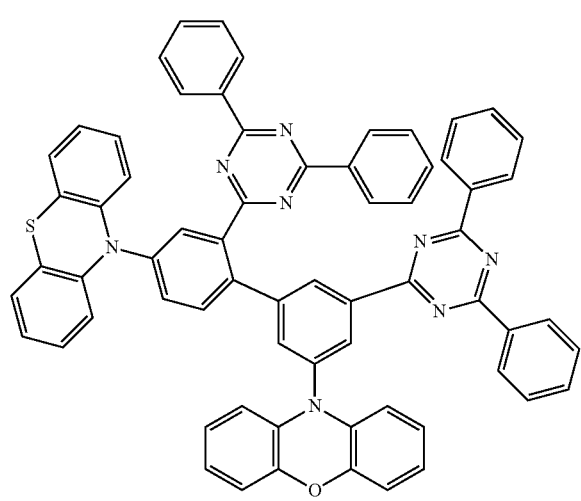
170
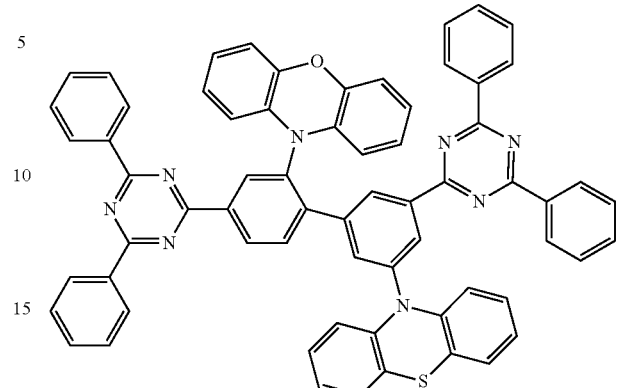
171
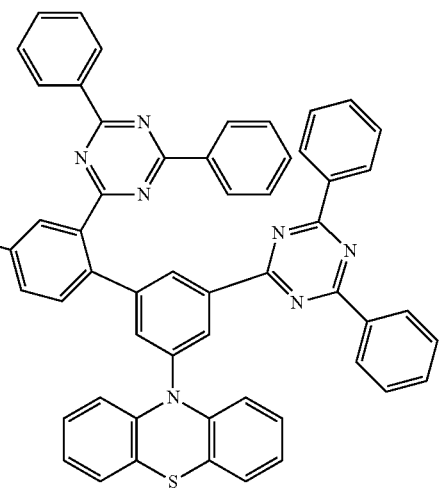
172
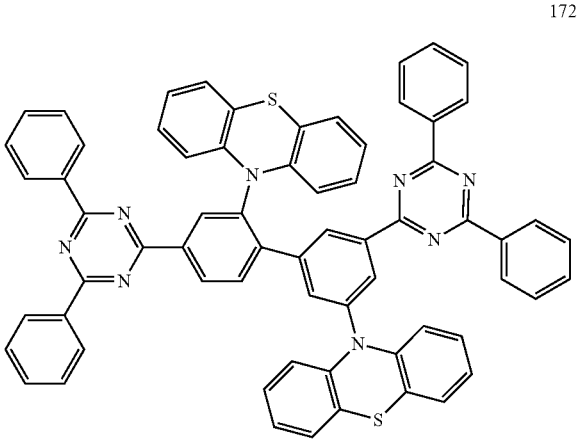

173
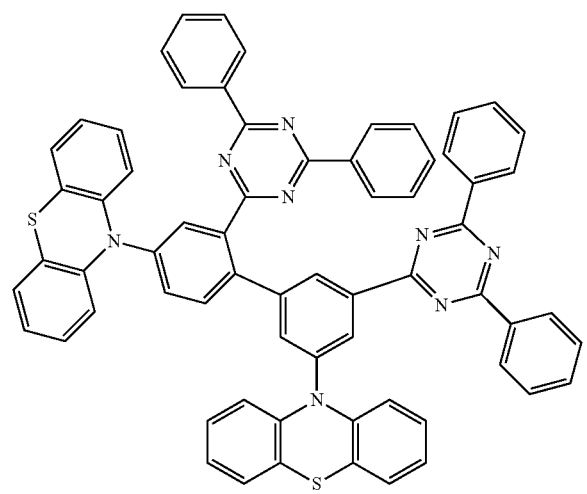
174
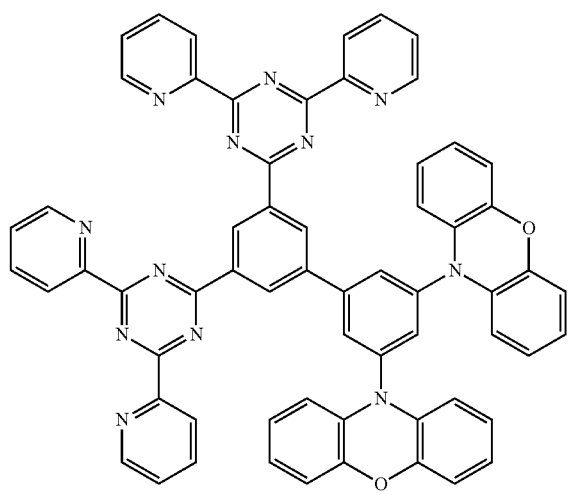
175
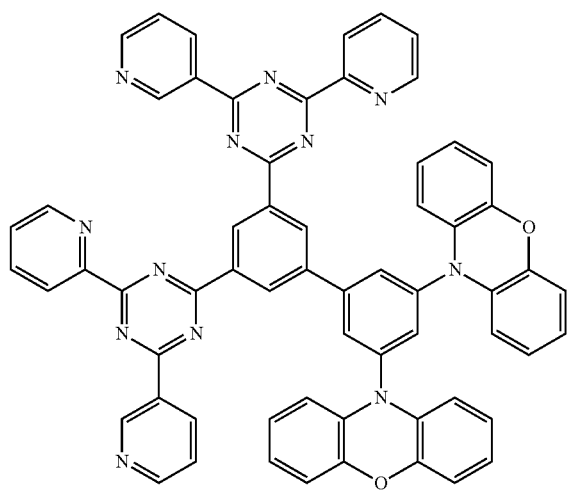
176
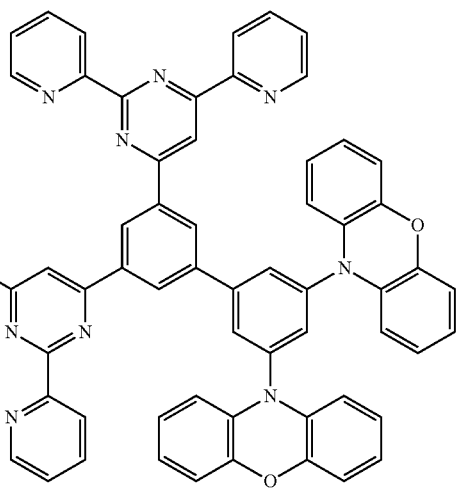
177
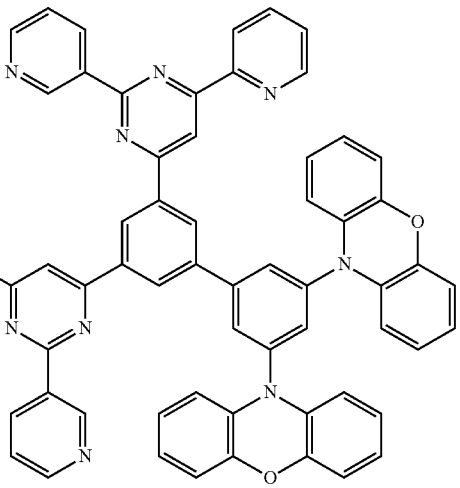
178
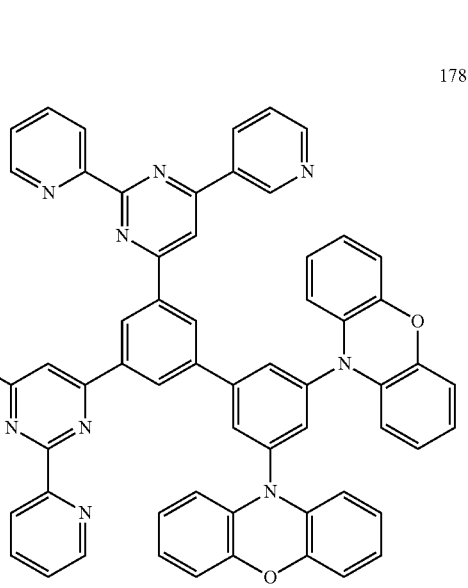

179
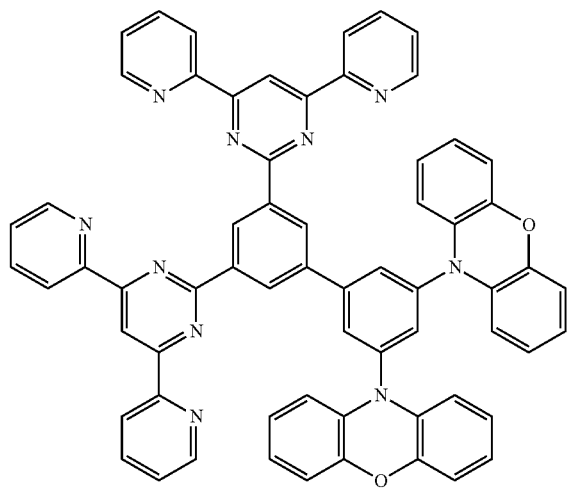
180
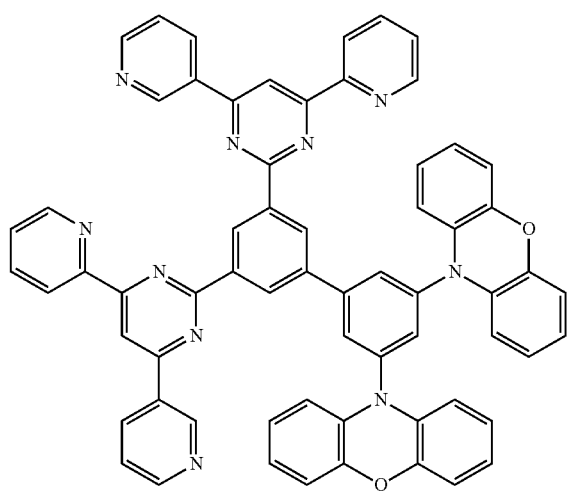
181
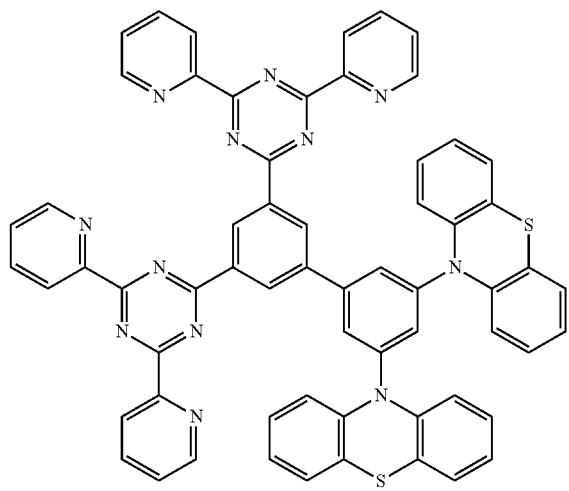
182
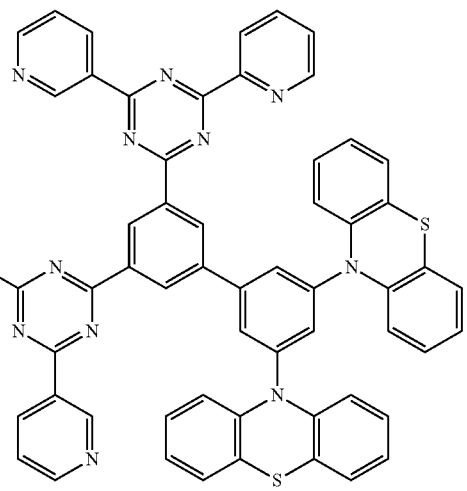
183
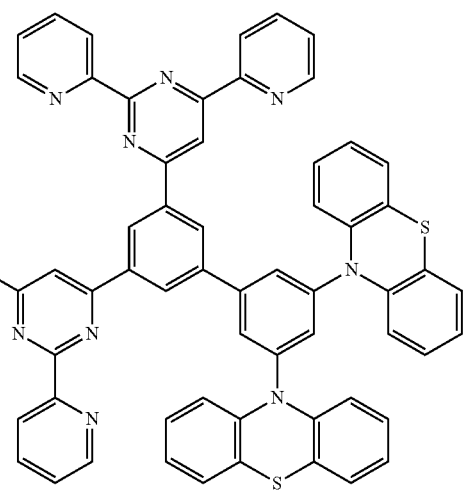
184
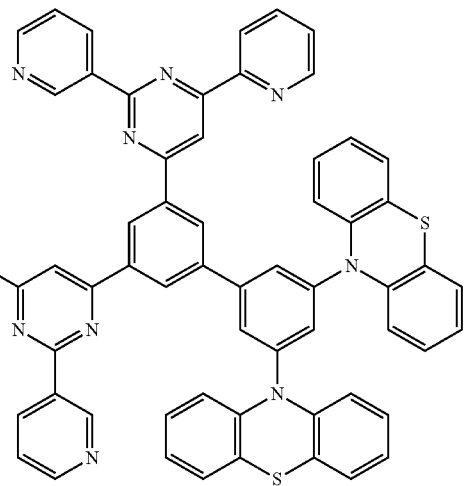

185
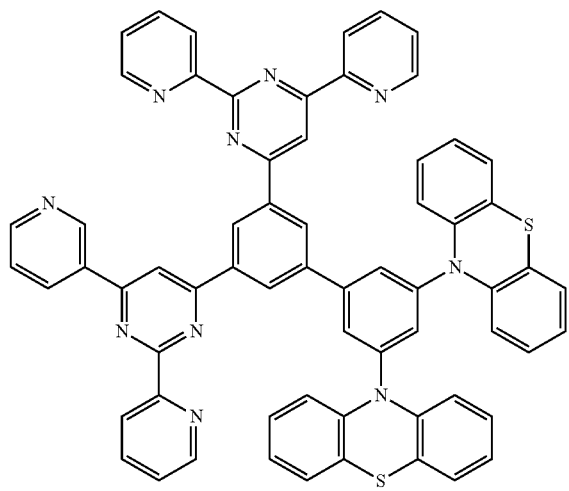
186
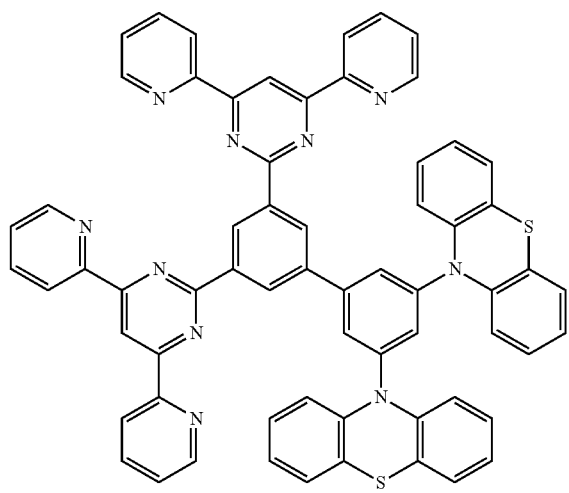
187
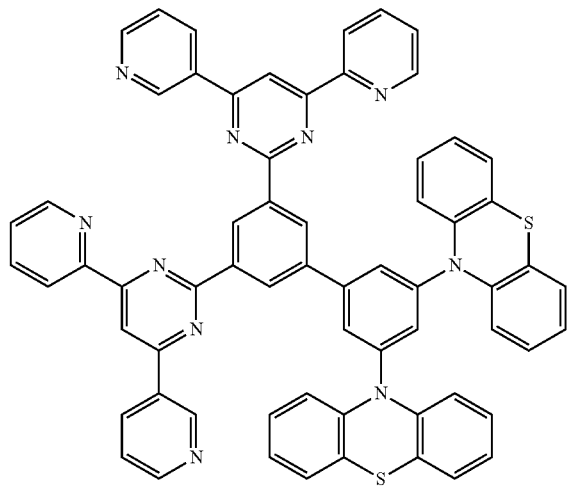
188
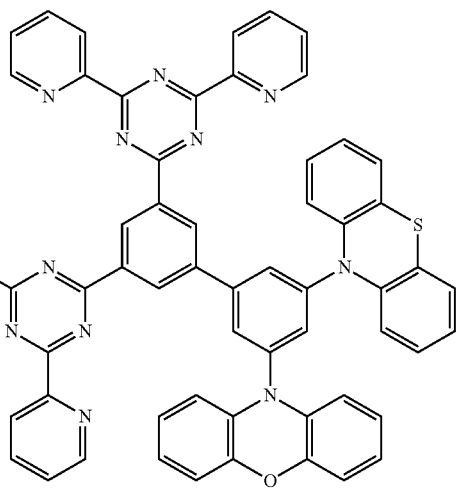
189
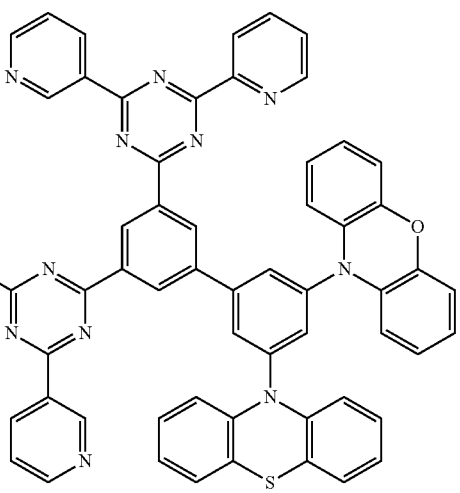
190
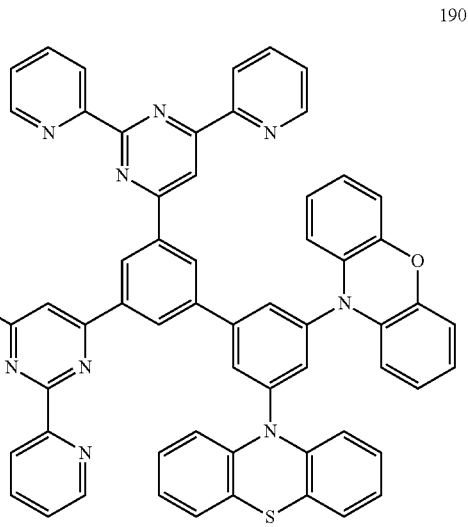

-continued
191
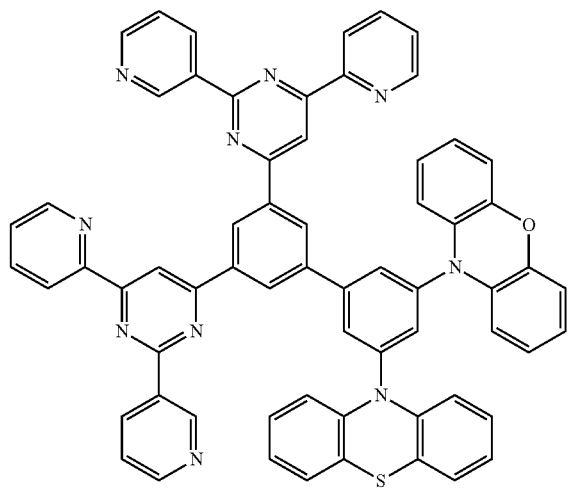
192
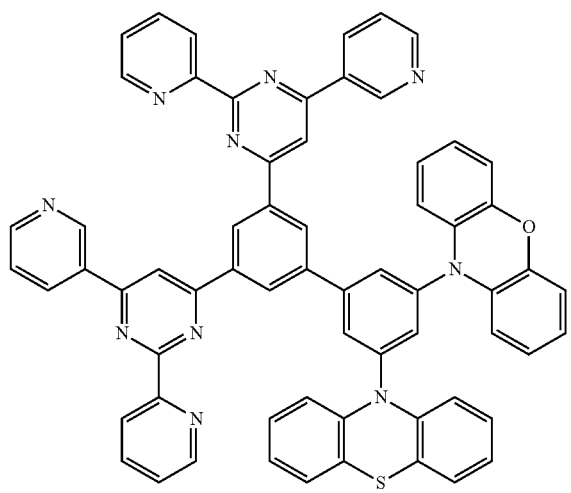
193
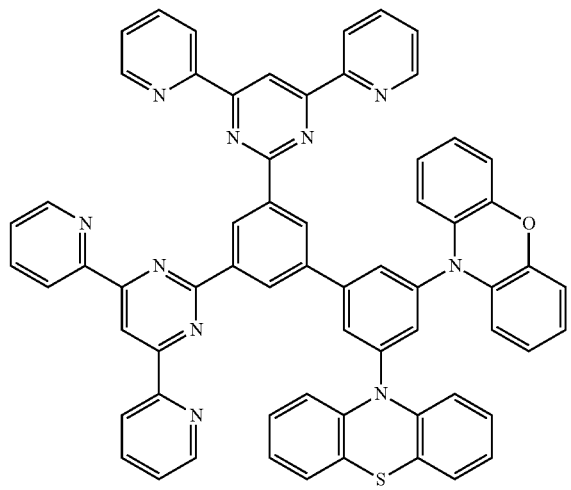
-continued
194
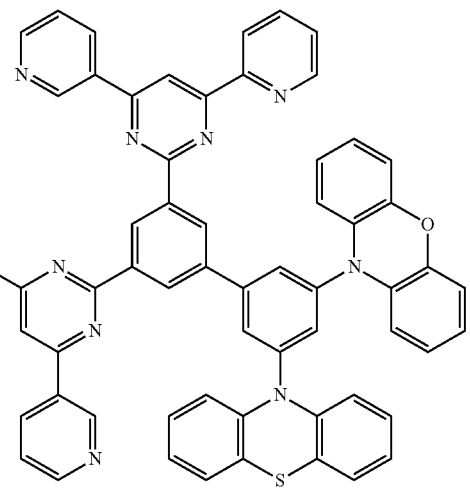
195
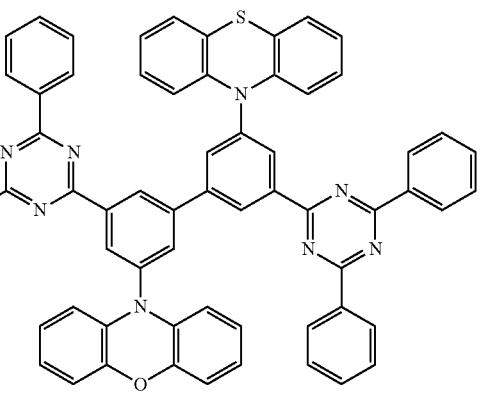
196
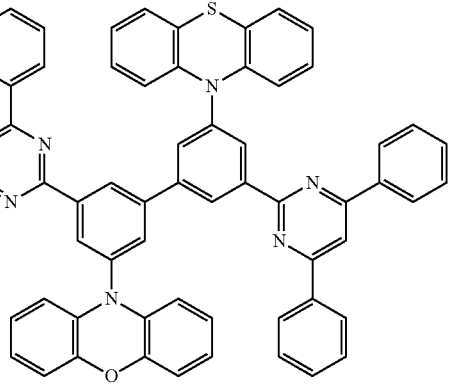

197
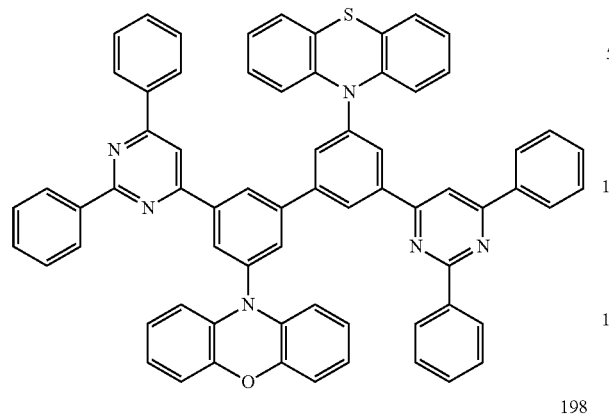
198
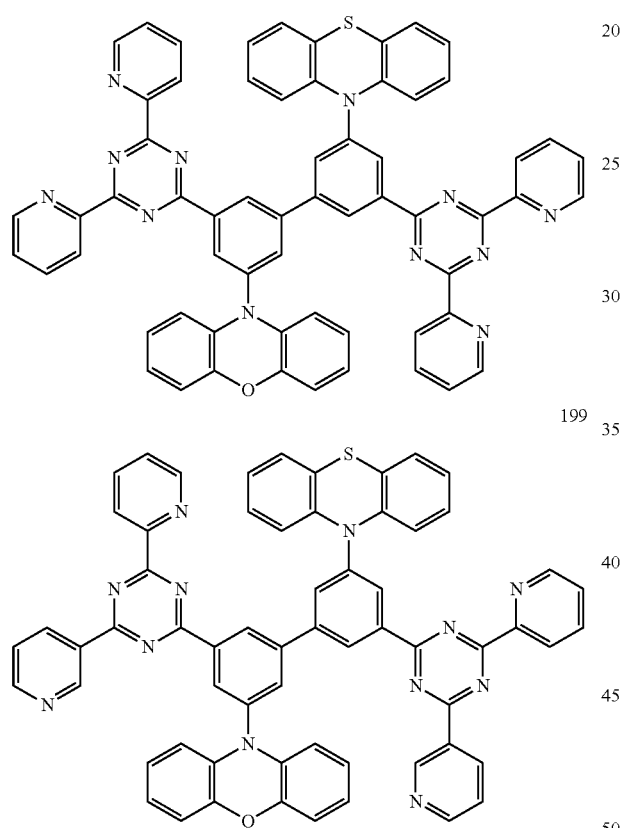
199
200
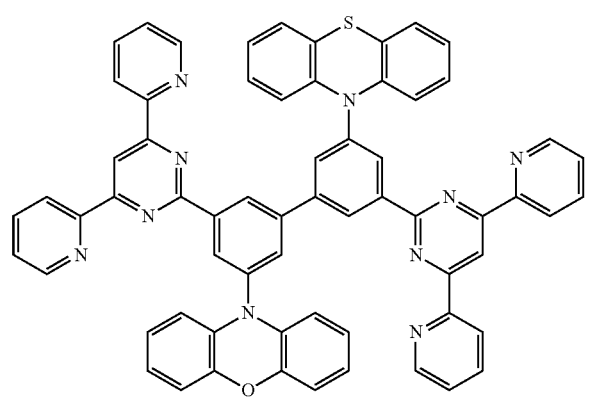
201
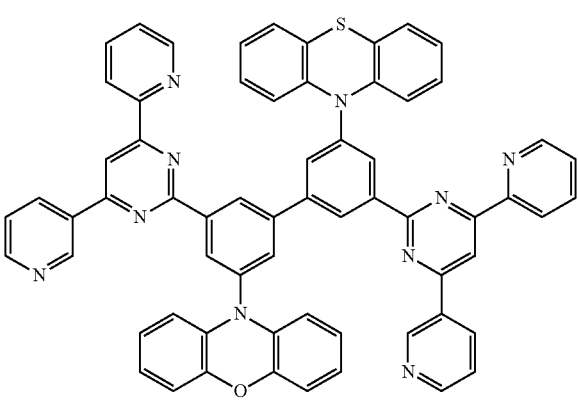
202
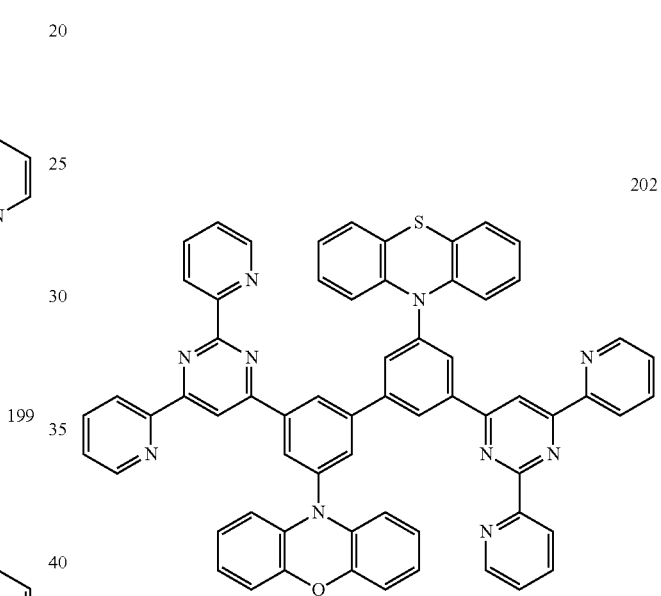
203
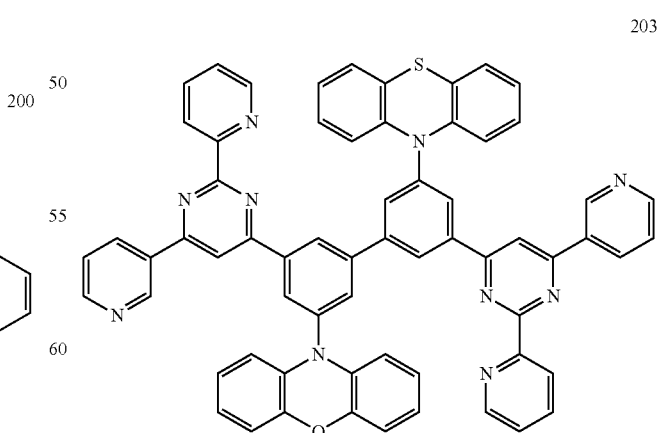

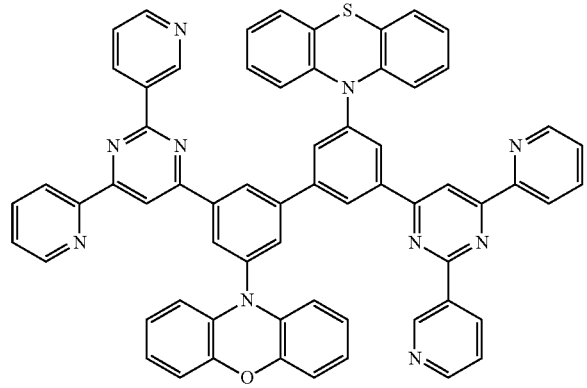

In one embodiment, the chemical bond having the curve

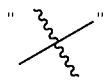

may refer to as a broken bond. The broken bond may be able to connect with another broken bond to form a complete chemical bond. The broken bond may cause two function groups to connect according to a general formula. Further, the function group having the broken bond may directly connect to a certain position of a phenyl group.

The disclosed nitrogen-containing heterocyclic compound may be synthesized by any appropriate methods. For illustrative purposes, the synthesis route and the synthesis method of

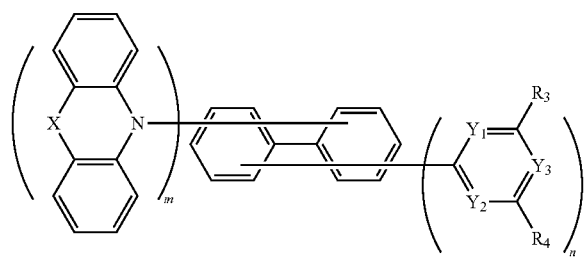

are described as an example, where n and m may be independent integers from 1 to 3; and a sum of m and n may be smaller than 5.

The synthesis route is shown as below.

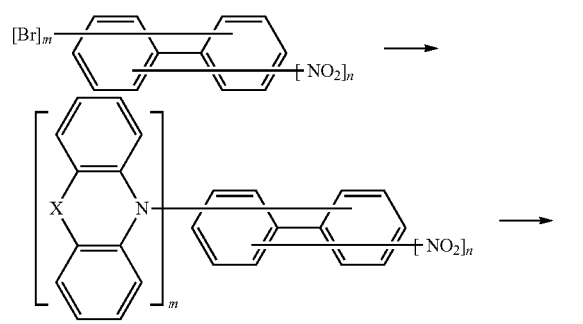

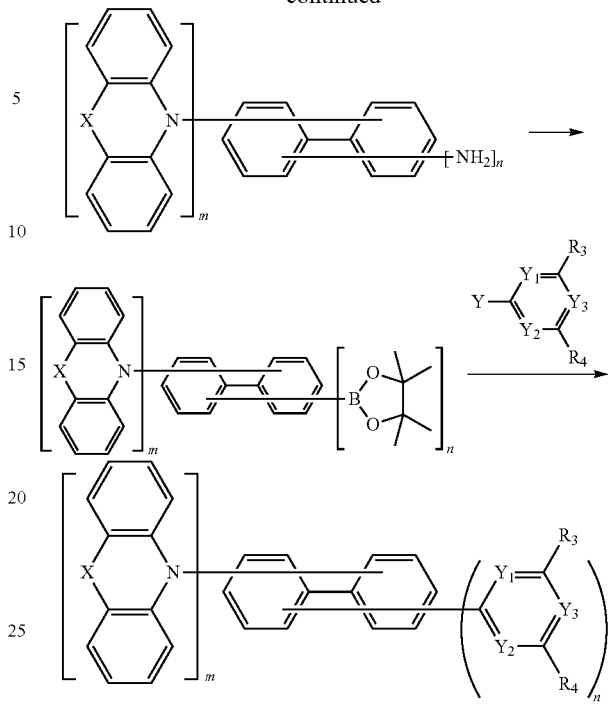

Where X, $Y_1$, $Y_2$, $Y_3$, $R_3$, and $R_4$ may be the same as the previously described elements and chemical structures, or other appropriate elements and chemical structures. Y may be a halogen atom, etc.

The synthesis of the nitrogen-containing heterocyclic compound may include following steps. Under an argon protective environment, the precursor (1 eq.) may react with

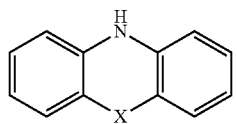

(1.01 m. eq.) in an environment having palladium acetate (0.05 m eq.), tri-tert-butylphosphine (TTBP) (0.075 m eq.) and $Cs_2CO_3$ (1.5 m eq.), etc. Such a reaction may be a Buchwald-Hartwig coupling reaction. Then, the product(s) may have a reduction reaction with a hydrogen gas. The produced intermediates (1 eq.) may have the azyl group to be brominated under the effects of $NaNO_2$ (3 n eq.), HBr (2.5 n eq), and CuBr (1.05 n eq). Then, the produced intermediates may react with bis(pinacolato)diboron (1.1 n eq.) under the effect of $Pd(dppf)Cl_2$ (0.035 n eq.) and potassium acetate (KOAc) (0.35 n eq.). Finally, the produced intermediates may have a coupling reaction with

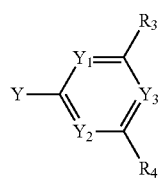

(0.91 n eq.) under the effect of Pd(PPh₃)₄ (0.045 n eq.) and K₂CO₃ (1.8 n eq.) to obtain the targeted compound.

In certain embodiments, such a synthesis method may be improved or modified to synthesize other compounds consistent with the disclosed embodiments. For example,

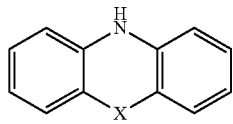

may be substituted or replaced by one or more compounds having the general formula (III). That is, a hydrogen atom may be connected to the broken bond. When

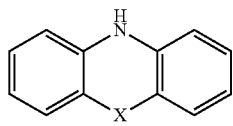

is substituted by two or more compounds (e.g., a mixture) having the general formula (III), the two or more compounds or the mixture may be simultaneously added to substitute the bromide atoms by a one-step substitution, or a multiple-step substitution.

According to the disclosed embodiments, the disclosed nitrogen-containing heterocyclic compounds may be applied in organic photoelectric apparatus. The organic photoelectric apparatus may be OLEDs, photovoltaic devices, organic photoelectric sensors, and organic data storage devices, etc.

Further, according to the disclosed embodiments, an organic photoelectric apparatus is provided. The organic photoelectric apparatus may include an anode layer, a cathode layer, and at least one organic layer formed between the anode layer and the cathode layer. The organic layer may include one or more of the disclosed compounds.

In one embodiment, the organic layer may include a light-emitting layer. The light-emitting layer may include one or more of the disclosed compounds. The disclosed compound may be used as at least one of doping material, co-doping material, and host material, etc.

In one embodiment, the organic layer may also include one or more of a hole-transport layer, a hole injection layer, an electron barrier layer, a hole barrier layer, an electron transport layer, and an electron injection layer, etc.

For illustrative purposes, OLED structures are described as examples of the organic photoelectric apparatus utilizing the disclosed compounds. FIGS. 1-5 illustrate exemplary OLED structures consistent with the disclosed embodiments.

As shown in FIGS. 1-5, the OLED utilizing the disclosed compound may include a substrate layer 100, and an anode layer 110 formed over the substrate layer 100. The anode layer 110 and the substrate layer 100 may be referred to as an anode substrate. The OLED may also include at least one light-emitting layer 130 formed over the anode layer 110, and a cathode layer 120 formed over the light-emitting layer 130. That is, the light-emitting layer 130 may be in between the anode layer 110 and the cathode layer 120.

In one embodiment, as shown in FIG. 1, the anode layer 110 and the cathode layer 120 of the OLED may only have the light-emitting layer 130 there-between. The electrons and holes may recombine to activate the light-emitting layer 130 to emit light. The light-emitting layer 130 may be made of one or more of the disclosed compounds.

Figure 2:
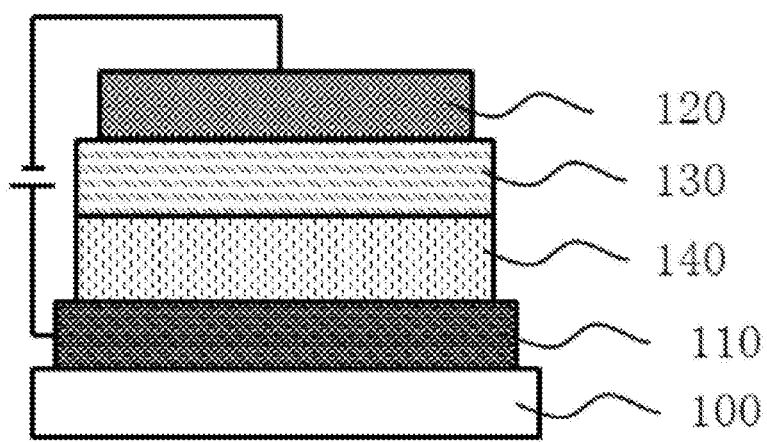
FIG. 2 illustrates another exemplary OLED consistent with the disclosed embodiments.

In certain embodiments, as shown in FIG. 2, a hole transport layer (HTL) 140 may be formed between the light-emitting layer 130 and the anode layer 110. That is, the HTL 140 and the light-emitting layer 130 may be in between the anode layer 110 and the cathode layer 120 of the OLED. The HTL 140 may transport the holes to the light-emitting layer 130. The light-emitting layer 130 may be made of one or more of the disclosed compounds.

Figure 3:
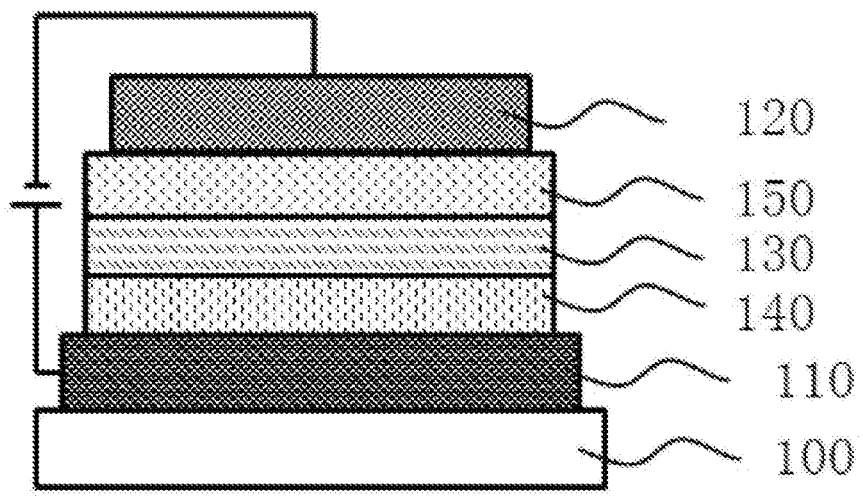
FIG. 3 illustrates another exemplary OLED consistent with the disclosed embodiments.

In still certain embodiments, as shown in FIG. 3, an electron transport layer (ETL) 150 may be formed between the cathode layer 120 and the light-emitting layer 130. That is, the HTL 140, the light-emitting layer 130 and the ETL 150 may be in between the anode layer 120 and the cathode layer 110. The ETL 150 may transport electrons to the light-emitting layer 130. The light-emitting layer 130 may be made of one or more of the disclosed compounds.

Figure 4:
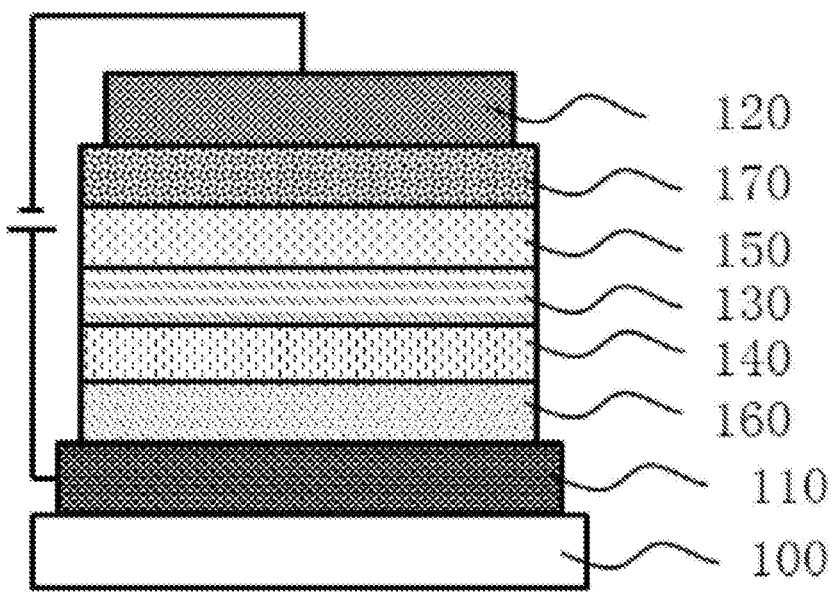
FIG. 4 illustrates another exemplary OLED consistent with the disclosed embodiment.

In still certain embodiments, as shown in FIG. 4, a hole injection layer (HIL) 160 may be formed between the anode layer 110 and the HTL 140; and an electron injection layer (EIL) 170 may be formed between the cathode layer 120 and the ETL 150. That is, the HIL 160, the HTL 140, the light-emitting layer 130, the ETL 150 and the EIL 170 may be in between the anode layer 110 and the cathode layer 120. The HIL 160 may be able to improve the ability to transport the holes from the anode layer 110 to the light-emitting layer 130. The EIL 170 may be able to improve the ability to transport the electrons from the cathode layer 120 to the light-emitting layer 130. Accordingly, the drive voltage of the OLED may be reduced. The light-emitting layer 130 may be made of one or more of the disclosed compounds.

Figure 5:
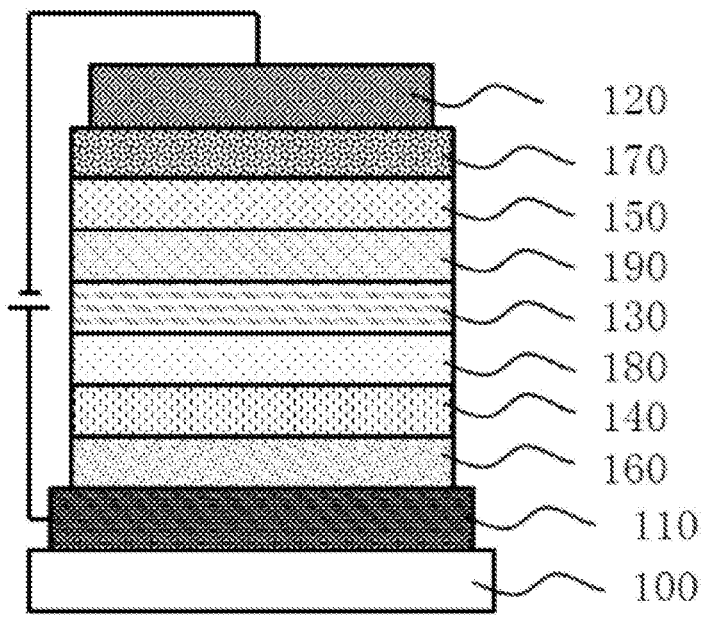
FIG. 5 illustrates another exemplary OLED consistent with the disclosed embodiments.

In still certain embodiments, as shown in FIG. 5, an electron barrier layer (EBL) 180 may be formed between the light-emitting layer 130 and the HTL 140; and a hole barrier layer (HBL) 190 may be formed between the light-emitting layer 130 and the ETL 150. That is, the HIL 160, the HTL 140, the EBL 180, the light-emitting layer 130, the HBL 190, the ETL 150 and the ETL 170 may be in between the anode layer 110 and the cathode layer 120. The EBL 180 may be able to prevent electrons from entering into the HTL 140 from the light-emitting layer 130; and the HBL 190 may be able to prevent the holes from entering into the ETL 150 from the light-emitting layer 130. The light-emitting layer 130 may be made of one or more of the disclosed compounds.

The anode layer 110 may be made of any appropriate material with a relatively large work function. The material used as the anode layer 110 may include Cu, Au, Ag, Fe, Cr, Ni, Mn, Pd, Pt, and a combination thereof. The material used as the anode layer 110 may also be metal oxide, such as SnO, ZnO, ITO, IZO, and a combination thereof. Further, the material used as the anode layer 110 may also be a conductive polymer, such as polyaniline, polypyrrole, poly(3-methylthiophene), and a combination thereof. In one embodiment, the anode layer 110 is made of ITO.

The cathode layer 120 may be made of any appropriate material with a relatively small work function, such as Al, Mg, Ag, In, Sn, Ti, Ca, Na, K, Li, Yb, Pb, and a combination thereof. The cathode layer 120 may also be made of a multi-layered material, such as LiF/Al, or Liq(8-quinolinol), etc. In one embodiment, an alloy of Mg and Ag or a double-layered structure of LiF/Al may be used as the cathode layer 120.

The HIL 160 may be made of any appropriate material such that the injection of holes from the anode layer 110 to the organic interface layer may be increased; and the HIL 160 may have a desired adhesion to the surface of the ITO anode 110. The material used as the HIL 160 may include the polymers with the HOMO energy level matching the work function of ITO, such as porphyrin compounds of CuPc, naphthylenediamine-containing stellate triphenylamine derivatives of 4,4',4"-tris[2-naphthyl-phenyl-amino]triphenylamine (TNATA) and poly(3,4-Ethylenedioxythiophene): polystyrene sulfonate (PEDOT:PSS), and electron withdrawing nitrogen-containing heterocyclic compounds of hexaazatriphenylenehexacabonitrile (HATCN), etc.

The HTL 140 and the EBL 180 may be may made of any appropriate material having a relatively high glass transition temperature and a high hole mobility. The material used as the HTL 140 and EBL 180 may include the diphenyl diamine derivatives of N,N'-Di-[(1-naphthalenyl)-N,N'-diphenyl]-1,1'-biphenyl)-4,4'-diamine(NPD), the crossing diphenyl diamine derivatives of 2',7,7'-tetrakis(N,N-diphenylamino)-9,9-spirobifluorene (spiro-TAD), and the stellate triphenylamine derivatives of 4,4',4"-tris(carbazol-9-yl)triphenylamine (TCTA), etc.

The HBL 190 and the ETL 150 may be made of any appropriate material having a relatively low HOMO energy level, and a relatively high electron mobility. The material used as the HBL 190 and the ETL 150 may include the metal-quinolinolatocomplexs of bis(2-methyl-8-quinolinolato-N1,O8)-(1,1'-Biphenyl-4-olato)aluminum (BAlq), tris (8-hydroxyquinolinato)aluminum (Alq), 8-hydroxyquionline lithium, the phenanthroline derivatives of 4,7-diphenyl-1,10-phenanthroline (BPhen), the imidazoline derivatives of 1,3,5-Tris(1-phenyl-1H-benzimidazol-2-yl)benzene (TPBI), or the triazine derivatives of 2,4,6-Tri(9H-carbazol-9-yl)-1, 3,5-triazine, etc.

The OLED having the disclosed compound may be formed by any appropriate methods. In one embodiment, the method for forming the OLED may include forming an anode layer on a smooth transparent or opaque substrate; forming an organic layer made of at least one of the disclosed compounds; and forming a cathode layer on the organic layer. The organic layer may be formed by any appropriate process, such as a thermal evaporation process, a sputtering process, a spin-coating process, a dip-coating process, or an ion deposition process, etc.

The following embodiments will further describe the advantages of the disclosed compounds and OLEDs having the disclosed compounds. Exemplary embodiments 1-15 describe the simulation process of exemplary compounds consistent with the disclosed embodiments.

The energy level difference of the minimum singlet state $S_1$ and the minimum triplet state $T_1$ of an organic material may be simulated by Guassian 09 software (Guassian Inc.). The detailed simulation method of the energy level difference $\Delta E_{st}$ may refer to J. Chem. Theory Comput., 2013, DOI: 10.1021/ct400415r. The optimization of the molecular structure and the activation may all be obtained by TD-DFT method "B3LYP" and base group "6-31 g(d)".

In embodiment 1, a simulation process is performed on the compound 1.

In embodiment 2, a simulation process is performed on the compound 16.

In embodiment 3, a simulation process is performed on the compound 40.

In embodiment 4, a simulation process is performed on the compound 61.

In embodiment 5, a simulation process is performed on the compound 62.

In embodiment 6, a simulation process is performed on the compound 63.

In embodiment 7, a simulation process is performed on the compound 64.

In embodiment 8, a simulation process is performed on the compound 65.

In embodiment 9, a simulation process is performed on the compound 91.

In embodiment 10, a simulation process is performed on the compound 108.

In embodiment 11, a simulation process is performed on the compound 163.

In embodiment 12, a simulation process is performed on the compound 166.

In embodiment 13, a simulation process is performed on the compound 169.

In embodiment 14, a simulation process is performed on the compound 185.

In embodiment 15, a simulation process is performed on the compound 196.

The simulation results are illustrated in Table 1.

TABLE 1

|  | Compound | S1 (eV) | T1 (eV) | $\Delta E_{st}$ (eV) |
|---|---|---|---|---|
| Embodiment 1 | 1 | 2.45 | 2.43 | 0.02 |
| Embodiment 2 | 16 | 2.32 | 2.30 | 0.02 |
| Embodiment 3 | 40 | 2.03 | 2.01 | 0.02 |
| Embodiment 4 | 61 | 2.43 | 2.41 | 0.02 |
| Embodiment 5 | 62 | 2.74 | 2.73 | 0.01 |
| Embodiment 6 | 63 | 2.84 | 2.82 | 0.02 |
| Embodiment 7 | 64 | 2.81 | 2.79 | 0.02 |
| Embodiment 8 | 65 | 2.04 | 2.02 | 0.02 |
| Embodiment 9 | 91 | 2.60 | 2.58 | 0.02 |
| Embodiment 10 | 108 | 2.75 | 2.74 | 0.01 |
| Embodiment 11 | 163 | 2.622 | 2.620 | 0.002 |
| Embodiment 12 | 166 | 2.39 | 2.37 | 0.02 |
| Embodiment 13 | 169 | 2.62 | 2.59 | 0.03 |
| Embodiment 14 | 185 | 2.99 | 2.73 | 0.26 |
| Embodiment 15 | 196 | 2.77 | 2.66 | 0.11 |

As shown in Table 1, the energy level difference $\Delta E_{st}$ between the minimum single state $S_1$ and the triplet state $T_1$ may all be relatively small, from the embodiment 1 to the embodiment 15. Thus, the compounds illustrated in Table 1 may all be able to achieve a reverse intersystem transport; and may possess the performances of the TADF materials.

Embodiments 16-25 describe exemplary synthesis routes of the disclosed compounds consistent with the disclosed embodiments.

Embodiment 16 describes the synthesis route and synthesis process of the compound 1. The synthesis route is illustrated as follows.

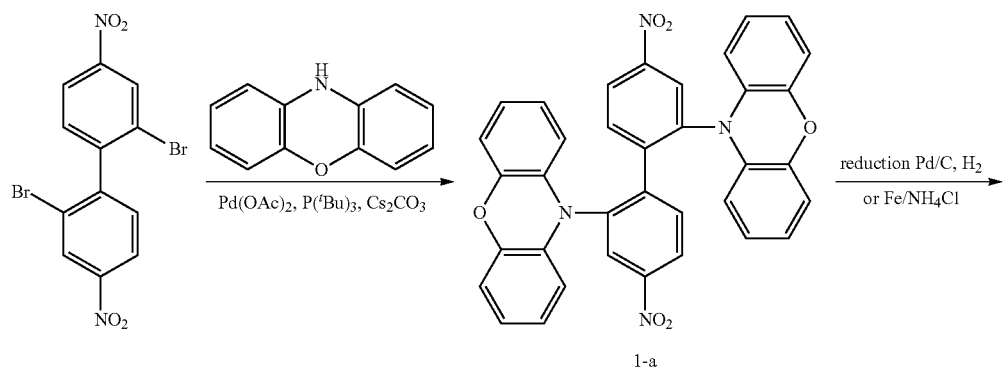
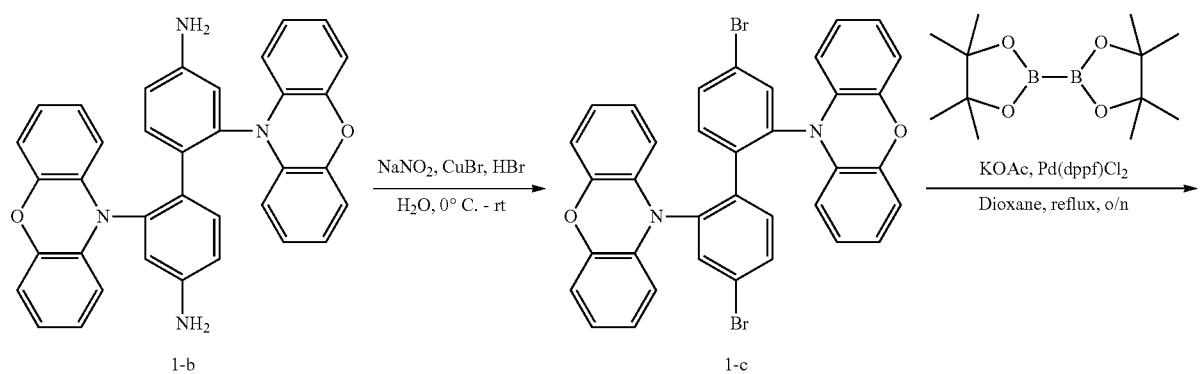
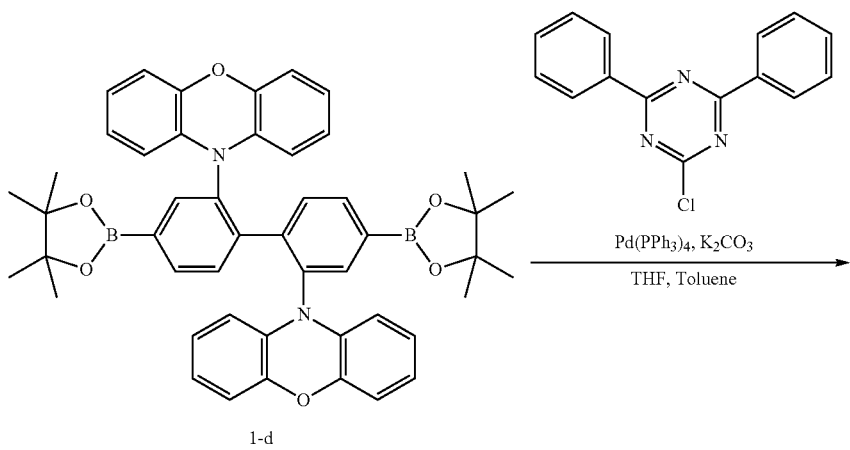

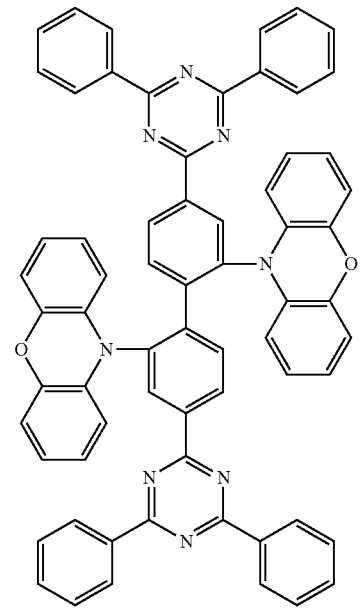

1

The first step of the synthesis process of the compound 1 may be to synthesize the compound 1-a illustrated in the synthesis route. 4,4'-dibroMo-2,2'-dinitrobiphenyl (20 g, 49.8 mmol), phenoxazine (18.4 g, 100.4 mmol), Pd(OAc)$_2$ (1.2 g, 5.4 mmol), tri-tert-butylphosphine (1.6 g, 7.8 mmol) and Cs$_2$CO$_3$ (48.6 g, 149.4 mmol) may be dissolved in toluene; and may be refluxed for 8 hours in a nitrogen environment. Then, the solvent may be evaporated under vacuum. The residues may be added into pentane; and stirred and filtered. Then, the products may be purified by a silicone gel chromatographic column. Thus, the solid compound 1-a (12.7 g, 48%) may be obtained.

The second step of the synthesis process of the compound 1 may be to synthesize the compound 1-b illustrated in the synthesis route. The intermediate 1-a (12.7 g, 20.9 mmol) may be dissolved in methanol. Under the protection of Ar gas, 2 g Pd/C may be slowly added into the solution. After substituting the gas in the reaction flask with hydrogen, the reaction may be continued for 20 hours in the hydrogen environment. After filtering and evaporating the solvent, the intermediate 1-b (9.7 g, 85%) may be obtained.

The third step of the synthesis process of the compound 1 may be to synthesize the compound 1-c illustrated in the synthesis route. NaNO$_2$ (7.2 g, 106.2 mmol) may be dissolved in 10 ml water. Such a solution may be slowly added into a mixture of the intermediate 1-b (9.7 g, 17.7 mmol) and 10.8 ml of HBr with a concentration of 48%; and stirred for 1 hour in an ice bath (0° C.). Under the ice bath condition, 10 ml CuBr in HBr solution (5.4 g, 37.9 mmol) may be added into the mixture; and the reaction may continue for 1 hour in the ice bath. Then, the mixture may be heated to 60° C.; and react for 2 hours. After being cooling down, an extraction process may be performed using 50 ml ethyl acetate. The organic layer may be washed by water for a plurality of times; and dried by dehydrated MgSO$_4$. After filtering and evaporating the solvent, the intermediate 1-c (8.8 g, yield 74%) may be obtained.

The fourth step of the synthesis process of the compound 1 may be to synthesize the compound 1-d illustrated in the synthesis route. Under a nitrogen gas flow, the catalyst Pd(dppf)Cl$_2$ (0.7 g, 0.9 mmol), KOAc (0.9 g, 9.1 mmol), and bis(pinacolato)diboron (7.3 g, 28.8 mmol) may be mixed in a reaction flask. The intermediate 1-c (8.8 g, 13.1 mmol) may be dissolved in 200 ml 1,4-Dioxane solution; and added into the reaction flask. The mixture may be refluxed for 12 hours. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the intermediate 1-d (4.2 g, yield 42%) may be obtained.

The fifth step of the synthesis process of the compound 1 may be to synthesize the final compound 1 illustrated in the synthesis route. 2-chloro-4,6-diphenyl-1,3,5-triazine (2.7 g, 10.0 mmol), the catalyst Pd(PPh$_3$)$_4$ (0.6 g, 0.5 mmol) and the intermediate 1-d (4.2 g, 5.5 mmol) may be dissolved in THF; and then the mixture may dropped into the 100 ml K$_2$CO$_3$ (2.8 g, 20.0 mmol) water solution. The mixture may be stirred; and refluxed for 2 days. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the compound 1 (3.0 g, yield 42%) may be obtained.

An LC-MS method may be used to analyze the final product (the obtained compound 1). The ESI-MS (m/z) of the final product is approximately 979.3 [M+H]$^+$. Such a value corresponds to the molecular weight of the compound 1.

Embodiment 17 describes the synthesis route and the synthesis process of the compound 61. The synthesis route is illustrated as below.

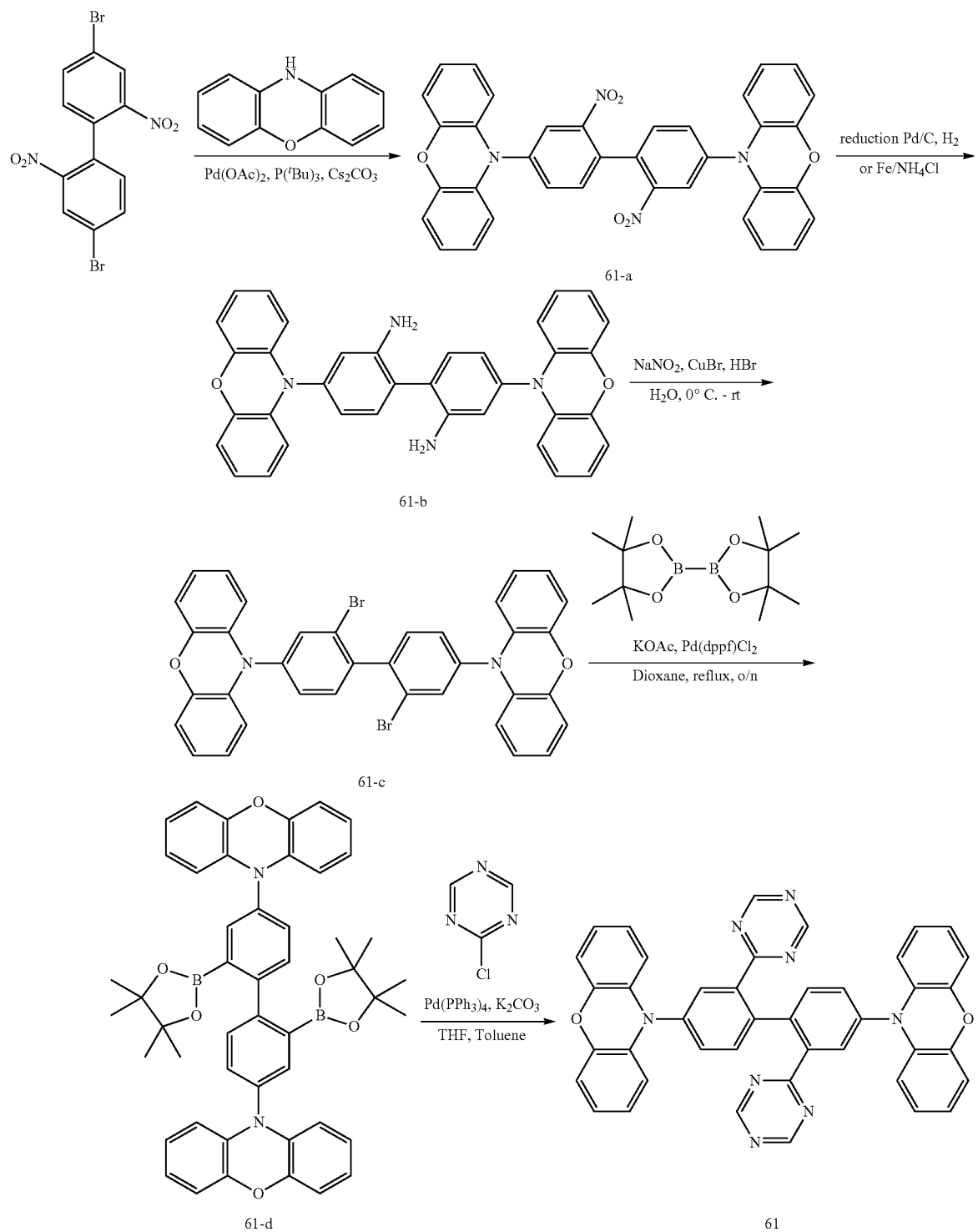

The first step of the synthesis process of the compound 61 may be to synthesize the compound 61-a illustrated in the synthesis route. 4,4'-dibroMo-2,2'-dinitrobiphenyl (20 g, 49.8 mmol), phenoxazine (18.4 g, 100.4 mmol), $Pd(OAc)_2$ (1.2 g, 5.4 mmol), tri-tert-butylphosphine (1.6 g, 7.8 mmol) and $Cs_2CO_3$ (48.6 g, 149.4 mmol) may be dissolved in toluene; and may be refluxed for 8 hours in a nitrogen environment. Then, the solvent may be completely evaporated under vacuum. The residues may be added into pentane; and stirred and filtered. Then, the products may be purified by a silicone gel chromatographic column. Thus, the solid compound 61-a (16.0 g, 53%) may be obtained.

The second step of the synthesis process of the compound 61 may be to synthesize the compound 61-b illustrated in the synthesis route. The intermediate 61-a (16.0 g, 26.4 mmol) may be dissolved in methanol. Under the protection of Ar gas, 2 g Pd/C may be slowly added into the solution. After substituting the gas in the reaction flask with hydrogen, the reaction may be continued for 20 hours in the hydrogen environment. After filtering and evaporating the solvent, the intermediate 61-b (10.8 g, 75%) may be obtained.

The third step of the synthesis process of the compound 61 may be to synthesize the compound 61-c illustrated in the synthesis route. $NaNO_2$ (8.2 g, 118.8 mmol) may be dissolved in 10 ml water. Such a solution may be slowly added into a mixture of the intermediate 61-b (10.8 g, 19.8 mmol) and 12.2 ml of HBr (approximately 99.0 mmol) with a concentration of 48%; and stirred for 1 hour in an ice bath (0° C.). Under the ice bath condition, 10 ml CuBr in HBr solution (6.0 g, 41.6 mmol) may be added into the mixture; and the reaction may continue for 1 hour in the ice bath. Then, the mixture may be heated to 60° C.; and react for 2 hours. After being cooling down, an extraction process may be performed using 50 ml ethyl acetate. The organic layer may be washed by water for a plurality of times; and dried by dehydrated $MgSO_4$. After filtering and evaporating the solvent, the intermediate 61-c (9.6 g, yield 74%) may be obtained.

The fourth step of the synthesis process of the compound 61 may be to synthesize the compound 61-d illustrated in the synthesis route. Under a $N_2$ gas flow, the catalyst Pd(dppf)$Cl_2$ (0.7 g, 1.0 mmol), KOAc (1.0 g, 10.1 mmol), and bis(pinacolato)diboron (8.0 g, 31.4 mmol) may be mixed in a reaction flask. The intermediate 61-c (9.6 g, 14.3 mmol) may be dissolved in 250 ml 1,4-Dioxane solution; and added into the reaction flask. The mixture may be refluxed for 12 hours. After cooling down, toluene may be added to perform an extraction process. Then, the product may be washed by water for a plurality of times; and dried by dehydrated $MgSO_4$. The organic layer may be filtered; and the solvent may be evaporated. Then, the product may be purified by a silicone gel chromatographic column; and the intermediate 61-d (5.2 g, yield 47%) may be obtained.

The fifth step of the synthesis process of the compound 61 may be to synthesize the final compound 61 illustrated in the synthesis route. 2-chloro-4,6-diphenyl-1,3,5-triazine (1.4 g, 12.2 mmol), the catalyst Pd(PPh$_3$)$_4$ (0.7 g, 0.6 mmol) and the intermediate 61-d (5.2 g, 6.7 mmol) may be dissolved in 100 ml THF; and then the mixture may dropped into the 100 ml $K_2CO_3$ (3.4 g, 24.40 mmol) water solution. The mixture may be stirred; and refluxed for 2 days. After cooling down, toluene may be added to perform an extraction process. Then, the product may be washed by water for a couple of times; and dried by dehydrated $MgSO_4$. The organic layer may be filtered; and the solvent may be evaporated. Then, the product may be purified by a silicone gel chromatographic column; and the final compound 61 (2.0 g, yield 45%) may be obtained.

An LC-MS method may be used to analyze the final product (the obtained compound 61). The ESI-MS (m/z) of the final product is approximately 675.1 $[M+H]^+$. Such a value corresponds to the molecular weight of the compound 61.

Embodiment 18 describes the synthesis route and synthesis process of the compound 62. The synthesis route is illustrated as below.

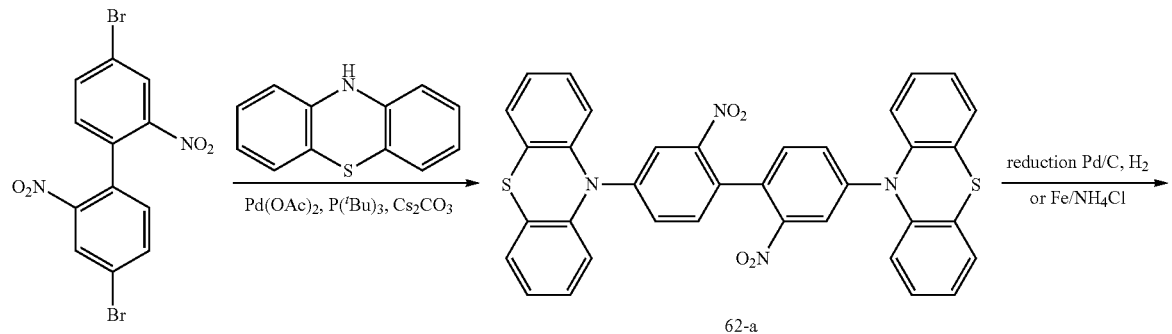

62-a

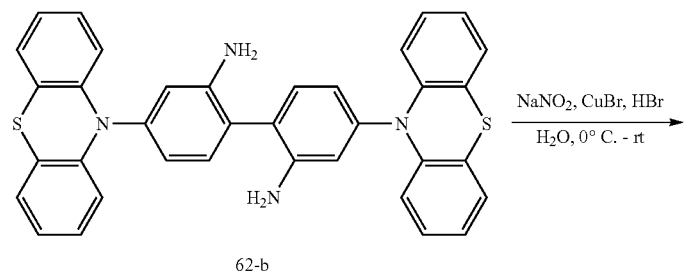

62-b

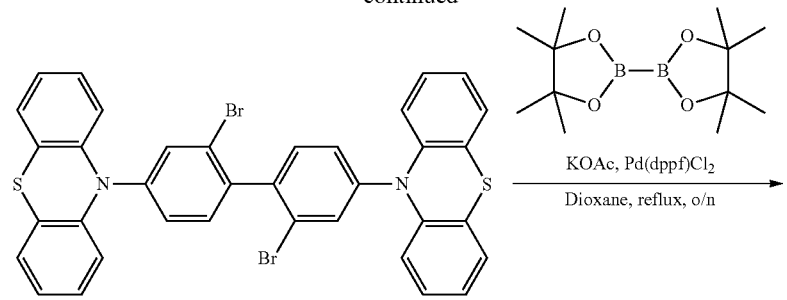

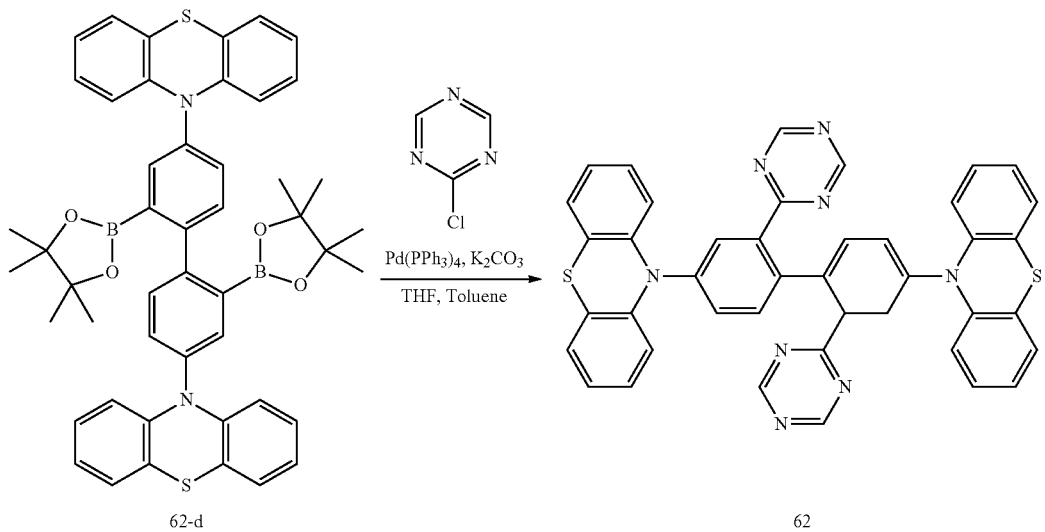

62-d              62

The first step of the synthesis process of the compound 62 may be to synthesize the compound 62-a illustrated in the synthesis route. 4,4'-dibroMo-2,2'-dinitrobiphenyl (20 g, 49.8 mmol), phenothiazine (20.0 g, 100.4 mmol), Pd(OAc)$_2$ (1.2 g, 5.4 mmol), tri-tert-butylphosphine (1.6 g, 7.8 mmol) and Cs$_2$CO$_3$ (48.6 g, 149.4 mmol) may be dissolved in toluene; and may be refluxed for 8 hours in a nitrogen environment. Then, the solvent may be completely evaporated under vacuum. The residues may be added into pentane; and stirred and filtered. Then, the products may be purified by a silicone gel chromatographic column. Thus, the solid compound 62-a (20.4 g, 64%) may be obtained.

The second step of the synthesis process of the compound 62 may be to synthesize the compound 62-b illustrated in the synthesis route. The intermediate 62-a (20.4 g, 31.9 mmol) may be dissolved in methanol. Under the protection of Ar gas, 3 g Pd/C may be slowly added into the solution. After substituting the gas in the reaction flask with hydrogen, the reaction may be continued for 20 hours in the hydrogen environment. After filtering and evaporating the solvent, the intermediate 62-b (14.4 g, 78%) may be obtained.

The third step of the synthesis process of the compound 62 may be to synthesize the compound 62-c illustrated in the synthesis route. NaNO$_2$ (10.3 g, 149.3 mmol) may be dissolved in 13 ml water. Such a solution may be slowly added into a mixture of the intermediate 62-b (14.4 g, 24.9 mmol) and 15.4 ml of HBr (approximately 125.0 mmol) with a concentration of 48%; and stirred for 1 hour in an ice bath (0° C.). Under the ice bath condition, 10 ml CuBr in HBr solution (7.5 g, 52.3 mmol) may be added into the mixture; and the reaction may continue for 1 hour in the ice bath. Then, the mixture may be heated to 60° C. and react for 2 hours. After being cooling down, an extraction process may be performed using 50 ml ethyl acetate. The organic layer may be washed by water for a plurality of times; and dried by dehydrated MgSO$_4$. After filtering and evaporating the solvent, the intermediate 62-c (14.4 g, yield 82%) may be obtained.

The fourth step of the synthesis process of the compound 62 may be to synthesize the compound 62-d illustrated in the synthesis route. Under the N$_2$ gas flow, the catalyst Pd(dppf)Cl$_2$ (1 g, 1.4 mmol), KOAc (1.4 g, 14.3 mmol), and bis (pinacolato)diboron (11.4 g, 44.9 mmol) may be mixed in a reaction flask. The intermediate 62-c (14.4 g, 20.4 mmol) may be dissolved in 250 ml 1,4-Dioxane solution; and added into the reaction flask. The mixture may be refluxed for 12 hours. After cooling down, toluene may be added to perform an extraction process. Then, the product may be washed by water for a couple of times; and dried by dehydrated MgSO$_4$. The organic layer may be filtered; and the solvent may be evaporated. Then, the product may be purified by a silicone gel chromatographic column; and the intermediate 62-d (7.2 g, yield 43%) may be obtained.

The fifth step of the synthesis process of the compound 62 may be to synthesize the final compound 62 illustrated in the synthesis route. 2-chloro-4,6-diphenyl-1,3,5-triazine (1.8 g, 16.0 mmol), catalyst Pd(PPh$_3$)$_4$ (0.9 g, 0.8 mmol) and the intermediate 62-d (7.2 g, 8.8 mmol) may be dissolved in 100 ml THF; and then the mixture may dropped into the 100 ml K$_2$CO$_3$ (4.4 g, 32.0 mmol) water solution. The mixture may be stirred; and refluxed for 2 days. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the compound 62 (2.4 g, yield 38%) may be obtained.

An LC-MS method may be used to analyze the final product (the obtained compound 62). The ESI-MS (m/z) of the final product is approximately 707.1 [M+H]$^+$. Such a value corresponds to the molecular weight of the compound 62.

Embodiment 19 describes the synthesis route and process of the compound 63. The synthesis route is illustrated as below.

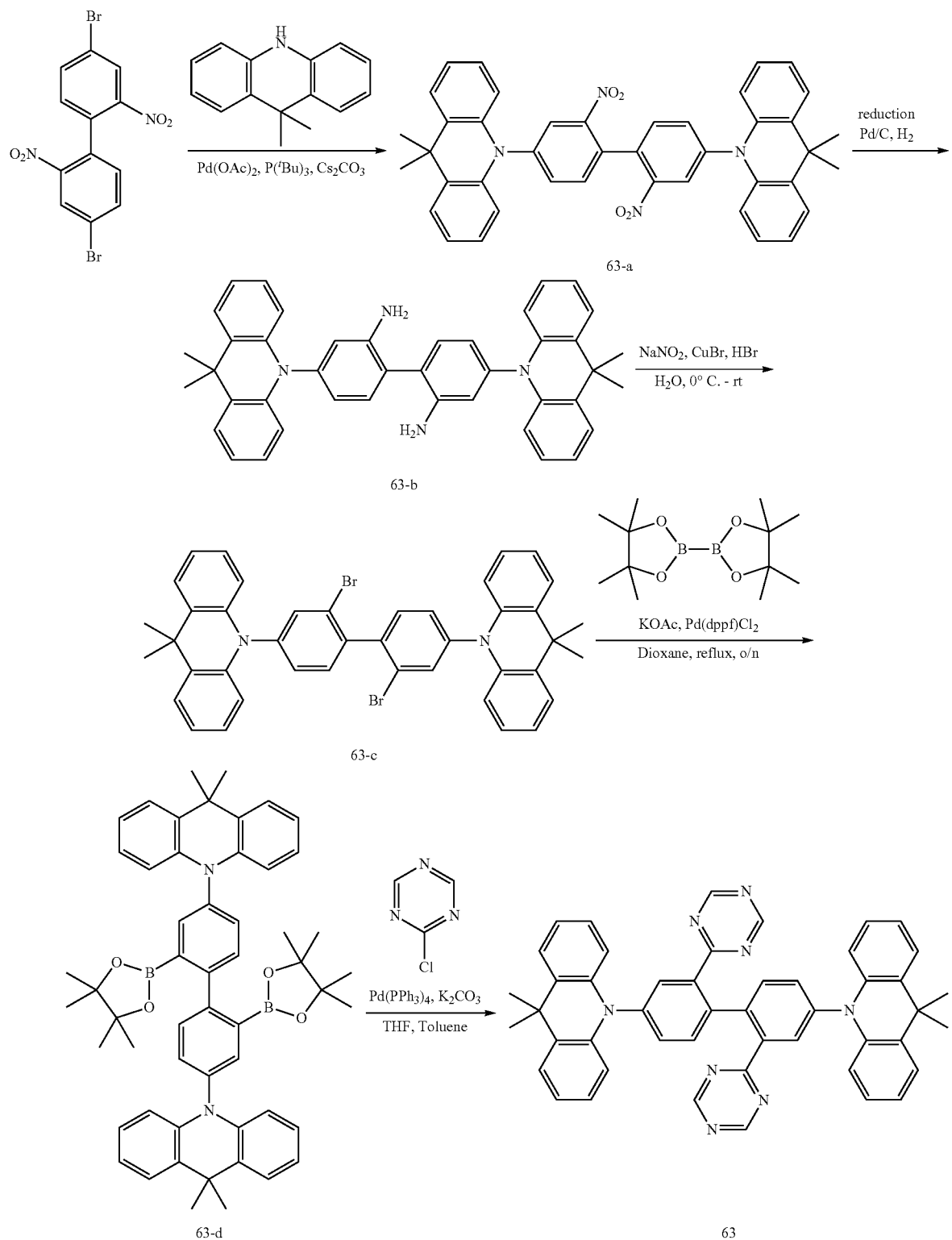

The first step of the synthesis process of the compound 63 may be to synthesize the compound 63-a illustrated in the synthesis route. 4,4'-dibroMo-2,2'-dinitrobiphenyl (21.0 g, 49.8 mmol), 9,9-diMethylacridan (21.0 g, 100.4 mmol), Pd(OAc)$_2$ (1.2 g, 5.4 mmol), tri-tert-butylphosphine (1.6 g, 7.8 mmol) and Cs$_2$CO$_3$ (48.6 g, 149.4 mmol) may be dissolved in toluene; and may be refluxed for 8 hours in nitrogen environment. Then, the solvent may be completely evaporated under vacuum. The residues may be added into pentane; and stirred and filtered. Then, the products may be purified by silicone gel chromatographic column. Thus, the solid compound 63-a (10.2 g, 31%) may be obtained.

The second step of the synthesis process of the compound 63 may be to synthesize the compound 63-b illustrated in the synthesis route. The intermediate 63-a (10.2 g, 15.4 mmol) may be dissolved in methanol. Under the protection of Ar gas, 3 g Pd/C may be slowly added into the solution. After substituting the gas in the reaction chamber with hydrogen, the reaction may be continued for 20 hours in the hydrogen environment. After filtering and evaporating the solvent, the intermediate 63-b (8.1 g, 86%) may be obtained.

The third step of the synthesis process of the compound 63 may be to synthesize the compound 63-c illustrated in the synthesis route. NaNO$_2$ (5.5 g, 79.5 mmol) may be dissolved in 8 ml water. Such a solution may be slowly added into a mixture of the intermediate 63-b (8.1 g, 13.2 mmol) and 8 ml of HBr (approximately 66.0 mmol) with a concentration of 48%; and stirred for 1 hour in an ice bath (0° C.). Under the ice bath condition, 10 ml CuBr in HBr solution (4.0 g, 27.7 mmol) may be added into the mixture; and the reaction may continue for 1 hour in the ice bath. Then, the mixture may be heated to 60° C. to react for 2 hours. After being cooling down, an extraction process may be performed using 50 ml ethyl acetate. The organic layer may be washed by water for a plurality of times; and dried by dehydrated MgSO$_4$. After filtering and evaporating the solvent, the intermediate 63-c (7.1 g, yield 82%) may be obtained.

The fourth step of the synthesis process of the compound 63 may be to synthesize the compound 63-d illustrated in the synthesis route. Under a N$_2$ gas flow, the catalyst Pd(dppf)Cl$_2$ (0.5 g, 0.7 mmol), KOAc (0.7 g, 6.9 mmol), and bis(pinacolato)diboron (5.5 g, 21.6 mmol) may be mixed in a reaction flask. The intermediate 63-c (7.1 g, 9.8 mmol) may be dissolved in 150 ml 1,4-Dioxane solution; and added into the reaction flask. The mixture may be refluxed for 12 hours. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the intermediate 63-d (2.9 g, yield 36%) may be obtained.

The fifth step of the synthesis process of the compound 63 may be to synthesize the final compound 63 illustrated in the synthesis route. 2-chloro-4,6-diphenyl-1,3,5-triazine (0.7 g, 6.4 mmol), the catalyst Pd(PPh$_3$)$_4$ (0.3 g, 0.3 mmol) and the intermediate 63-d (2.9 g, 3.5 mmol) may be dissolved in 100 ml THF, then the mixture may be dropped into the 100 ml K$_2$CO$_3$ (1.8 g, 12.8 mmol) water solution. The mixture may be stirred; and refluxed for 2 days. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the compound 63 (1.4 g, yield 54%) may be obtained.

An LC-MS method may be used to analyze the final product (the obtained compound 63). The ESI-MS (m/z) of the final product is approximately 727.2 [M+H]$^+$. Such a value corresponds to the molecular weight of the compound 63.

Embodiment 20 describes the synthesis route and synthesis process of the compound 64. The synthesis route is illustrated as below.

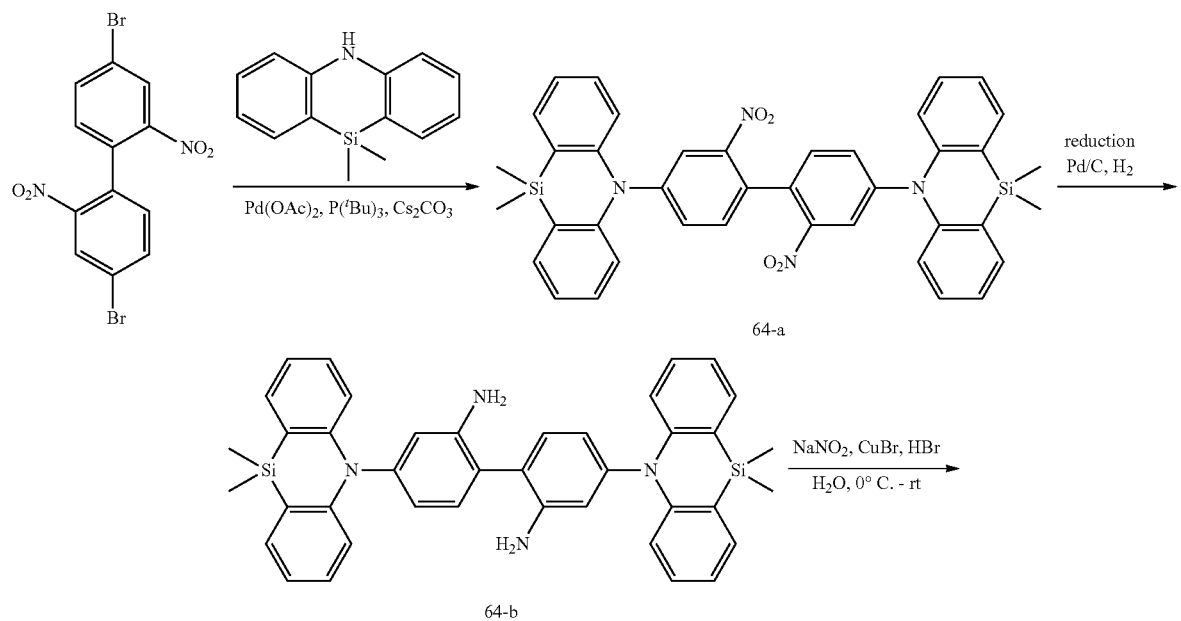

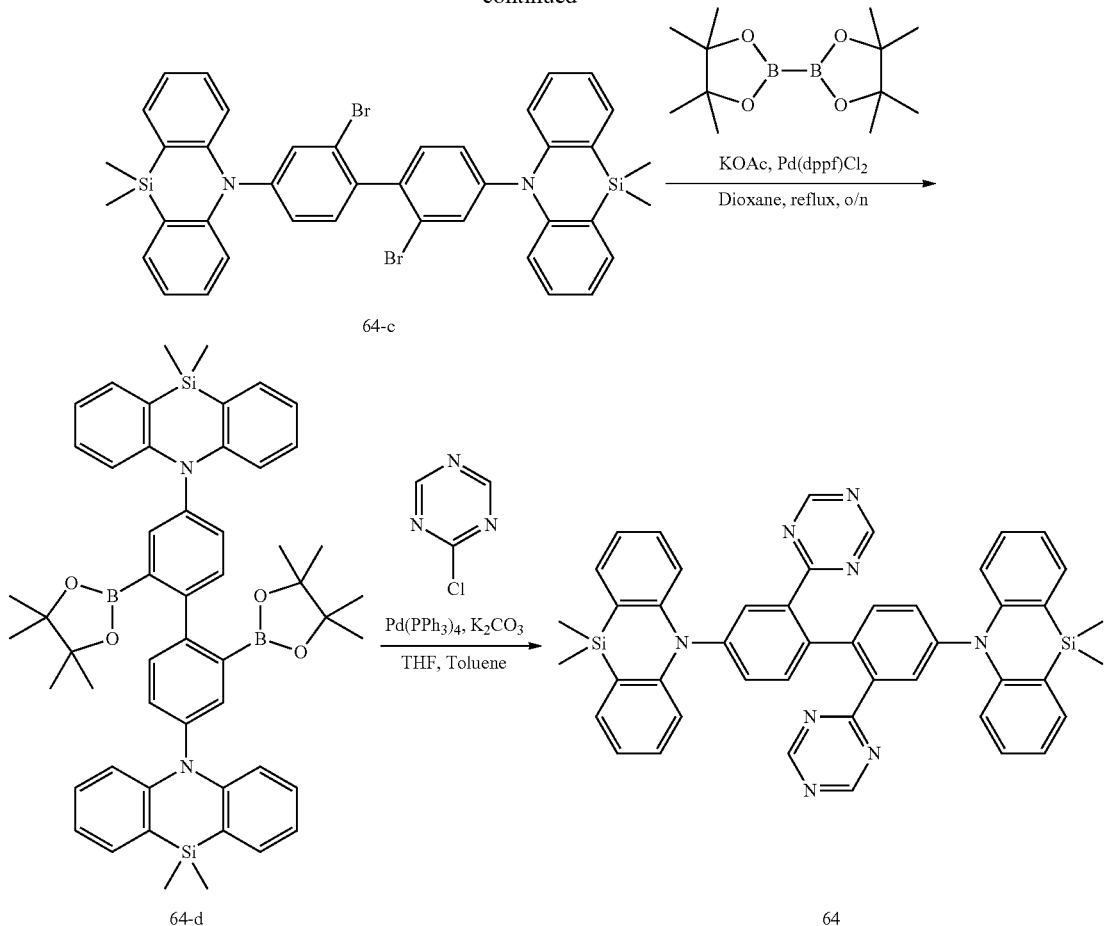

The first step of the synthesis process of the compound 64 may be to synthesize the compound 64-a illustrated in the synthesis route. 4,4'-dibroMo-2,2'-dinitrobiphenyl (20.0 g, 49.8 mmol), 10,10-Dimethyl-5,10-dihydro-dibenzo[b,e][1,4]aza silacyclo (22.6 g, 100.4 mmol), Pd(OAc)₂ (1.2 g, 5.4 mmol), tri-tert-butylphosphine (1.6 g, 7.8 mmol) and Cs₂CO₃ (48.6 g, 149.4 mmol) may be dissolved in toluene; and may be refluxed for 8 hours in nitrogen environment. Then, the solvent may be completely evaporated under vacuum. The residues may be added into pentane; and stirred and filtered. Then, the products may be purified by silicone gel chromatographic column. Thus, the solid compound 64-a (12.4 g, 36%) may be obtained.

The second step of the synthesis process of the compound 64 may be to synthesize the compound 64-b illustrated in the synthesis route. The intermediate 64-a (12.4 g, 17.9 mmol) may be dissolved in methanol. Under the protection of Ar gas, 3 g Pd/C may be slowly added into the solution. After substituting the gas in the reaction flask with hydrogen, the reaction may be continued for 20 hours in the hydrogen environment. After filtering and evaporating the solvent, the intermediate 64-b (9.4 g, 81%) may be obtained.

The third step of the synthesis process of the compound 64 may be to synthesize the compound 64-c illustrated in the synthesis route. NaNO₂ (6.0 g, 87.0 mmol) may be dissolved in 8 ml water. Such a solution may be slowly added into a mixture of the intermediate 64-b (9.4 g, 14.5 mmol) and 9 ml of HBr (approximately 73.0 mmol) with a concentration of 48%; and stirred for 1 hour in an ice bath (0° C.). Under the ice bath condition, 10 ml CuBr in HBr solution (4.4 g, 30.5 mmol) may be added into the mixture; and the reaction may continue for 1 hour in the ice bath. Then, the mixture may be heated to 60° C. to react for 2 hours. After being cooling down, an extraction process may be performed using 50 ml ethyl acetate. The organic layer may be washed by water for a plurality of times; and dried by dehydrated MgSO₄. After filtering and evaporating the solvent, the intermediate 64-c (7.6 g, yield 69%) may be obtained.

The fourth step of the synthesis process of the compound 64 may be to synthesize the compound 64-d illustrated in the synthesis route. Under the N₂ gas flow, the catalyst Pd(dppf)Cl₂ (0.5 g, 0.7 mmol), KOAc (0.7 g, 7.0 mmol), and bis(pinacolato)diboron (5.6 g, 22.0 mmol) may be mixed in a reaction flask. The intermediate 64-c (7.6 g, 10.0 mmol) may be dissolved in 150 ml 1,4-Dioxane solution; and added into the reaction flask. The mixture may be refluxed for 12 hours. After cooling down, toluene may be added to perform an extraction process. Then, the product may be washed by water for a plurality of times; and dried by dehydrated MgSO₄. The organic layer may be filtered; and the solvent may be evaporated. Then, the product may be purified by a silicone gel chromatographic column; and the intermediate 64-d (2.6 g, yield 31%) may be obtained.

The fifth step of the synthesis process of the compound 64 may be to synthesize the final compound 64 illustrated in the synthesis route. 2-chloro-4,6-diphenyl-1,3,5-triazine (0.6 g, 5.6 mmol), the catalyst Pd(PPh$_3$)$_4$ (0.3 g, 0.3 mmol) and the intermediate 64-d (2.6 g, 3.1 mmol) may be dissolved in 100 ml THF; and then the mixture may dropped into the 100 ml K$_2$CO$_3$ (1.6 g, 11.3 mmol) water solution. The mixture may be stirred; and refluxed for 2 days. After cooling down, toluene may be added to perform an extraction process. Then, the product may be washed by water for a couple of times; and dried by dehydrated MgSO$_4$. The organic layer may be filtered; and the solvent may be evaporated. Then, the product may be purified by a silicone gel chromatographic column; and the compound 64 (1.1 g, yield 48%) may be obtained.

An LC-MS method may be used to analyze the final product (the obtained compound 64). The ESI-MS (m/z) of the final product is approximately 759.1 [M+H]$^+$. Such a value corresponds to the molecular weight of the compound 64.

Embodiment 21 describes the synthesis route and the synthesis process of the compound 91. The synthesis route is illustrated as below.

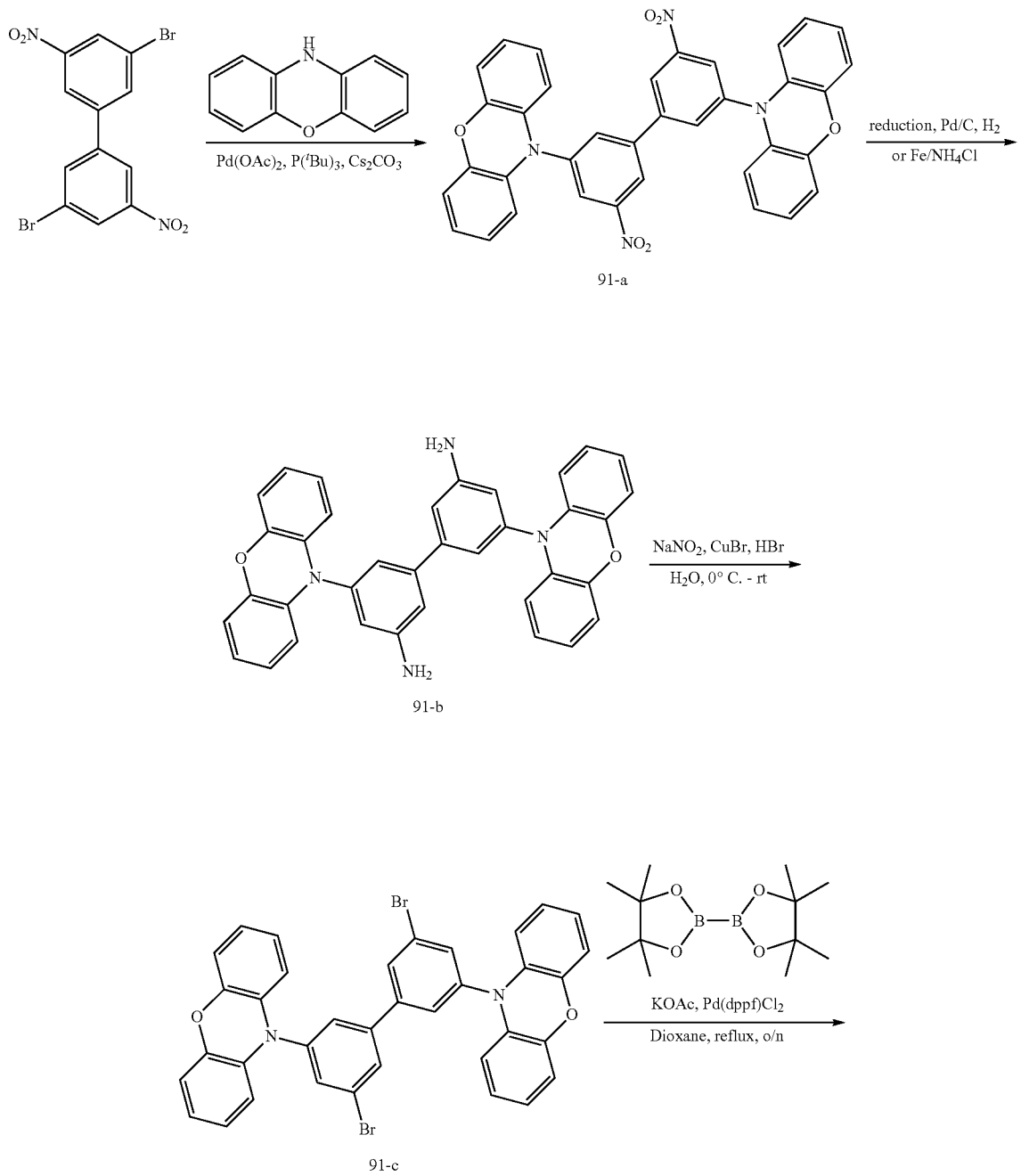

-continued

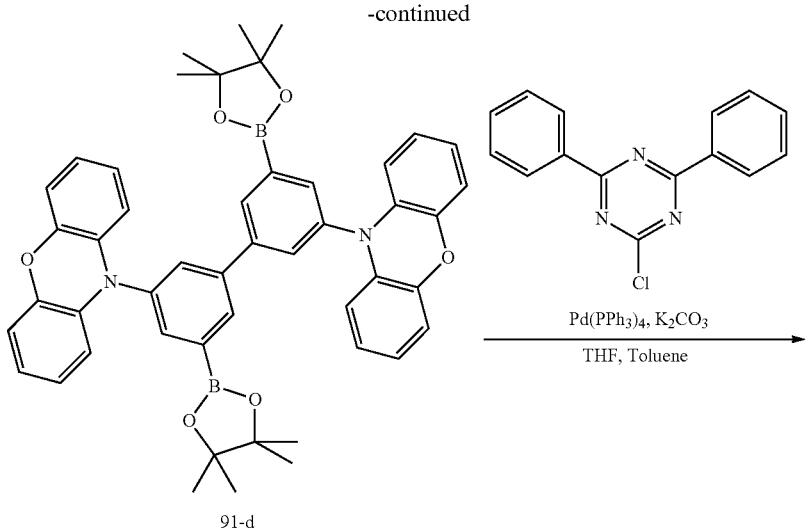

91-d

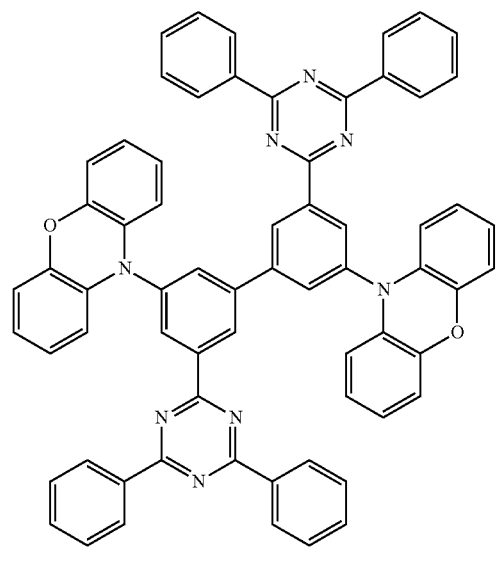

91

The first step of the synthesis process of the compound 91 may be to synthesize the compound 91-a illustrated in the synthesis route. 3,3'-dibroMo-5,5'-dinitrobiphenyl (20.0 g, 49.8 mmol), phenoxazine (18.4 g, 100.4 mmol), Pd(OAc)$_2$ (1.2 g, 5.4 mmol), tri-tert-butylphosphine (1.6 g, 7.8 mmol) and Cs$_2$CO$_3$ (48.6 g, 149.4 mmol) may be dissolved in toluene; and may be refluxed for 8 hours in a nitrogen environment. Then, the solvent may be completely evaporated under vacuum. The residues may be added into pentane; and stirred and filtered. Then, the products may be purified by a silicone gel chromatographic column. Thus, the solid compound 91-a (12.4 g, 41%) may be obtained.

The second step of the synthesis process of the compound 91 may be to synthesis the compound 91-b illustrated in the synthesis route. The intermediate 91-a (12.4 g, 20.4 mmol) may be dissolved in methanol. Under the protection of an Ar gas, 2 g Pd/C may be slowly added into the solution. After substituting the gas in the reaction flask with hydrogen, the reaction may be continued for 20 hours in the hydrogen environment. After filtering and evaporating the solvent, the intermediate 91-b (8.8 g, 79%) may be obtained.

The third step of the synthesis process of the compound 91 may be to synthesize the compound 91-c illustrated in the synthesis route. NaNO$_2$ (6.7 g, 96.6 mmol) may be dissolved in 8 ml water. Such a solution may be slowly added into a mixture of the intermediate 91-b (8.8 g, 16.1 mmol) and 10 ml of HBr (approximately 81.0 mmol) with a concentration of 48%; and stirred for 1 hour in an ice bath (0° C.). Under the ice bath condition, 10 ml CuBr in HBr solution (4.9 g, 33.8 mmol) may be added into the mixture; and the reaction may continue for 1 hour in the ice bath. Then, the mixture may be heated to 60° C.; and react for 2 hours. After being cooling down, an extraction process may be performed using 50 ml ethyl acetate. The organic layer may be washed by water for a couple of times; and dried by dehydrated MgSO$_4$. After filtering and evaporating the solvent, the intermediate 91-c (8.5 g, yield 78%) may be obtained.

The fourth step of the synthesis process of the compound 91 may be to synthesize the compound 91-d illustrated in the synthesis route. Under the N$_2$ gas flow, the catalyst Pd(dppf)Cl$_2$ (0.7 g, 0.9 mmol), KOAc (0.9 g, 8.8 mmol), and bis(pinacolato)diboron (7.0 g, 27.7 mmol) may be mixed in a reaction flask. The intermediate 91-c (8.5 g, 12.6 mmol) may be dissolved in 200 ml 1,4-Dioxane solution; and added into the reaction flask. The mixture may be refluxed for 12 hours. After cooling down, toluene may be added to perform an extraction process. Then, the product may be washed by water for a plurality of times; and dried by dehydrated MgSO₄. The organic layer may be filtered; and the solvent may be evaporated. Then, the product may be purified by a silicone gel chromatographic column; and the intermediate 91-d (4.7 g, yield 49%) may be obtained.

The fifth step of the synthesis process of the compound 91 may be to synthesize the final compound 91 illustrated in the synthesis route. 2-chloro-4,6-diphenyl-1,3,5-triazine (3 g, 11.2 mmol), the catalyst Pd(PPh₃)₄ (0.7 g, 0.6 mmol) and the intermediate 91-d (4.2 g, 6.2 mmol) may be dissolved in 100 ml THF; and the mixture may dropped into the 100 ml K₂CO₃ (3.1 g, 22.4 mmol) water solution. The mixture may be stirred and refluxed for 2 days. After cooling down, toluene may be added to perform an extraction process. Then, the product may be washed by water for a plurality of times; and dried by dehydrated MgSO₄. The organic layer may be filtered; and the solvent may be evaporated. Then, the product may be purified by a silicone gel chromatographic column; and the compound 91 (3.2 g, yield 53%) may be obtained.

An LC-MS method may be used to analyze the final product (the obtained compound 91). The ESI-MS (m/z) of the final product is approximately 979.2 [M+H]⁺. Such a value corresponds to the molecular weight of the compound 91.

Embodiment 22 describes the synthesis route and the synthesis process of the compound 163. The synthesis route is illustrated as below.

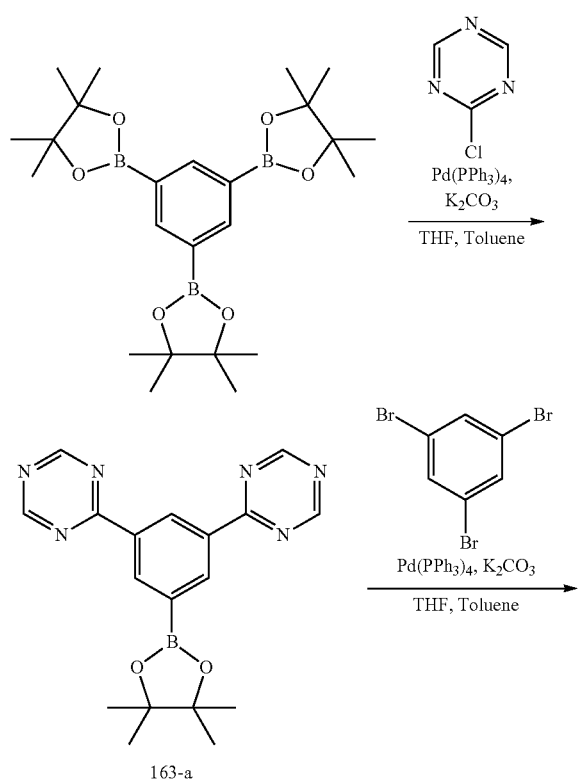

163-a

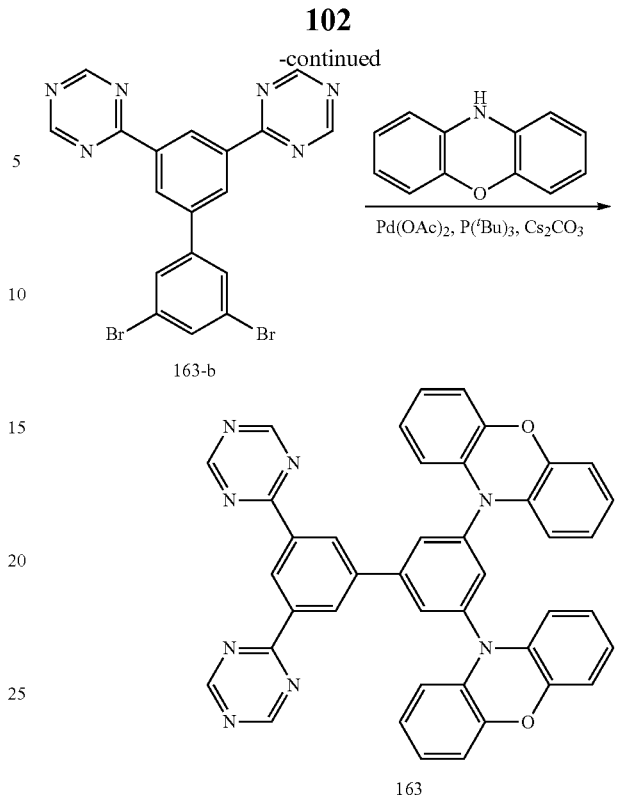

163

The first step of the synthesis process of the compound 163 may be to synthesize the compound 163-a illustrated in the synthesis route. 2-chloro1,3,5-triazine (9.2 g, 79.8 mmol), the catalyst Pd(PPh₃)₄ (4.6 g, 4.0 mmol), and 1,3,5-phenyltriboronic acid, pinacol ester (20.0 g, 43.9 mmol) may be dissolved in THF; and dropped into 100 ml K₂CO₃ (22.1 g, 159.6 mmol) water solution; and may be stirred and refluxed for 2 days. After cooling down, toluene may be added to perform an extraction process. Then, the product may be washed by water for a plurality of times; and dried by dehydrated MgSO₄. The organic layer may be filtered; and the solvent may be evaporated. Then, the product may be purified by a silicone gel chromatographic column; and the compound 163-a (4.5 g, yield 28%) may be obtained.

The second step of the synthesis process of the compound 163 may be to synthesize the compound 163-b illustrated in the synthesis route. Tribromobenzene (3.5 g, 11.2 mol), the catalyst Pd(PPh₃)₄ (0.7 g, 0.6 mmol) and the intermediate 163-a (4.5 g, 1.23 mmol) may be dissolved in 100 ml THF; and dropped into K₂CO₃ (3.1 g, 22.4 mmol) water solution. The mixture may be refluxed for 2 days. After cooling down, toluene may be added to perform an extraction process. Then, the product may be washed by water for a plurality of times; and dried by dehydrated MgSO₄. The organic layer may be filtered; and the solvent may be evaporated. Then, the product may be purified by a silicone gel chromatographic column; and the compound 163-b (2.5 g, yield 43%) may be obtained.

The third step of the synthesis process of the compound 163 may be to synthesize the final compound 163 illustrated in the synthesis route. The intermediate 163-b (2.5 g, 5.3 mmol), phenoxazine (2.1 g, 11.7 mmol), Pd(OAc)₂ (0.1 g, 0.5 mmol), tri-tert-butylphosphine (0.2 g, 0.8 mmol) and Cs₂CO₃ (5.2 g, 15.9 mmol) may be dissolved in toluene; and may be refluxed for 8 hours in a nitrogen environment. Then, the solvent may be completely evaporated. The residues may be added into pentane; and stirred. The product may be filtered; and purified by a silicone gel chromatographic column. The solid compound 163 (1.7 g, 47%) may be obtained.

An LC-MS method may be used to analyze the final product (the obtained compound 163). The ESI-MS (m/z) of the final product is approximately 675.1 [M+H]$^+$. Such a value corresponds to the molecular weight of the compound 163.

Embodiment 23 describes the synthesis route and the synthesis process of the compound 166. The synthesis route is illustrated as below.

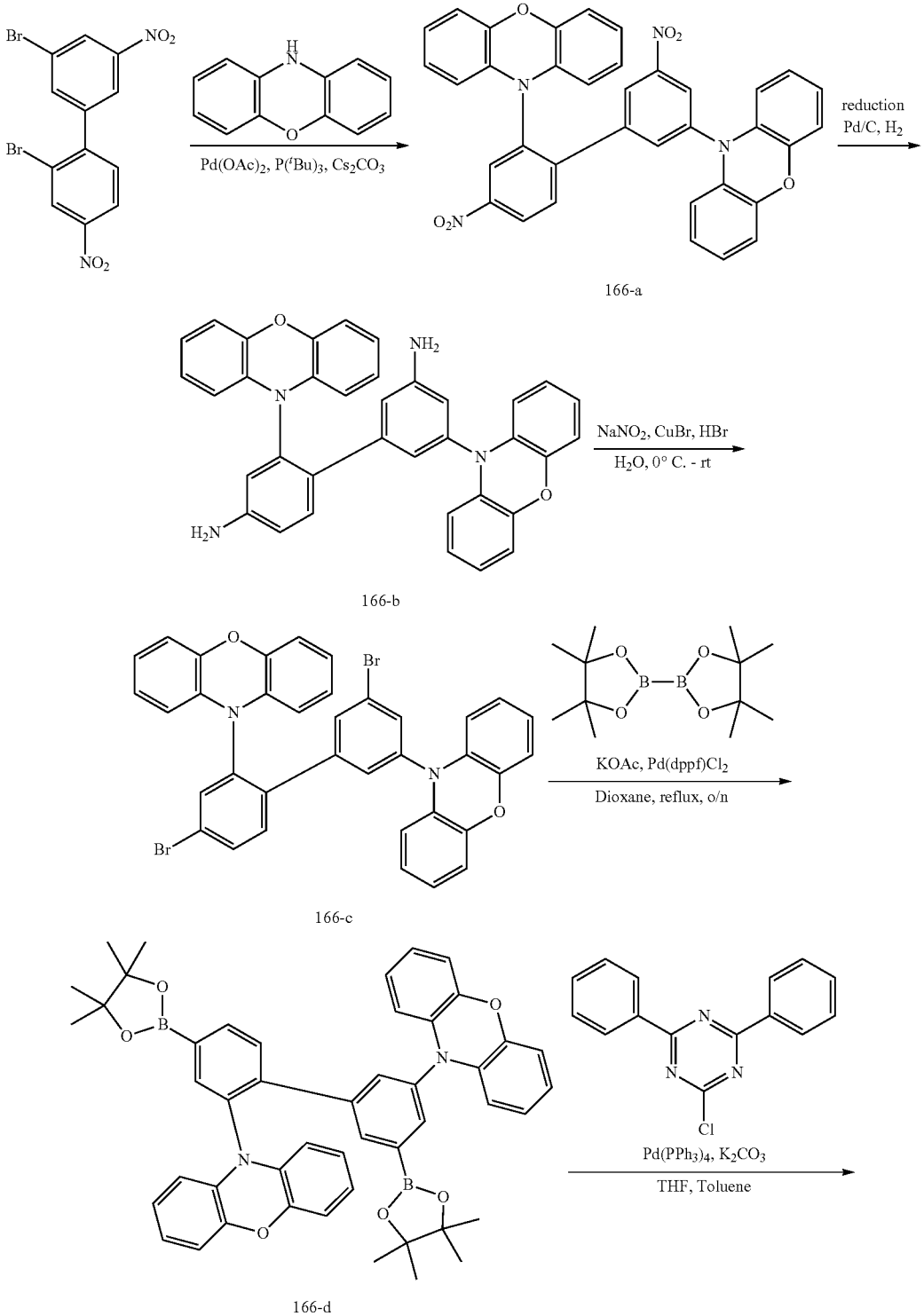

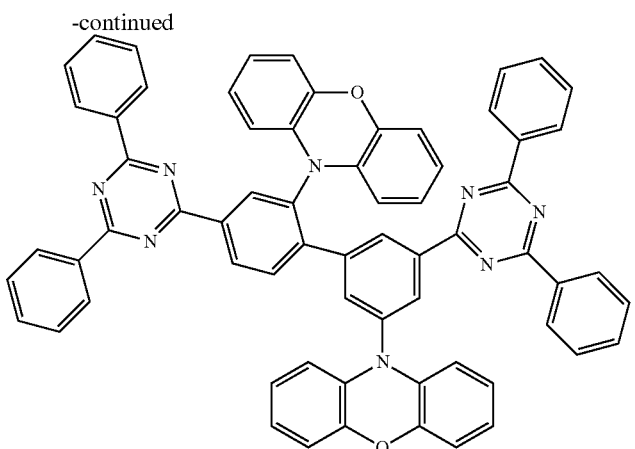

166

The first step of the synthesis process of the compound 166 may be to synthesize the compound 166-a illustrated in the synthesis route. 2,3'-dibroMo-4,5'-dinitrobiphenyl (20.0 g, 49.8 mmol), phenoxazine (18.4 g, 100.4 mmol), Pd(OAc)$_2$ (1.2 g, 5.4 mmol), tri-tert-butylphosphine (1.6 g, 7.8 mmol) and Cs$_2$CO$_3$ (48.6 g, 149.4 mmol) may be dissolved in toluene; and may be refluxed for 8 hours in a nitrogen environment. Then, the solvent may be completely evaporated under vacuum. The residues may be added into pentane; and stirred and filtered. Then, the products may be purified by a silicone gel chromatographic column. Thus, the solid compound 166-a (13.0 g, 43%) may be obtained.

The second step of the synthesis process of the compound 166 may be to synthesis the compound 166-b illustrated in the synthesis route. The intermediate 166-a (13 g, 21.4 mmol) may be dissolved in methanol. Under the protection of Ar gas, 3 g Pd/C may be slowly added into the solution. After substituting the gas in the reaction flask with hydrogen, the reaction may be continued for 20 hours in the hydrogen environment. After filtering and evaporating the solvent, the intermediate 166-b (8.5 g, 73%) may be obtained.

The third step of the synthesis process of the compound 166 may be to synthesis the compound 166-c illustrated in the synthesis route. NaNO$_2$ (6.5 g, 93.6 mmol) may be dissolved in 8 ml water. Such a solution may be slowly added into a mixture of the intermediate 166-b (8.5 g, 15.6 mmol) and 9.6 ml of HBr (approximately 78.8 mmol) with a concentration of 48%; and stirred for 1 hour in an ice bath (0° C.). Under the ice bath condition, 10 ml CuBr in HBr solution (4.7 g, 32.8 mmol) may be added into the mixture; and the reaction may continue for 1 hour in the ice bath. Then, the mixture may be heated to 60° C. and react for 2 hours. After being cooling down, an extraction process may be performed using 50 ml ethyl acetate. The organic layer may be washed by water for a couple of times; and dried by dehydrated MgSO$_4$. After filtering and evaporating the solvent, the intermediate 166-c (8.0 g, yield 76%) may be obtained.

The fourth step of the synthesis process of the compound 166 may be to synthesize the compound 166-d illustrated in the synthesis route. Under the N$_2$ gas flow, the catalyst Pd(dppf)Cl$_2$ (0.6 g, 0.8 mmol), KOAc (0.8 g, 8.3 mmol), and bis(pinacolato)diboron (6.6 g, 26.0 mmol) may be mixed in a reaction flask. The intermediate 166-c (8.0 g, 11.8 mmol) may be dissolved in 150 ml 1,4-Dioxane solution; and added into the reaction flask. The mixture may be refluxed for 12 hours. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the intermediate 166-d (3.8 g, yield 42%) may be obtained.

The fifth step of the synthesis process of the compound 166 may be to synthesize the final compound 166 illustrated in the synthesis route. 2-chloro-4,6-diphenyl-1,3,5-triazine (2.4 g, 9.1 mmol), the catalyst Pd(PPh$_3$)$_4$ (0.6 g, 0.5 mmol) and the intermediate 166-d (3.8 g, 5.0 mmol) may be dissolved in 100 ml THF; and then the mixture may be dropped into the 100 ml K$_2$CO$_3$ (2.5 g, 18.2 mmol) water solution. The mixture may be stirred and refluxed for 2 days. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the compound 166 (2.0 g, yield 41%) may be obtained.

An LC-MS method may be used to analyze the final product (the obtained compound 166). The ESI-MS (m/z) of the final product is approximately 979.2 [M+H]$^+$. Such a value corresponds to the molecular weight of the compound 166.

Embodiment 24 describes the synthesis route and the synthesis process of the compound 185. The synthesis route is illustrated as below.

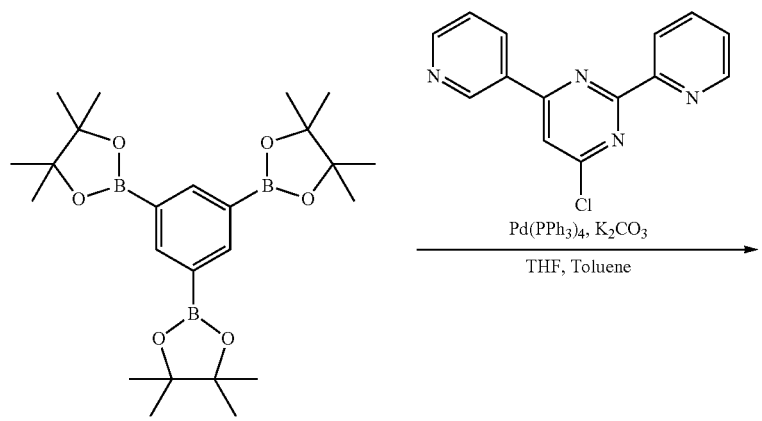
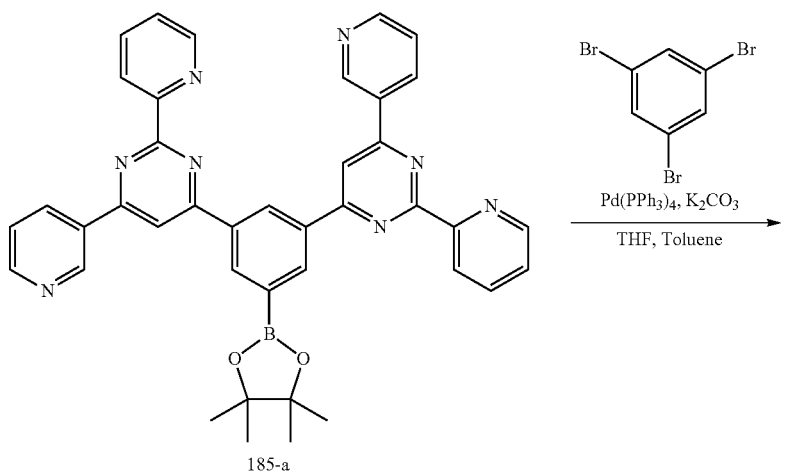
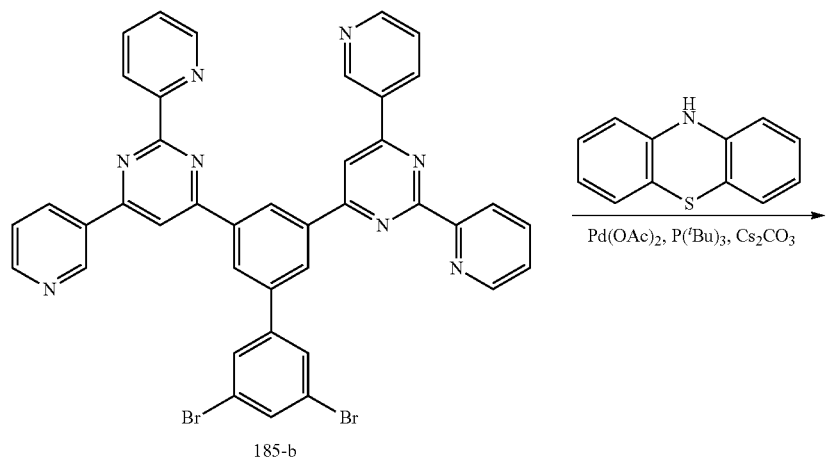

-continued

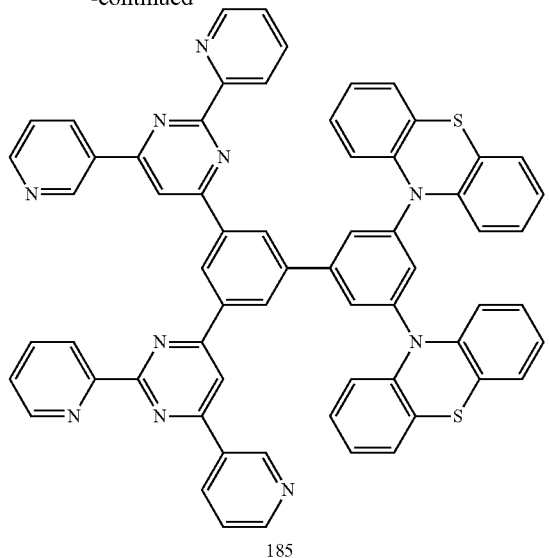

185

The first step of the synthesis process of the compound 185 may be to synthesize the compound 185-a illustrated in the synthesis route. 24-chloro-2-pyridin-2-yl-6-pyridin-3-ylpyrimidine (21.4 g, 79.8 mmol), the catalyst Pd(PPh$_3$)$_4$ (4.6 g, 4.0 mmol), and 1,3,5-phenyltriboronic acid, pinacol ester (20.0 g, 43.9 mmol) may be dissolved in THF; and dropped into 100 ml K$_2$CO$_3$ (22.1 g, 159.6 mmol) water solution; and may be stirred and refluxed for 2 days. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the compound 185-a (10.0 g, yield 34%) may be obtained.

The second step of the synthesis process of the compound 185 may be to synthesize the compound 185-b illustrated in the synthesis route. Tribromobenzene (4.2 g, 13.5 mmol), the catalyst Pd(PPh$_3$)$_4$ (0.8 g, 0.7 mmol) and the intermediate 185-a (10.0 g, 14.9 mmol) may be dissolved in 100 ml THF; and dropped into 100 ml K$_2$CO$_3$ (3.7 g, 27.0 mmol) water solution. The mixture may be refluxed for 2 days. After cooling down, toluene may be added to perform an extraction process. Then, the product may be washed by water for a couple of times; and dried by dehydrated MgSO$_4$. The organic layer may be filtered; and the solvent may be evaporated. Then, the product may be purified by a silicone gel chromatographic column; and the compound 185-b (4.3 g, yield 37%) may be obtained.

The third step of the synthesis process of the compound 185 may be to synthesize the final compound 185 illustrated in the synthesis route. The intermediate 185-b (4.3 g, 5.5 mmol), phenothiazine (2.4 g, 12.1 mmol), Pd(OAc)$_2$ (0.1 g, 0.6 mmol), tri-tert-butylphosphine (0.2 g, 0.8 mmol) and Cs$_2$CO$_3$ (5. g, 16.5 mmol) may be dissolved in toluene; and may be refluxed for 8 hours in a nitrogen environment. Then, the solvent may be completely evaporated. The residues may be added into pentane; and stirred. The product may be filtered; and purified by a silicone gel chromatographic column. The solid compound 185 (2.6 g, 46%) may be obtained.

An LC-MS method may be used to analyze the final product (the obtained compound 185). The ESI-MS (m/z) of the final product is approximately 1013.2 [M+H]$^+$. Such a value corresponds to the molecular weight of the compound 185.

Embodiment 25 describes the synthesis route and process of the compound 196. The synthesis route is illustrated as below.

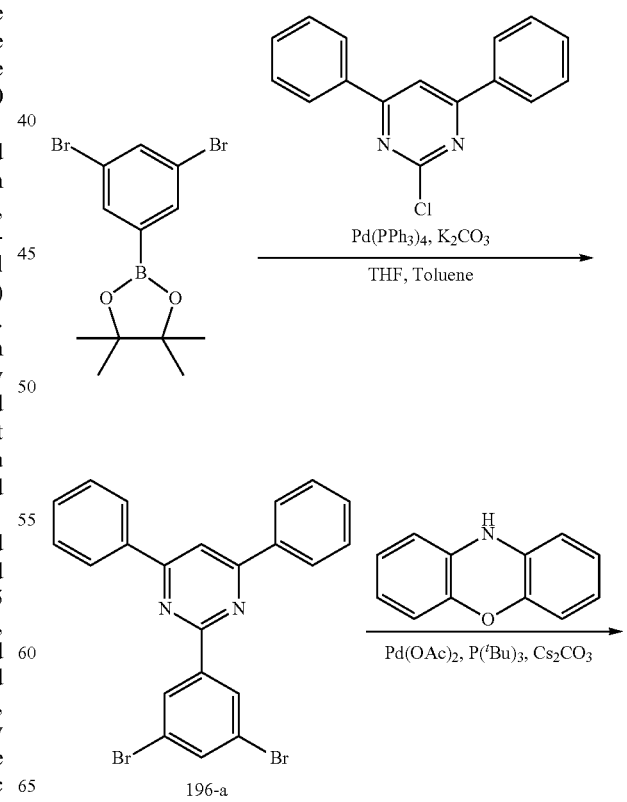

196-a

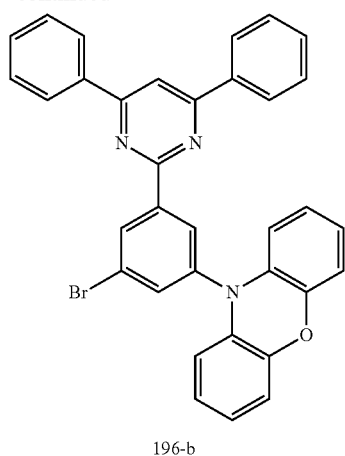

196-b

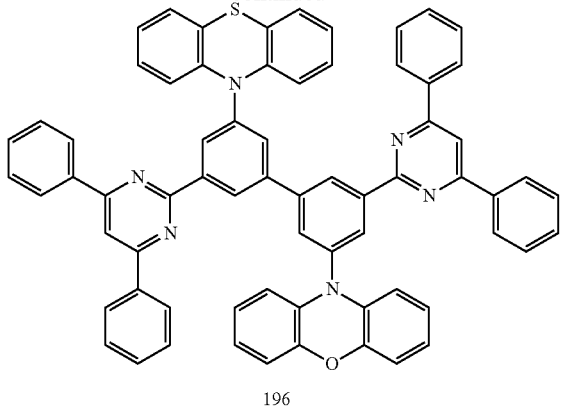

196

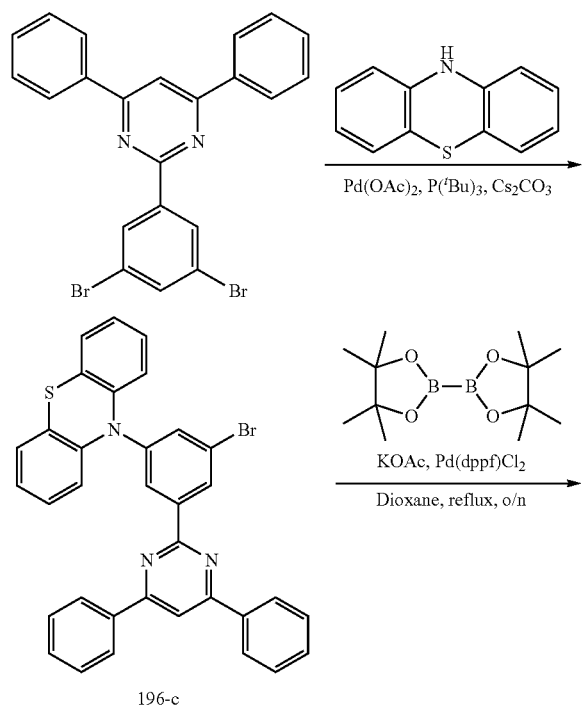

196-c

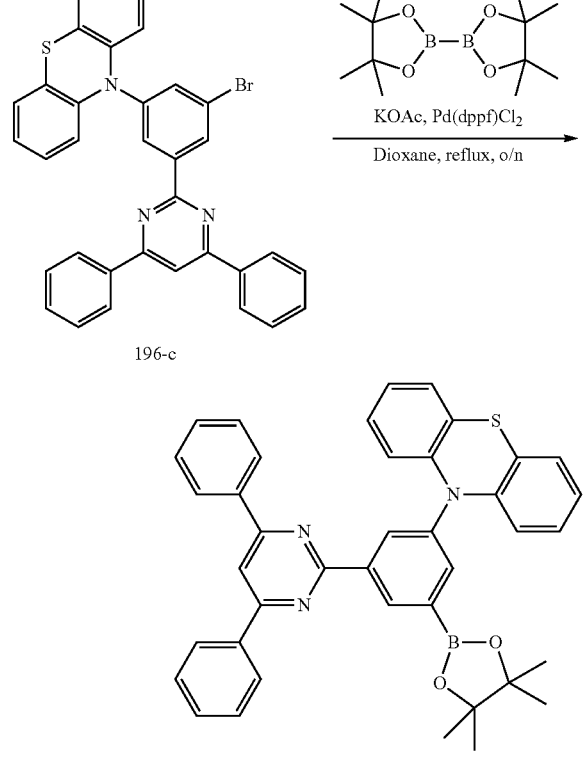

196-d

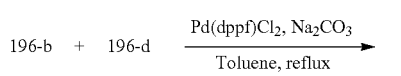

The first step of the synthesis process of the compound 196 may be to synthesize the compound 196-a illustrated in the synthesis route. 2-Chloro-4,6-diphenylpyrimidine (10.0 g, 37.5 mmol), the catalystPd(PPh$_3$)$_4$ (2.2 g, 1.9 mmol), and 2-(3,5-2-Bromophenylboronic)-4,4,5,5-tetraMethyl-1,3,2-dioxaborolane (14.9 g, 41.3 mmol) may be dissolved in 100 ml THF; and dropped into 100 ml K$_2$CO$_3$ (10.3 g, 74.6 mmol) water solution; and may be stirred and refluxed for 2 days. After cooling down, toluene may be added to perform an extraction process. Then, the product may be washed by water for a plurality of times; and dried by dehydrated MgSO4. The organic layer may be filtered; and the solvent may be evaporated. Then, the product may be purified by a silicone gel chromatographic column; and the compound 196-a (10.1 g, yield 58%) may be obtained.

The second step of the synthesis process of the compound 196 may be to synthesize the compound 196-b illustrated in the synthesis route. The intermediate 196-a (5.0 g, 10.7 mmol), phenoxazine (2.4 g, 11.8 mmol), Pd(OAc)$_2$ (0.1 g, 0.5 mmol), tri-tert-butylphosphine (0.2 g, 0.8 mmol) and Cs$_2$CO$_3$ (5.2 g, 16.1 mmol) may be dissolved in toluene; and may be refluxed for 8 hours in a nitrogen environment. Then, the solvent may be completely evaporated under vacuum. The residues may be added into pentane; and stirred and filtered. Then, the products may be purified by a silicone gel chromatographic column. Thus, the solid compound 196-b (2.4 g, 39%) may be obtained.

The third step of the synthesis process of the compound 196 may be to synthesize the compound 196-c illustrated in the synthesis route. The intermediate 196-a (5.0 g, 10.7 mmol), phenothiazine (2.2 g, 11.8 mmol), Pd(OAc)$_2$ (0.1 g, 0.5 mmol), tri-tert-butylphosphine (0.2 g, 0.8 mmol) and Cs$_2$CO$_3$ (5.2 g, 16.1 mmol) may be dissolved in toluene; and may be refluxed for 8 hours in nitrogen environment. Then, the solvent may be completely evaporated under vacuum. The residues may be added into pentane; and stirred and filtered. Then, the products may be purified by a silicone gel chromatographic column. Thus, the solid compound 196-c (3.0 g, 48%) may be obtained.

The fourth step of the synthesis process of the compound 196 may be to synthesize the compound 196-d. Under the N$_2$ gas flow, the catalyst Pd(dppf)Cl$_2$ (0.1 g, 0.2 mmol), KOAc (0.2 g, 1.8 mmol), and bis(pinacolato)diboron (6.6 g, 5.6 mmol) may be mixed in a reaction flask. The intermediate 196-c (2.9 g, 5.1 mmol) may be dissolved in 100 ml 1,4-Dioxane solution; and added into the reaction flask. The mixture may be refluxed for 12 hours. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the intermediate 196-d (1.2 g, yield 36%) may be obtained.

The fifth step of the synthesis process of the compound 196 may be to synthesize the final compound 196 illustrated in the synthesis route. The intermediate 196-b (1.0 g, 1.8 mmol), the intermediate 196-d (1.1 g, 1.8 mmol) and the catalyst Pd(PPh$_3$)$_4$ may be dissolved in 100 ml THF; and may be dropped into 100 ml K$_2$CO$_3$ (0.5 g, 3.6 mmol) water solution. The mixture may be stirred and refluxed for 2 days. After cooling down, toluene may be added to perform an extraction process. Then, the product may be washed by water for a plurality of times; and dried by dehydrated MgSO$_4$. The organic layer may be filtered; and the solvent may be evaporated. Then, the product may be purified by a silicone gel chromatographic column; and the compound 196 (1.0 g, yield 56%) may be obtained An LC-MS method may be used to analyze the final product (the obtained compound 196). The ESI-MS (m/z) of the final product is approximately 993.1 [M+H]$^+$. Such a value corresponds to the molecular weight of the compound 196.

Figure 6:
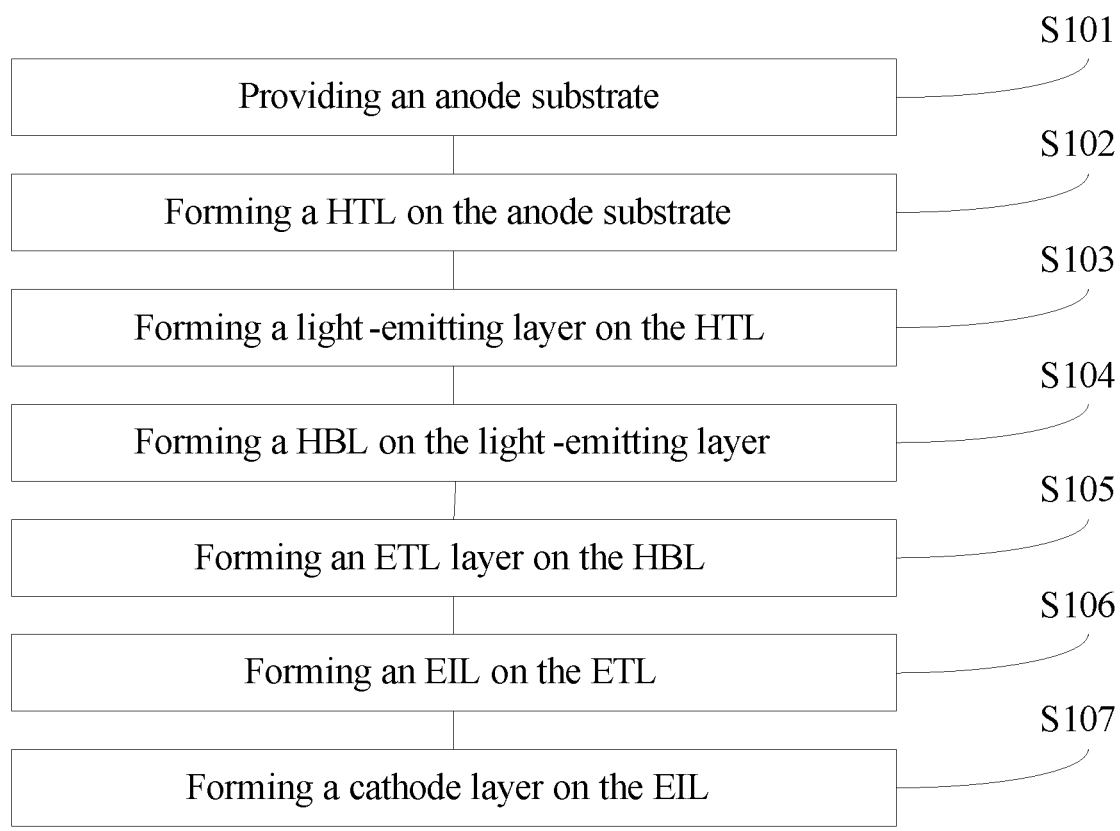
FIG. 6 illustrates an exemplary fabrication process of an organic photoelectric apparatus consistent with the disclosed embodiments.

FIG. 6 illustrates an exemplary fabrication process of the photoelectric apparatus having the disclosed compound consistent with the disclosed embodiments. Embodiments 26-36 describe the exemplary fabrication processes of organic photoelectric apparatus consistent with the disclosed embodiments. Control (or reference) embodiments 1-2 describe fabrication processes of two control organic photoelectric apparatus.

FIG. 6 illustrates an exemplary fabrication process of the organic photoelectric apparatus having the disclosed compound. As shown in FIG. 6, the method includes providing an anode substrate (S101); forming a HTL on the anode substrate (S102); forming a light-emitting layer on the HTL using at least one disclosed compound (S103); forming a HBL on the light-emitting layer (S104); forming an ETL on the HBL (S105); forming an EIL on the ETL (S106); and forming a cathode layer on the EIL (S107). For illustrative purposes, the disclosed compound will be used as the host material of one or more of the organic layers in the embodiments 26-32; and may be used as co-doping material in the embodiments 33-36.

Specifically, in the embodiment 26, an anode substrate having an ITO film with a thickness of 100 nm may be provided. The anode substrate having the ITO film may be sequentially cleaned by DI water, acetone and isopropanol alcohol in an ultrasound bath; and may be put into an oven. After a 30 minute surface treatment, the cleaned anode substrate may be transferred to a vacuum evaporation chamber. The photoelectric apparatus having a plurality of layers may be deposited at a pressure of 2×10$^{-6}$ Pa. An N,N'-Bis-(1-naphthalenyl)-N,N'-bis-phenyl-(1,1'-biphenyl)-4,4'-diamine (NPD) layer with a thickness of 60 nm may be deposited on the ITO film; and a 4,4',4"-Tris(carbazol-9-yl)-triphenylamine (TCTA) layer with a thickness of 10 nm may be deposited on the NPD layer. The NPD layer and the TCTA layer may form the HTL. Further, the light-emitting layer with a thickness of 30 nm may be deposited on the HTL. The light-emitting layer may include the disclosed compound 91 as the host material (94 wt %) and Ir(ppy)$_3$ as the blue phosphorescent doping material (6 wt %). The host material and the doping material may be deposited simultaneously. Further, a bis(2-methyl-8-quinolinolato-N1,O8)-(1,1'-Biphenyl-4-olato)aluminum (BAlq) layer with a thickness of 5 nm may be deposited on the light-emitting layer to be used as the HBL. Then, a 4,7-diphenyl-1,10-phenanthroline (BPhen) layer with a thickness of 20 nm may be deposited on the HBL to be used as the ETL. Then, a LiF layer with a thickness of 1 nm may be deposited on the ETL to be used as the EIL. Then, an Al layer with a thickness of the 100 nm may be deposited on the EIL to be used as a cathode layer. Thus, the organic photoelectric apparatus may have a structure of ITO (100 nm)/NPD (60 nm)/TCTA (10 nm)/Ir(ppy)$_3$:91 (6 wt %, 30 nm)/BAlq (5 nm)/Bphen (20 nm)/LiF (1 nm)/Al (100 nm).

In the embodiment 27, the disclosed compound 61 may be used to substitute the compound 91 described in the embodiment 26 as the host material. Other structures and steps may be similar to those described in the embodiment 26.

In the embodiment 28, the disclosed compound 62 may be used to substitute the compound 91 described in the embodiment 26 as the host material. Other structures and steps may be similar to those described in the embodiment 26.

In the embodiment 29, the disclosed compound 63 may be used to substitute the compound 91 described in the embodiment 26 as the host material. Other structures and steps may be similar to those described in the embodiment 26.

In the embodiment 30, the disclosed compound 64 may be used to substitute the compound 91 described in the embodiment 26 as the host material. Other structures and steps may be similar to those described in the embodiment 26.

In the embodiment 31, the disclosed compound 163 may be used to substitute the compound 91 described in the embodiment 26 as the host material. Other structures and steps may be similar to those described in the embodiment 26.

In the embodiment 32, the disclosed compound 185 may be used to substitute the compound 91 described in the embodiment 26 as the host material. Other structures and steps may be similar to those described in the embodiment 26.

In the control embodiment 1, compound CBP illustrated below is used to substitute the compound 91 described in the embodiment 26 as the host material. Other structures and steps may be similar to those described in the embodiment 26.

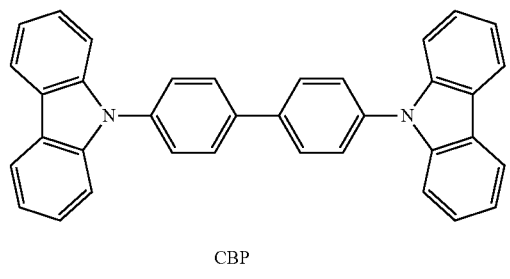 [SMILES: c1ccc2c(c1)c1ccccc1n2-c1ccc(-c2ccc(-n3c4ccccc4c4ccccc43)cc2)cc1 ; "CBP"]

CBP

In the embodiment 33, TBRb (1 wt %) illustrated below may be used as the doping material; and the disclosed compound 1 (25 wt %) may be used as a co-doping material. The compound CBP (74 wt %) may be used as the host material. The TBRb, the disclosed compound 1 and the CBP may be deposited simultaneously to be used as the light-emitting layer with a thickness of 30 nm. Other structures and steps may be similar to those described in the embodiment 26.

That is, the organic photoelectric apparatus may have a structure of ITO (100 nm)/NPD (60 nm)/TCTA (10 nm)/

RBRb:1:CBP (1 wt %:25%, 30 nm)/BAlq (5 nm)/Bphen (20 nm)/LiF (1 nm)/Al (100 nm).

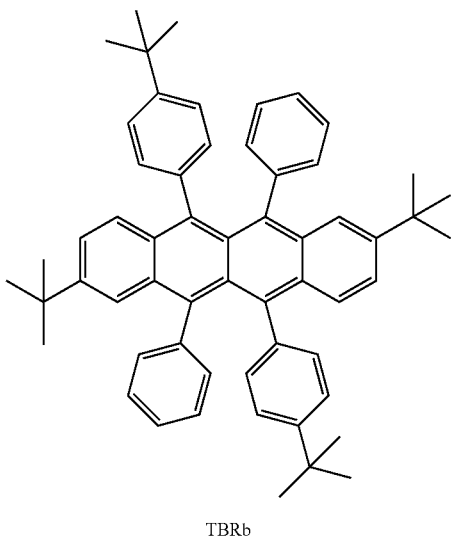 [SMILES: CC(C)(C)c1ccc(-c2c3ccc(C(C)(C)C)cc3c(-c3ccccc3)c3c(-c4ccc(C(C)(C)C)cc4)c4ccc(C(C)(C)C)cc4c(-c4ccccc4)c23)cc1 ; "TBRb"]

TBRb

In the embodiment 34, the disclosed compound 91 may be used to substitute the compound 1 described in the embodiment 33 as the co-doping material. Other structures and steps may be similar to those described in the embodiment 33.

In the embodiment 35, the disclosed compound 163 may be used to substitute the compound 1 described in the embodiment 33 as the co-doping material. Other structures and steps may be similar to those described in the embodiment 33.

In the embodiment 36, the disclosed compound 166 may be used to substitute the compound 1 described in the embodiment 33 as the co-doping material. Other structures and steps may be similar to those described in the embodiment 33.

In the control embodiment 2, TBRb (1 wt %) is used as the doping material; and CBP is used as the host material. TBRb and CBP are deposited simultaneously to be used as the light-emitting layer with a thickness of 30 nm. Other structures and steps may be similar to those described in the embodiment 33

The performance of the photoelectric apparatus described in the embodiments 26-36 and the control embodiments 1-2 may be evaluated from any aspects, and by any appropriate methods.

In one embodiment, the current of the photoelectric apparatus described in the embodiments 26-36 and the control embodiments 1-2 varying with the applied voltage is measured by a Keithley 2365 nanovoltagemeter. The current densities of the organic photoelectric apparatus at different voltages are obtained by dividing the current with the light-emitting area.

The brightness and the radiant energy flow density of the photoelectric apparatus described in the embodiments 26-36 and the control embodiments 1-2 at different voltages may be measured by a Konicaminolta CS 2000 spectroradiometer. According to the brightness and the radiant energy of the photoelectric apparatus at different voltages, the current efficiency (Cd/A) and the external quantum efficiency EQE at a same current density (10 mA/cm$^2$) may be obtained.

The testing results of the photoelectric apparatus described in embodiments 26-32 and the control embodiment 1 are illustrated in Table 2. The testing results of the photoelectric apparatus described in embodiments 33-36 and the control embodiment 2 are illustrated in Table 3.

TABLE 2

Testing results corresponding to different host materials

|  | Voltage (V) | Current efficiency (Cd/A) | EQE |
| --- | --- | --- | --- |
| Embodiment 26 | 4.5 | 43.6 | 17.9 |
| Embodiment 27 | 4.4 | 44.1 | 18.1 |
| Embodiment 28 | 4.1 | 47.9 | 18.4 |
| Embodiment 29 | 4.0 | 45.3 | 18.2 |
| Embodiment 30 | 4.1 | 43.7 | 17.8 |
| Embodiment 31 | 4.2 | 49.1 | 18.6 |
| Embodiment 32 | 4.5 | 42.3 | 17.7 |
| Control embodiment 1 | 5.1 | 40.3 | 15.6 |

TABLE 3

Testing results corresponding to different co-doping materials

|  | Voltage (V) | Current efficiency (Cd/A) | EQE |
| --- | --- | --- | --- |
| Embodiment 33 | 6.7 | 45.2 | 10.4 |
| Embodiment 34 | 6.5 | 48.7 | 11.2 |
| Embodiment 35 | 7.1 | 40.8 | 9.7 |
| Embodiment 36 | 6.8 | 46.6 | 10.8 |
| Control embodiment 2 | 9.3 | 8.1 | 2.7 |

According to table 2 and table 3, under a same current density (10 mA/cm$^2$), comparing with the photoelectric apparatus described in the control embodiments 1-2, the photoelectric apparatus described in the embodiments 26-36, which have the disclosed compounds as host material or co-doping material, may have lower drive voltages, higher current efficiencies, and higher external quantum efficiencies. That is, the organic photoelectric apparatus having the disclosed compounds may have desired performance. Thus, the disclosed compounds may be used as the host materials, and/or the co-doping materials of the organic layers of the photoelectric apparatus.

The above detailed descriptions only illustrate certain exemplary embodiments of the present invention, and are not intended to limit the scope of the present invention. Those skilled in the art can understand the specification as whole and technical features in the various embodiments can be combined into other embodiments understandable to those persons of ordinary skill in the art. Any equivalent or modification thereof, without departing from the spirit and principle of the present invention, falls within the true scope of the present invention.

What is claimed is:

1. A nitrogen-containing heterocyclic compound having a general formula (I):

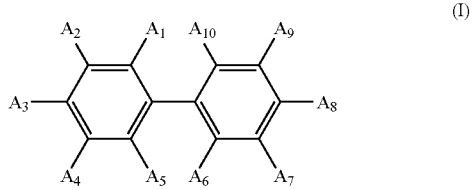

wherein $A_1$, $A_2$, $A_3$, $A_4$, $A_5$, $A_6$, $A_7$, $A_8$, $A_9$, and $A_{10}$ are independently selected from a hydrogen atom, a compound having a general formula (II), and a compound having a general formula (III), $A_1$, $A_2$, $A_3$, $A_4$, $A_5$, $A_6$, $A_7$, $A_8$, $A_9$, and $A_{10}$ include two compounds having the general formula (II) and two compounds having the general formula (III), the two compounds having the general formula (II) are included in one of $A_1$, $A_2$, $A_3$, $A_4$ and $A_5$, and one of $A_6$, $A_7$, $A_8$, $A_9$, and $A_{10}$, respectively, the two compounds having the general formula (III) are included in one of $A_1$, $A_2$, $A_3$, $A_4$ and $A_5$, and one of $A_6$, $A_7$, $A_8$, $A_9$, and $A_{10}$, respectively, and the compound having the general formula (III) included in one of $A_1$, $A_2$, $A_3$, $A_4$ and $A_5$ is different from the compound having the general formula (III) included in one of $A_6$, $A_7$, $A_8$, $A_9$ and $A_{10}$, the general formula (II) being:

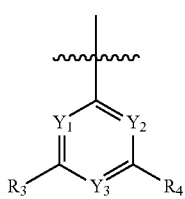

(II)

wherein $Y_1$, $Y_2$, and $Y_3$ are independently selected from C and N; and $R_3$ and $R_4$ are independently selected from $C_{6-30}$ aromatic group and $C_{2-30}$ heterocyclic aromatic group, and the general formula (III) being:

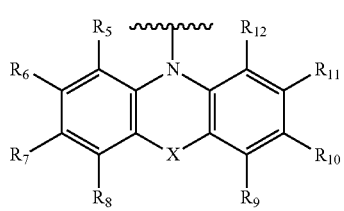

(III)

wherein X is selected from one of —O—, —S—, —C(CH$_3$)$_2$, —Si(CH$_3$)$_2$, and

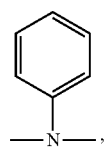

and $R_5$, $R_6$, $R_7$, $R_8$, $R_9$, $R_{10}$, $R_{11}$, and $R_{12}$ are independently selected from hydrogen, deuterium, $C_{1-30}$ alkyl group, $C_{6-30}$ aromatic group, and $C_{2-30}$ heterocyclic aromatic group, wherein $A_3$ and $A_8$ are one of the followings:
both $A_3$ and $A_8$ are hydrogen atoms;
when $A_3$ and $A_8$ include the two compounds having the general formula (II), the two compounds having the general formula (II) included in $A_3$ and $A_8$ are the same; and when $A_3$ and $A_8$ include two compounds having the general formula (III), the two compounds having the general formula (III) included in $A_3$ and $A_8$ are different; and wherein the nitrogen-containing heterocyclic compound is synthesized using a biphenyl derivative as a starting material, wherein the biphenyl derivative includes two nitro groups and two bromo groups.

2. The nitrogen-containing heterocyclic compound according to claim 1, wherein:
an energy level difference ($\Delta E_{st}$) among a lowest singlet state $S_1$ and a lowest triplet state $T_1$ is smaller than or equal to approximately 0.30 eV.

3. The nitrogen-containing heterocyclic compound according to claim 1, wherein the compound having the general formula (II) comprises one of:

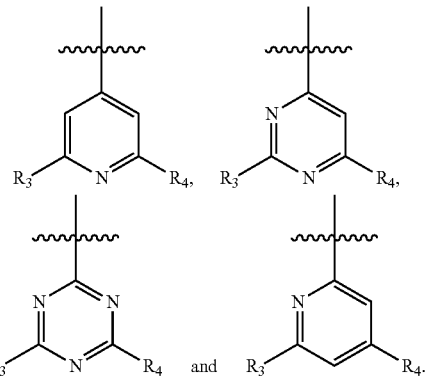

4. The nitrogen-containing heterocyclic compound according to claim 1, wherein:
$R_3$ and $R_4$ are independently selected from one or more of substituted or non-substituted phenyl group, substituted or non-substituted pyridyl group, substituted or non-substituted pyrimidyl group, and substituted or non-substituted triazinyl group.

5. The nitrogen-containing heterocyclic compound according to claim 1, wherein the compound having the general formula (II) is one of:

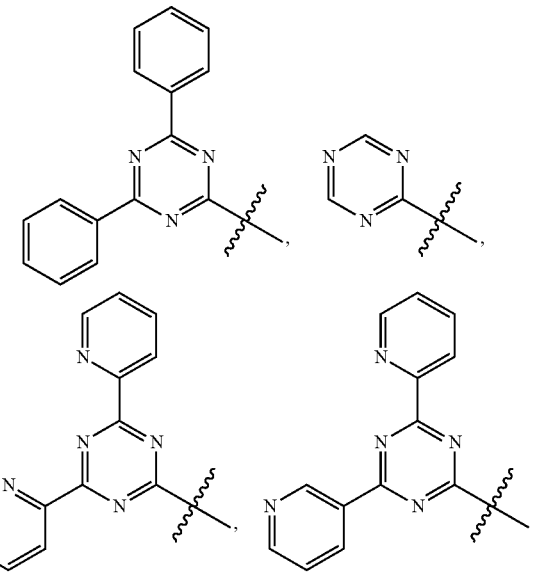

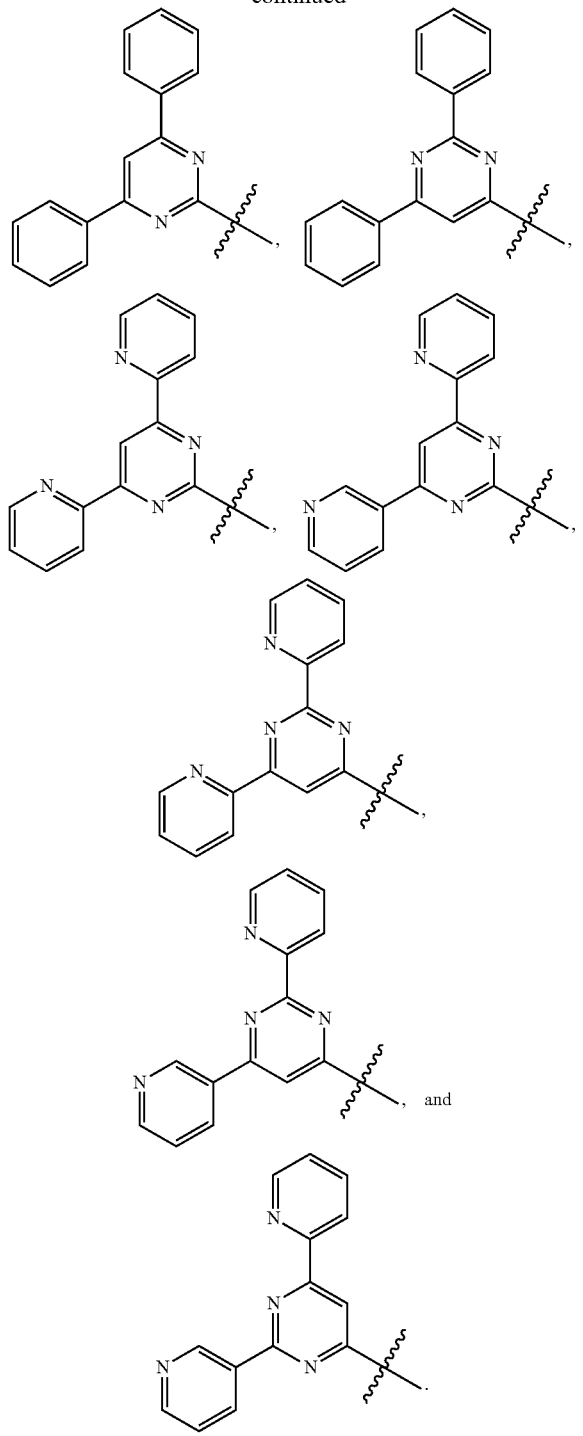

6. The nitrogen-containing heterocyclic compound according to claim 1, wherein:
$R_5$, $R_6$, $R_7$, $R_8$, $R_9$, $R_{10}$, $R_{11}$ and $R_{12}$ are all hydrogen.

7. An organic photoelectric apparatus, comprising:
an anode substrate;
at least one organic layer formed over the anode substrate; and
a cathode layer formed over the organic layer,
wherein the at least one organic layer includes at least one nitrogen-containing heterocyclic compound having a general formula (I):

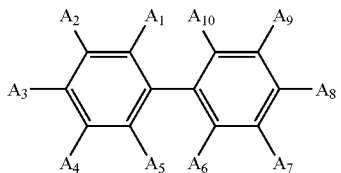

wherein $A_1$, $A_2$, $A_3$, $A_4$, $A_5$, $A_6$, $A_7$, $A_8$, $A_9$, and $A_{10}$ are independently selected from a hydrogen atom, a compound having a general formula (II), and a compound having a general formula (III), $A_1$, $A_2$, $A_3$, $A_4$, $A_5$, $A_6$, $A_7$, $A_8$, $A_9$, and $A_{10}$ include two compounds having the general formula (II) and two compounds having the general formula (III), the two compounds having the general formula (II) are included in one of $A_1$, $A_2$, $A_3$, $A_4$ and $A_5$, and one of $A_6$, $A_7$, $A_8$, $A_9$, and $A_{10}$, respectively, the two compounds having the general formula (III) are included in one of $A_1$, $A_2$, $A_3$, $A_4$ and $A_5$, and one of $A_6$, $A_7$, $A_8$, $A_9$, and $A_{10}$, respectively, and the compound having the general formula (III) included in one of $A_1$, $A_2$, $A_3$, $A_4$ and $A_5$ is different from the compound having the general formula (III) included in one of $A_6$, $A_7$, $A_8$, $A_9$ and $A_{10}$, the general formula (II) being:

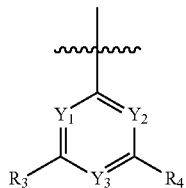

wherein $Y_1$, $Y_2$, and $Y_3$ are independently selected from C and N; and $R_3$ and $R_4$ are independently selected from $C_{6-30}$ aromatic group and $C_{2-30}$ heterocyclic aromatic group, and the general formula (III) being:

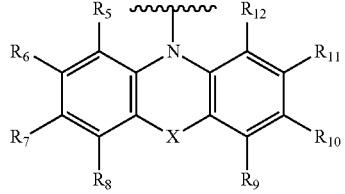

wherein X is selected from one of —O—, —S—, —C(CH$_3$)$_2$, —Si(CH$_3$)$_2$, and

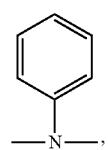

and $R_5$, $R_6$, $R_7$, $R_8$, $R_9$, $R_{10}$, $R_{11}$, and $R_{12}$ are independently selected from hydrogen, deuterium, $C_{1-30}$ alkyl group, $C_{6-30}$ aromatic group, and $C_{2-30}$ heterocyclic aromatic group, wherein $A_3$ and $A_8$ are one of the followings:

both $A_3$ and $A_8$ are hydrogen atoms;

when $A_3$ and $A_8$ include the two compounds having the general formula (II), the two compounds having the general formula (II) included in $A_3$ and $A_8$ are the same; and when $A_3$ and $A_8$ include two compounds having the general formula (III), the two compounds having the general formula (III) included in $A_3$ and $A_8$ are different; and wherein the at least one nitrogen-containing heterocyclic compound is synthesized using a biphenyl derivative as a starting material, wherein the biphenyl derivative includes two nitro groups and two bromo groups.

8. The organic photoelectric apparatus according to claim 7, wherein the organic layer comprises:

at least one light-emitting layer; and the at least one light-emitting layer includes the at least one nitrogen-containing heterocyclic compound, the at least one nitrogen-containing heterocyclic compound having the general formula (I).

9. The organic photoelectric apparatus according to claim 8, wherein:

the at least one nitrogen-containing heterocyclic compound is used as one of a host material, a doping material, and a co-doping material of the at least one light-emitting layer.

10. The organic photoelectric apparatus according to claim 7, wherein the organic layer further comprises:

one or at least two of a hole transport layer, a hole injection layer, a hole barrier layer, an electron transport layer, an electron injection layer, and an electron barrier layer.

11. The organic photoelectric apparatus according to claim 10, wherein:

the nitrogen-containing heterocyclic compound is a host material of the at least one light-emitting layer.

12. The organic photoelectric apparatus according to claim 7, wherein:

an energy level difference (ΔEst) among a lowest singlet state $S_1$ and a lowest triplet state $T_1$ of the nitrogen-containing heterocyclic compound is smaller than or equal to approximately 0.30 eV.

13. The nitrogen-containing heterocyclic compound according to claim 1, comprising one of:

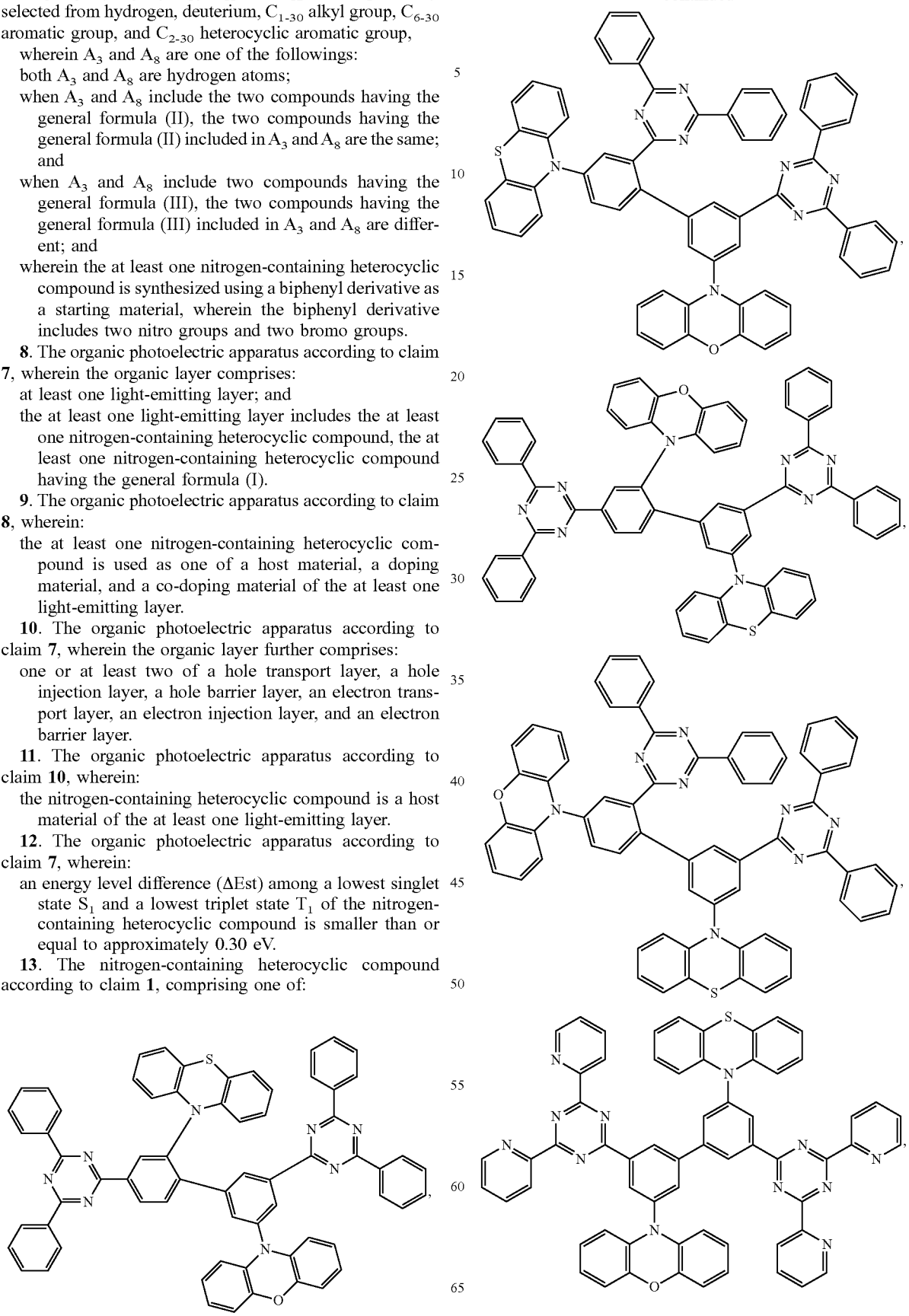

-continued

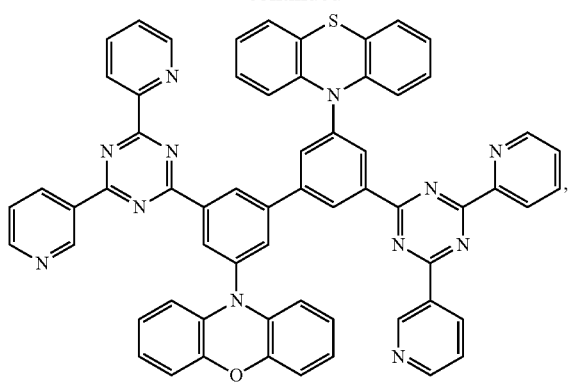

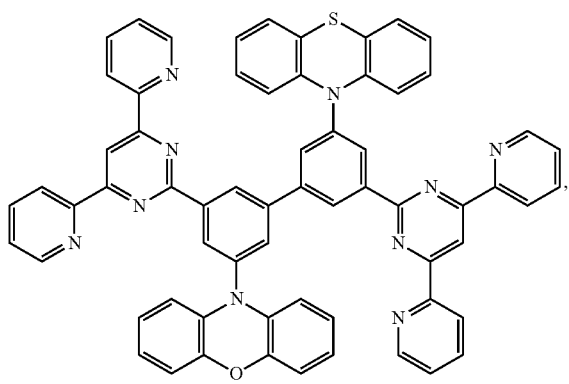

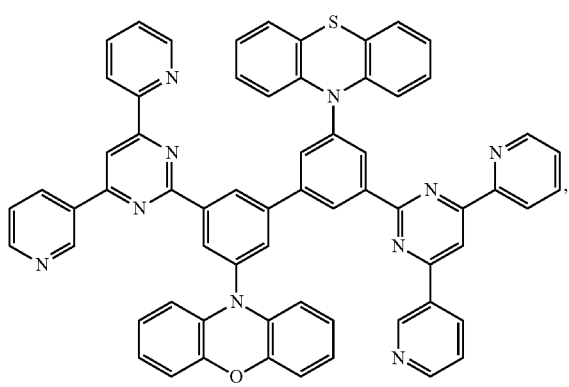

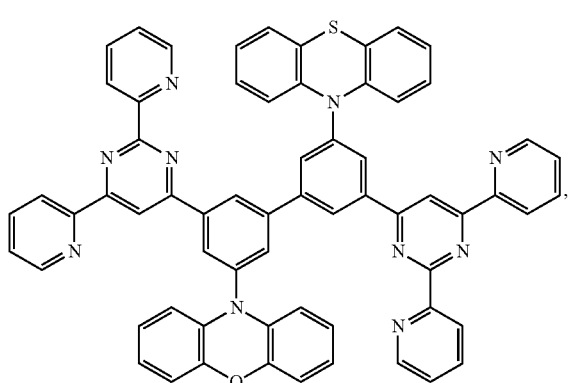

-continued

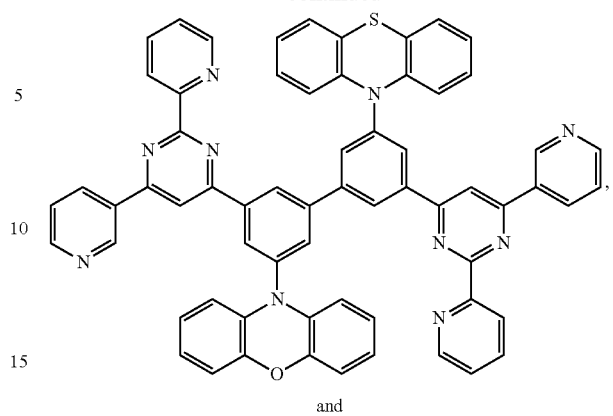

and

14. A nitrogen-containing heterocyclic compound having a general formula (I):

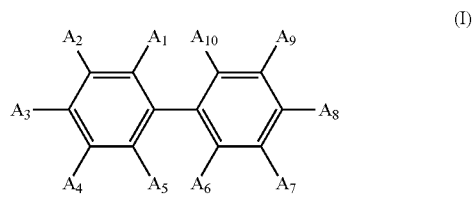

(I)

wherein $A_1$, $A_2$, $A_3$, $A_4$, $A_5$, $A_6$, $A_7$, $A_8$, $A_9$, and $A_{10}$ are independently selected from a hydrogen atom, a compound having a general formula (II), and a compound having a general formula (III), and $A_1$, $A_2$, $A_3$, $A_4$, $A_5$, $A_6$, $A_7$, $A_8$, $A_9$, and $A_{10}$ include two compounds having the general formula (II) and two compounds having the general formula (III), the two compounds having the general formula (II) are included in two of $A_1$, $A_2$, $A_3$, $A_4$ and $A_5$, or in two of $A_6$, $A_7$, $A_8$, $A_9$, and $A_{10}$, the two compounds having the general formula (III) are included in two of $A_1$, $A_2$, $A_3$, $A_4$ and $A_5$, or in two of $A_6$, $A_7$, $A_8$, $A_9$, and $A_{10}$, $A_1$, $A_2$, $A_3$, $A_4$ and $A_5$ have two compounds having the general formula (II) or the general formula (III), and $A_6$, $A_7$, $A_8$, $A_9$ and $A_{10}$ have two compounds having the general formula (II) or the general formula (III), the general formula (II) being:

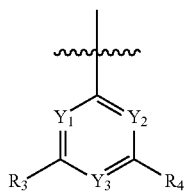
(II)

wherein $Y_1$, $Y_2$, and $Y_3$ are independently selected from C and N; and $R_3$ and $R_4$ are independently selected from $C_{6-30}$ aromatic group and $C_{2-30}$ heterocyclic aromatic group, and the general formula (III) being:

(III)

wherein X is selected from one of —NH—, —N(CH$_3$)—,

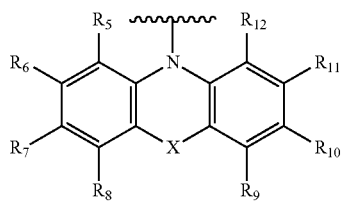

—SiH$_2$—, —Si(CH$_3$)$_2$—, —SiH(CH$_3$)—,

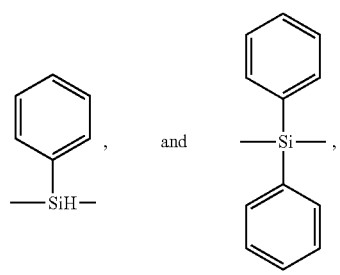

and and $R_5$, $R_6$, $R_7$, $R_8$, $R_9$, $R_{10}$, $R_{11}$, and $R_{12}$ are independently selected from hydrogen, deuterium, $C_{1-30}$ alkyl group, $C_{6-30}$ aromatic group, and $C_{2-30}$ heterocyclic aromatic group, and the nitrogen-containing heterocyclic compound is synthesized using a biphenyl derivative as a starting material, wherein the biphenyl derivative includes at least one compound selected

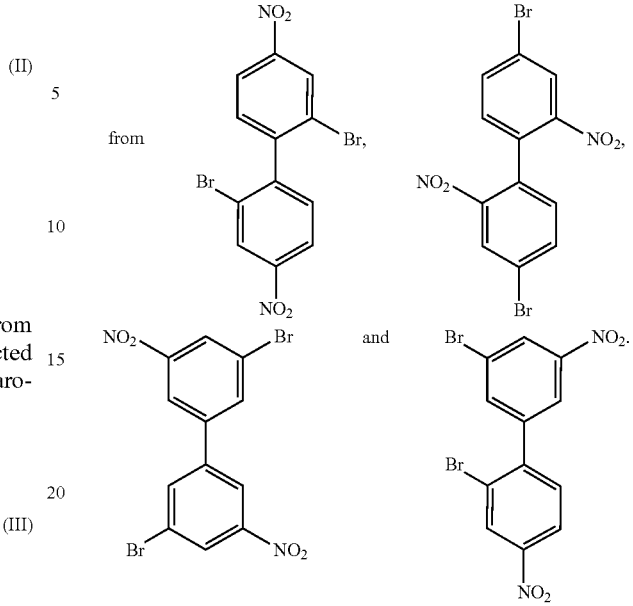

15. The nitrogen-containing heterocyclic compound according to claim 1, wherein:

when $A_3$ and $A_8$ include the two compounds having the general formula (II) that are the same, $A_1$, $A_2$, $A_4$, $A_5$, $A_6$, $A_7$, $A_9$, and $A_{10}$ include two compounds having the general formula (III).

16. The nitrogen-containing heterocyclic compound according to claim 1, wherein:

the biphenyl derivative as the starting material includes at least one compound selected

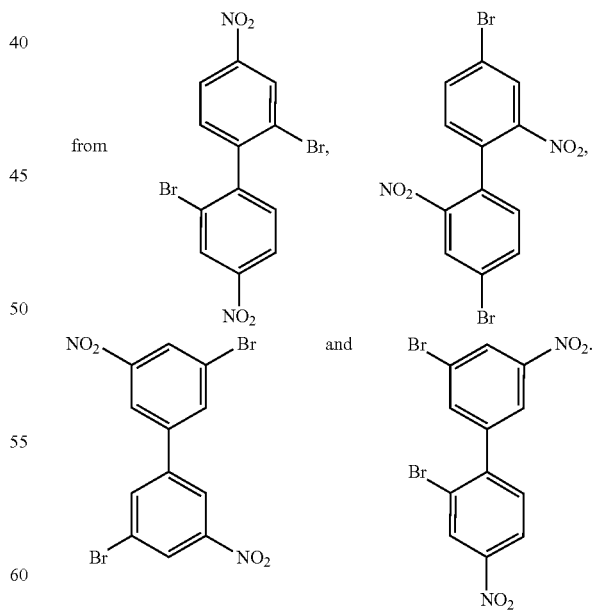

17. The at least one nitrogen-containing heterocyclic compound according to claim 7, wherein:

the biphenyl derivative as the starting material includes at least one compound selected from 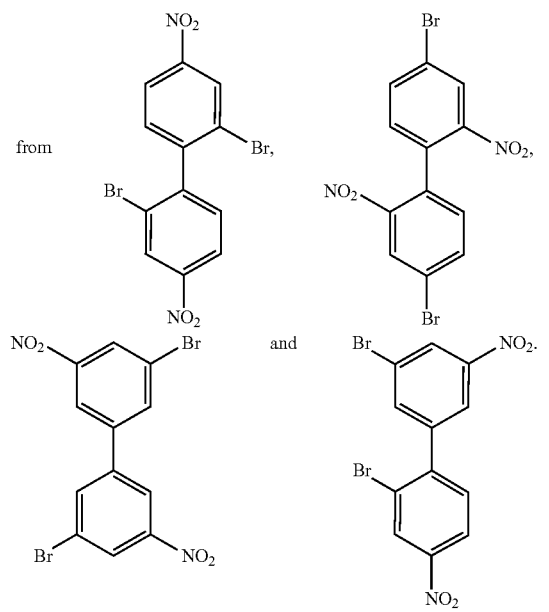 and